(12) United States Patent
Hobbs et al.

(10) Patent No.: US 6,887,889 B2
(45) Date of Patent: May 3, 2005

(54) ARYL AND BIARYL PIPERDINES WITH MCH MODULATORY ACTIVITY

(75) Inventors: Douglas W. Hobbs, Yardley, PA (US); Tao Guo, Dayton, NJ (US); Rachael C. Hunter, Princeton, NJ (US); Huizhong Gu, Monmouth Junction, NJ (US); Suresh D. Babu, Plainsboro, NJ (US); Yuefei Shao, Dayton, NJ (US)

(73) Assignee: Pharmacopeia Drug Discovery, Inc., Cranbury, NJ (US)

( * ) Notice: Subject to any disclaimer, the term of this patent is extended or adjusted under 35 U.S.C. 154(b) by 344 days.

(21) Appl. No.: 10/120,080

(22) Filed: Apr. 10, 2002

(65) Prior Publication Data

US 2003/0013720 A1 Jan. 16, 2003

Related U.S. Application Data

(60) Provisional application No. 60/283,523, filed on Apr. 12, 2001.

(51) Int. Cl.[7] ..................... A61K 31/445; C07D 221/26
(52) U.S. Cl. ................. 514/331; 546/229; 546/230
(58) Field of Search .......................... 514/331; 546/229, 546/230

(56) References Cited

U.S. PATENT DOCUMENTS

| 3,455,940 A | | 7/1969 | Stecker ..................... 546/377 |
| 5,908,830 A | * | 6/1999 | Smith et al. ................. 514/12 |
| 6,043,246 A | * | 3/2000 | Fukami et al. ......... 514/253.09 |

FOREIGN PATENT DOCUMENTS

| EP | 428434 A2 | 5/1991 |
| EP | 474561 A1 | 3/1992 |
| EP | 515240 A1 | 11/1992 |
| EP | 559538 A1 | 9/1993 |
| FR | 2717802 A1 | 9/1995 |
| GB | 230714 A | 3/1997 |
| WO | WO 00 06545 | 1/2000 |
| WO | WO 0025786 | 5/2000 |
| WO | WO 00/27845 | 5/2000 |

OTHER PUBLICATIONS

Farbwerke hoeschst "1–methyl–4 . . . " CA 62:51571 (1965).*
Stecker et al. "Germicidal . . . " CA 70:11371 (1969).*
Loyd et al. "Prepart of heterocyclo . . . " CA 139:364829 (2003).*
Silverman "The organic chemistry of . . . " p. xii, chapter 8, table of content (1993).*
Degraw,, "Histamine Releasers", J. Med. Chem. vol. 10, No. 2, 1967, pp. 174–177.
Lucas, "C(4–phenyl–'4!piperidyl)–methylamine", J. Am. Chem. Soc., vol. 69, 1947, p. 2582.
Shimada, et al.,*Nature*, vol. 396(Dec. 17, 1998), pp. 670–673.
Gnecco, D., *Org. Prep. Proceed. Int.*, (1996) 28(4), pp. 478–480.

* cited by examiner

*Primary Examiner*—Celia Chang
(74) *Attorney, Agent, or Firm*—Palaiyur S. Kalyanaraman

(57) ABSTRACT

In one embodiment, this invention provides a novel class of compounds as antagonists of the MCH receptor, methods of preparing such compounds, pharmaceutical compositions containing one or more of the compounds, methods of preparing pharmaceutical formulations comprising one or more such compounds, and methods of treatment, prevention or amelioration or one or more of diseases associated with the MCH receptor. An illustrative inventive compound is shown below:

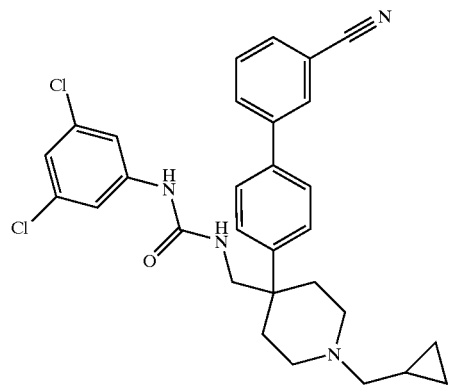

27 Claims, No Drawings

ARYL AND BIARYL PIPERDINES WITH MCH MODULATORY ACTIVITY

This application claims priority from provisional application, Ser. No. 60/283,523 filed Apr. 12, 2001, and the disclosure is related to that in pending provisional patent application, Ser. No. 60/277,534, filed on Mar. 21, 2001.

FIELD OF THE INVENTION

The present invention relates to antagonists for melanin-concentrating hormone (MCH) and their use in the treatment of obesity, diabetes and related disorders. It generally discloses novel compounds having MCH receptor modulatory activity, pharmaceutical compositions containing one or more such modulators, methods of preparing such modulators and methods of using such modulators to treat obesity, diabetes and related disorders. The invention specifically discloses certain novel aryl and biaryl piperidine compounds.

BACKGROUND OF THE INVENTION

MCH, a 19-amino acid cyclic peptide, was first identified over a decade ago in teleost fish where it appears to regulate color change. More recently, MCH which is synthesized mainly in the lateral hypothalamus, a brain center regulating feeding behavior, has been the subject of investigation for its possible role as a regulator of eating behavior in mammals. Central administration of MCH is known to stimulate food intake and promote fat storage in rodents. It is also known that mice that over-express MCH are obese. As reported by Shimada et al., Nature, Vol. 396 (17 Dec. 1998), pp. 670–673, MCH-deficient mice have reduced body weight and leanness due to hypophagia (reduced feeding). In view of their findings, the authors have suggested that antagonists of MCH action may be effective for the treatment of obesity. U.S. Pat. No. 5,908,830 discloses a combination therapy for the treatment of diabetes or obesity involving the administration of a metabolic rate increasing agent and a feeding behavior modifying agent, an example of the latter being an MCH antagonist. U.S. Pat. No. 6,043,246 discloses urea derivatives said to be useful as neuropeptide Y receptor antagonists and as agents for the treatment of, inter alia, diseases of the metabolic system including obesity and diabetes. Published PCT patent application WO 00/27845 describes a class of compounds, characterized therein as spiro-indolines, said to be selective neuropeptide Y Y5 antagonists and useful for the treatment of obesity and the complications associated therewith. Commonly assigned, copending U.S. provisional patent application Ser. No. 60/232,255, filed Sep. 14, 2000, discloses and claims aryl-substituted urea neuropeptide Y Y5 antagonists and their use in the treatment of obesity, hyperphagia (increased feeding) and diabetes.

GB 2304714-A (Assignee: Sanofi) discloses piperidine derivatives of the formula:

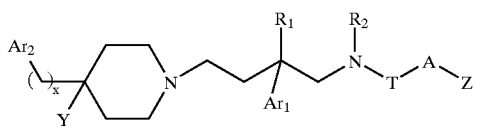

where the various moieties are as defined.

FR 2717802-A1 discloses piperidines of the formula:

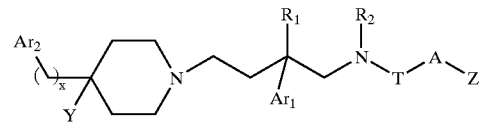

where the various moieties are as defined.

EP 428434-A discloses piperidines and piperazines of the formula:

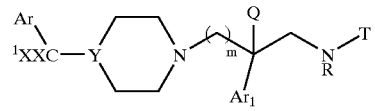

where the various moieties are as defined.

EP 515240-A1 discloses compounds of the formula:

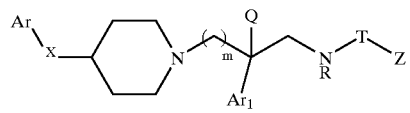

where the various moieties are as defined.

EP 559538-A1 discloses compounds of the formula:

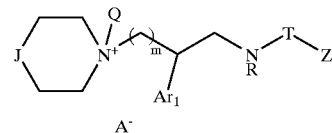

where the various moieties are as defined.

EP 474561-A1 discloses compounds of the formula:

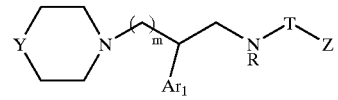

where the various moieties are as defined.

Copending patent application, Ser. No 60/277,534, filed on Mar. 21, 2001, discloses certain novel aryl and biaryl compounds with MCH modulatory activity.

There is a need for new compounds, formulations, treatments and therapies for MCH receptor modulation, diabetes and related disorders. It is, therefore, an object of this invention to provide compounds useful in the treatment or prevention or amelioration of such disorders.

A further object of the present invention is to provide methods for modulating the MCH receptor using the compounds and pharmaceutical compositions provided herein.

Another object herein is to provide methods of modulating MCH receptors using the compounds provided herein.

SUMMARY OF THE INVENTION

In its many embodiments, the present invention provides a novel class of piperidine compounds as antagonists of MCH receptor, methods of preparing such compounds, pharmaceutical compositions containing one or more such compounds, methods of preparing pharmaceutical formulations comprising one or more such compounds, and methods of treatment, prevention or amelioration of one or more of diseases associated with the MCH receptor. In one embodiment, the present application discloses a compound, including enantiomers, stereoisomers, rotamers, tautomers racemates and prodrug of said compound, and pharmaceutically acceptable salts or solvates of said compound or of said prodrug, said compound having the general structure shown in Formula I:

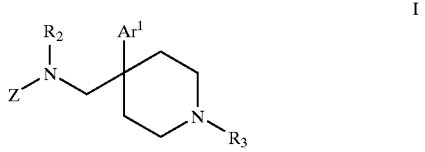

I wherein:
$Ar^1$ is selected from the following moieties:

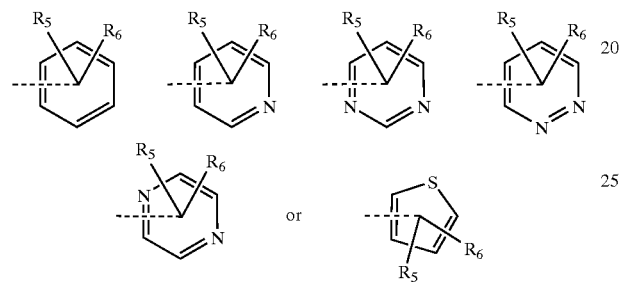

Z is a moiety selected from the group consisting of $R_4CO—$; $R_4SO_2—$; $R_4N(R^{2'})CO—$; $R^{4'}—$; and $R^{4'}—O—C(O)—$;
$R_2$ is H; alkyl; or alkyl (substituted with cycloalkyl);
$R^{2'}$ is H or alkyl;
$R_3$ is a moiety selected from the group consisting of H; alkyl; cycloalkyl; alkyl (substituted with cycloalkyl); alkyl (substituted with alkoxy); alkyl(substituted with $CF_3$); arylalkyl; alkylaryl; tetrahydrofuranyl; tetrahydropyranyl; $R_8SO_2—$;

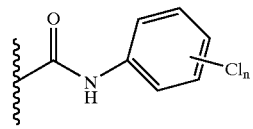

and
n is a number 1 to 5;
$R_4$ is phenyl (substituted with $R_7$) or phenylalkyl (substituted on the phenyl with $R_7$);
$R^{4'}$ is a moiety selected from the group consisting of H; alkyl; cycloalkyl; alkyl (substituted with cycloalkyl); alkyl (substituted with alkoxy); alkyl(substituted with $CF_3$); arylalkyl; alkylaryl; tetrahydrofuranyl; and tetrahydropyranyl;
$R_5$ numbers 1–4 which may be the same or different and are independently selected from the group consisting of $R_7$; phenyl (substituted with $R_7$); pyridyl (substituted with $R_7$); thiophenyl (substituted with $R_7$); pyrimidinyl (substituted with $R_7$); pyridazinyl (substituted with $R_7$); and pyrazinyl (substituted with $R_7$) as well as the N-oxides of the above-noted pyridyl, pyrimidinyl, pyridazinyl and pyrazinyl;
$R_6$ numbers 1–4 which may be the same or different and are independently selected from the group consisting of H; halogen; alkyl; OH; alkoxy; $NH_2$; NH-alkyl; N(alkyl)$_2$; CN; $CF_3$; $NO_2$; and $CF_3O$;

$R_7$ numbers 1–3 which may be the same or different and are independently selected from the group consisting of H; halogen; alkyl; OH; alkoxy; $NH_2$, NH-alkyl; N(alkyl)$_2$; CN; $CF_3$; $NO_2$; $CF_3O$; —NH—C(O)-alkyl; —CH(O); -methylenedioxy; —$CH_2OH$; benzofuran-2-yl; —O(alkyl); —C(O)alkyl; and indolyl; and
$R_8$ is selected from the group consisting of alkyl; arylalkyl; alkylaryl; aryl; —NH(alkyl); and —N(alkyl)$_2$.

Also included in the invention is a compound of Formula I where $R_2$ and Z (or part of Z) are joined to form a cyclic ring such as, for example, the compound:

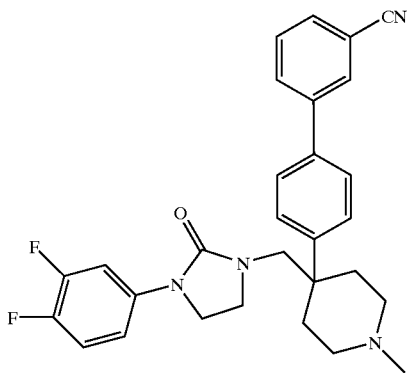

In another embodiment, the present application discloses a compound, including enantiomers, stereoisomers, rotamers, tautomers, racemates and prodrug of said compound, and pharmaceutically acceptable salts or solvates of said compound or of said prodrug, said compound having the general structure shown in Formula II:

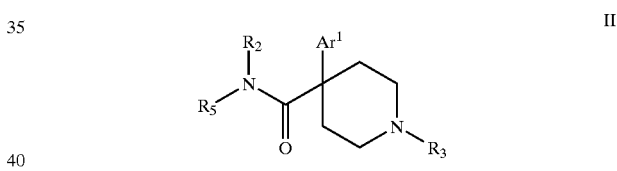

II where $Ar^1$ and $R_2$–$R_8$ are defined as above.
In yet another embodiment, the present application discloses a compound, including enantiomers, stereoisomers, rotamers, tautomers racemates and prodrug of said compound, and pharmaceutically acceptable salts or solvates of said compound or of said prodrug, said compound having the general structure shown in Formula III:

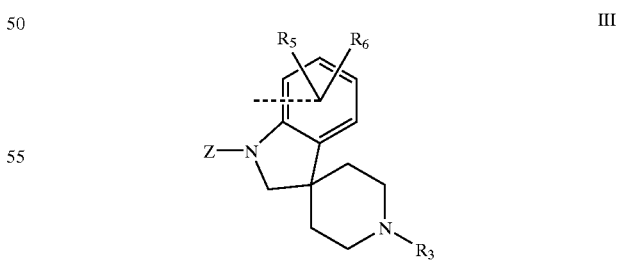

III where $R_3$, $R_5$, $R_6$, and Z are defined as above.
The ring moieties in the inventive compounds may optionally carry substituents or additional substituents on the ring. Such substituents may be, for example, alkyl, cycloalkyl, halogen, alkoxy, aryloxy, arylalkoxy, alkylaryloxy, hydroxy, carboxy, carboalkoxy, cyano, trifluoroalkyl, nitro and the like.

Also included in the invention are tautomers, rotamers, enantiomers and other optical isomers of compounds of Formula I, Formula II and Formula III where applicable, pharmaceutically acceptable salts, solvates and derivatives thereof, as well as prodrug of said compounds, and pharmaceutically acceptable salts, solvates and derivatives of said prodrug.

A further feature of the invention is pharmaceutical compositions containing as active ingredient a compound of Formula I, Formula II or Formula III (or its salt, solvate or isomers) together with a pharmaceutically acceptable carrier or excipient.

The invention also provides methods for preparing compounds of Formula I, Formula II and Formula III, as well as methods for treating diseases such as, for example, obesity and related disorders. The methods for treating comprise administering to a patient suffering from said disease or diseases therapeutically effective amounts of a compound of Formula I, Formula II or Formula III, or of pharmaceutical compositions comprising a compound of Formula I, Formula II or Formula III. The term "Therapeutically effective amounts" refers to amounts of the compound that are effective to make the compound function as MCH modulator.

Also disclosed is the use of a compound of Formula I, Formula II or of Formula III for the manufacture of a medicament for treating obesity and related disorders.

DETAILED DESCRIPTION OF PREFERRED EMBODIMENTS

In one embodiment, the present invention discloses compounds of Formula I, Formula II or Formula III, or a pharmaceutically acceptable derivative thereof, as inhibitors of MCH receptor. The various definitions for the moieties in Formulas I, II and III are given above.

The preferred definitions for compounds belonging to Formula I are represented below:

For $Ar^1$: phenyl (substituted with $R_5$) and pyridyl (substituted with $R_5$), with the more preferred being phenyl (substituted with $R_5$ in the 4-position with respect to the attachment of Ar1 to the benzylic position shown in Formula I).

For Z: $R_4N(R^{2'})CO$—, with the above-noted definitions.

For $R_2$ and $R^{2'}$: H

For $R_3$: alkyl, cycloalkyl, tetrahydrofuranyl or tetrahydropyranyl.

For $R_4$: phenyl (substituted with $R_7$).

For $R_5$: phenyl (substituted with $R_7$) or pyridyl (substituted with $R_7$).

Especially preferred for $R_5$ are phenyl substituted with $R_7$ in its 3-position, such as, for example, 3-cyanophenyl, 3-chlorophenyl and 3-pyridyl.

For $R_7$: halogen, CN; $CF_3$; $NO_2$; and methylenedioxy.

A preferred structure belonging to Formula I is represented below:

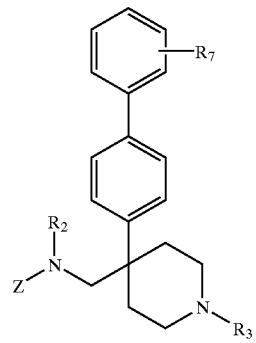

where the various preferred moieties are defined above.

Unless defined otherwise, all technical and scientific terms used herein have the same meaning as is commonly understood by one of skill in the art to which this invention belongs. Thus, for example, the term alkyl (including the alkyl portions of alkoxy) refers to a monovalent group derived from a straight or branched chain saturated hydrocarbon by the removal of a single atom having from 1 to 8 carbon atoms, preferably from 1 to 6;

aryl—represents a carbocyclic group having from 6 to 14 carbon atoms and having at least one benzenoid ring, with all available substitutable aromatic carbon atoms of the carbocyclic group being intended as possible points of attachment. Preferred aryl groups include phenyl, 1-naphthyl, 2-naphthyl and indanyl, and especially phenyl and substituted phenyl;

aralkyl—represents a moiety containing an aryl group linked vial a lower alkyl;

alkylaryl—represents a moiety containing a lower alkyl linked via an aryl group;

cycloalkyl—represents a saturated carbocyclic ring having from 3 to 8 carbon atoms, preferably 5 or 6, optionally substituted.

heterocyclic—represents, in addition to the heteroaryl groups defined below, saturated and unsaturated cyclic organic groups having at least one O, S and/or N atom interrupting a carbocyclic ring structure that consists of one ring or two fused rings, wherein each ring is 5-, 6- or 7-membered and may or may not have double bonds that lack delocalized pi electrons, which ring structure has from 2 to 8, preferably from 3 to 6 carbon atoms, e.g., 2- or 3-piperidinyl, 2- or 3-piperazinyl, 2- or 3-morpholinyl, or 2- or 3-thiomorpholinyl;

halogen—represents fluorine, chlorine, bromine and iodine;

heteroaryl—represents a cyclic organic group having at least one O, S and/or N atom interrupting a carbocyclic ring structure and having a sufficient number of delocalized pi electrons to provide aromatic character, with the aromatic heterocyclyl group having from 2 to 14, preferably 4 or 5 carbon atoms, e.g., 2-, 3- or 4-pyridyl, 2- or 3-furyl, 2- or 3-thienyl, 2-, 4- or 5-thiazolyl, 2- or 4-imidazolyl, 2-, 4- or 5-pyrimidinyl, 2-pyrazinyl, or 3- or 4-pyridazinyl, etc.

As used herein, "prodrug" means compounds that are drug precursors which, following administration to a patient, release the drug in vivo via some chemical or physiological process (e.g., a prodrug on being brought to the physiological pH or through enzyme action is converted to the desired drug form).

Representative compounds of the invention which exhibit excellent MCH receptor modulatory activity are listed in Table I along with their activity (ranges of $K_i$ values in nanomolar, nM).

Depending upon the structure, the compounds of the invention may form pharmaceutically acceptable salts with organic or inorganic acids, or organic or inorganic bases. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. For formation of salts with bases, suitable bases are, for example, NaOH, KOH, $NH_4OH$, tetraalkylammonium hydroxide, and the like.

In another embodiment, this invention provides pharmaceutical compositions comprising the above-described inventive aryl or biaryl compounds as an active ingredient. The pharmaceutical compositions generally additionally comprise a pharmaceutically acceptable carrier diluent, excipient or carrier (collectively referred to herein as carrier materials). Because of their MCH inhibitory activity, such pharmaceutical compositions possess utility in treating obesity and related disorders.

In yet another embodiment, the present invention discloses methods for preparing pharmaceutical compositions comprising the inventive aryl or biaryl compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. MCH inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

The compounds as well as the pharmaceutical formulations containing the inventive compounds may also be delivered subcutaneously.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the pharmaceutical compositions disclosed above for treatment of diseases such as, for example, obesity and the like. The method comprises administering a therapeutically effective amount of the inventive pharmaceutical composition to a patient having such a disease or diseases and in need of such a treatment.

As stated earlier, the invention also includes tautomers, enantiomers and other stereoisomers of the compounds where applicable. Thus, as one skilled in the art knows, some of the inventive compounds may exist in isomeric forms. Such variations are contemplated to be within the scope of the invention.

In addition to monotherapies including the compound represented by Formula I, Formula II or Formula III, another aspect of this invention is combinations (such as, for example, dual combination therapy, three combination therapy and the like,) of therapeutically effective amounts of a compound of Formula I (or Formula II or Formula III), or a prodrug thereof, or a pharmaceutically acceptable salt of said compound or a pharmaceutically acceptable salt of said prodrug, and therapeutically effective amounts of one or more antiobesity/anorectic agent such as, for example, a $\beta_3$ agonist, a thyromimetic agent, or an NPY antagonist.

Still another aspect of this invention is a method for treating obesity comprising administering to a mammal (which term includes humans) in need of such treatment:

a. therapeutically effective amounts of a first compound, said first compound being a Formula I compound (or a Formula II compound or a Formula III compound), a prodrug thereof, or a pharmaceutically acceptable salt of said compound or a pharmaceutically acceptable salt of said prodrug; and b. therapeutically effective amounts of a second compound, said second compound being an antiobesity and/or anorectic agent such as, for example, a $\beta_3$ agonist, a thyromimetic agent, or an NPY antagonist, wherein the amounts of the first and second compounds result in the desired therapeutic effect of treating obesity.

This invention is also directed to a pharmaceutical composition comprising a combination of therapeutically effective amounts of a first compound, said first compound being a Formula I compound (or a Formula II compound or a Formula III compound), a prodrug thereof, or a pharmaceutically acceptable salt of said compound or a pharmaceutically acceptable salt of said prodrug; and therapeutically effective amounts of a second compound, said second compound being an antiobesity and/or anorectic agent such as, for example, a $\beta_3$ agonist, a thyromimetic agent, or an NPY antagonist; and/or optionally a pharmaceutical acceptable carrier, vehicle or diluent.

Another aspect of this invention is a kit comprising:

a. therapeutically effective amounts of a first compound, said first compound being a Formula I compound (or a Formula II compound or a Formula III compound), a prodrug thereof, or a pharmaceutically acceptable salt of said compound or a pharmaceutically acceptable salt of said prodrug; and a pharmaceutically acceptable carrier, vehicle or diluent in a first unit dosage form;

b. therapeutically effective amounts of a second compound, said second compound being an antiobesity and/or anorectic agent such as, for example, a $\beta_3$ agonist, a thyromimetic agent, or an NPY antagonist; and a pharmaceutically acceptable carrier, vehicle or diluent in a second unit dosage form; and c. means for containing said first unit dosage form and said second unit dosage form, wherein the amounts of the first compound and of the second compound result in the desired therapeutic effect of treating obesity.

Illustrative non-limiting examples of preferred antiobesity and/or anorectic agents in the above combination methods, combination compositions and combination kits include: phenylpropanolamine, ephedrine, pseudoephedrine, phentermine, a cholecystokinin-A (hereinafter referred to as CCK-A) agonist, a monoamine reuptake inhibitor (such as, for example, sibutramine), a sympathomimetic agent, a serotonergic agent (such as, for example, dexfenfluramine or fenfluramine), a dopamine agonist (such as, for example, bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as, for example, Exendin and ciliary neurotrophic factors such as, for example, Axokine.

Another aspect of this invention is a method for treating diabetes comprising administering to a mammal:

a. therapeutically effective amounts of a first compound, said first compound being a Formula I compound (or a Formula II compound or a Formula III compound), a prodrug thereof, or a pharmaceutically acceptable salt of said compound or a pharmaceutically acceptable salt of said prodrug; and b. therapeutically effective amounts of a second compound, said second compound being an aldose reductase inhibitor, a glycogen phosphorylase inhibitor, a sorbitol dehydrogenase inhibitor, a protein tyrosine phosphatase 1 B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in the therapeutic effect of treating diabetes.

This invention is also directed to a pharmaceutical composition comprising a combination of therapeutically effective amounts of a first compound, said first compound being a Formula I compound (or a Formula II compound or a Formula III compound), a prodrug thereof, or a pharmaceutically acceptable salt of said compound or a pharmaceutically acceptable salt of said prodrug; therapeutically effective amounts of a second compound, said second compound being an aldose reductase inhibitor, a glycogen phosphorylase inhibitor, a sorbitol dehydrogenase inhibitor, a protein tyrosine phosphatase 1 B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally a pharmaceutically acceptable carrier, vehicle or diluent.

Another aspect of this invention is a kit comprising:

a. therapeutically effective amounts of a first compound, said first compound being a Formula I compound (or a Formula II compound or a Formula III compound), a prodrug thereof, or a pharmaceutically acceptable salt of said compound or a pharmaceutically acceptable salt of said prodrug; and a pharmaceutically acceptable carrier, vehicle or diluent in a first unit dosage form;

b. therapeutically effective amounts of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and a pharmaceutically acceptable carrier, vehicle or diluent in a second unit dosage form; and c. means for containing said first unit dosage form and said second unit dosage form, wherein the amounts of the first compound and of the second compound result in the desired therapeutic effect of treating diabetes.

Another embodiment of the invention discloses a method of making the inventive aryl or biaryl compounds disclosed herein. The compounds may be prepared by several techniques known in the art. Representative illustrative procedures are outlined in the following reaction schemes.

Abbreviations which are used in the descriptions of the schemes, preparations and the examples that follow are:

Abbreviation Used:
Ar=argon
Boc=tert-butyloxycarbonyl
tBuOH=tert-butanol
$CH_2Cl_2$=dichloromethane
$ClCH_2CH_2Cl$=1,2-dichloroethane
CDl=carbonyldiimidazole
DIC=1,3-dicyclohexylcarbodiimide
DMF N,N-dimethylformamide
DIEA=N,N-diisopropylethylamine
Et=ethyl
EtOH=ethanol
EtOAc=ethyl acetate
HOBt=1-hydroxybenzotriazole
$H_2SO_4$=sulfuric acid
HCl=hydrogen chloride
$H_2O$=water
$K_2CO_3$=potassium carbonate
LDA=lithium diisopropylamide
LiOH=lithium hydroxide
$LiAlH_4$=lithium aluminum hydride
Me=methyl
MeI=methyl iodide
MeOH=methanol
$Me_2S$=dimethylsulfide
NMMO=4-methylmorpholine N-oxide
$Na(OAc)_3BH$=sodium triacetoxyborohydride
NaCl=sodium chloride
NaH=sodium hydride
$NaHCO_3$=sodium bicarbonate
$NaIO_4$=sodium periodate
$Na_2CO_3$=sodium carbonate
NaOH=sodium hydroxide
$Na_2SO_4$=sodium sulfate Na₂S₂O₃=sodium thiosulfate
O₃=ozone
O₂=oxygen
OsO₄=osmium tetroxide
Pd(PPh₃)₄=tetrakis(triphenylphosphine)palladium(0)
SOCl₂=thionyl chloride
TEA=triethylamine
TFA=trifluoroacetic acid
TMSOTf=trimethylsilyl trifluoromethanesulfonate
THF=tetrahydrofuran
TFAA=trifluroacetic anhydride
HMCHR-CHO=membranes prepared from Chinese hamster ovary cells that overexpress human melanin concentrating hormone.
WGA-SPA beads=Scintillation Assay beads labeled with wheat germ agglutinin
BSA=bovine serum albumin
MCH=melanin concentrating hormone
MCHR=melanin concentrating hormone receptor Several methods for preparing the compounds of this invention and intermediates thereof are illustrated in the following reaction schemes. Starting materials are made using known procedures or as illustrated.

REACTION SCHEMES

Several methods for preparing the compounds of this invention and intermediates thereof are illustrated in the following reaction schemes. Starting materials are made from known procedures or as illustrated.

Reaction Scheme 1 illustrates the synthesis of a key scaffold, 4-aminomethyl-4-(4-iodo-phenyl)-piperidine-1-carboxylic acid tert-butyl ester.

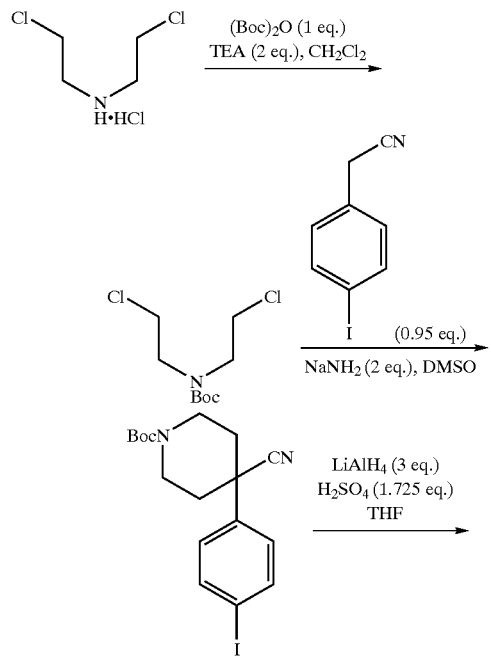

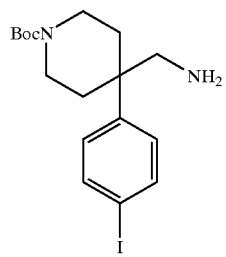

The synthesis starts with the Boc-protection of bis(2-chloroethyl)amine followed by treatment with 4-iodophenylacetonitrile and NaNH₂ in DMSO to give the nitrile intermediate 4-cyano-4-(4-iodo-phenyl)-piperidine-1-carboxylic acid tert-butyl ester. Reduction of the nitrile group using LiAlH₄/H₂SO₄ in THF yielded the desired primary amine scaffold.

Scheme 2 shows the method for the preparation of 1-alkyl-4-(4-iodo-phenyl)-piperidin-4-ylmethylamine scaffolds.

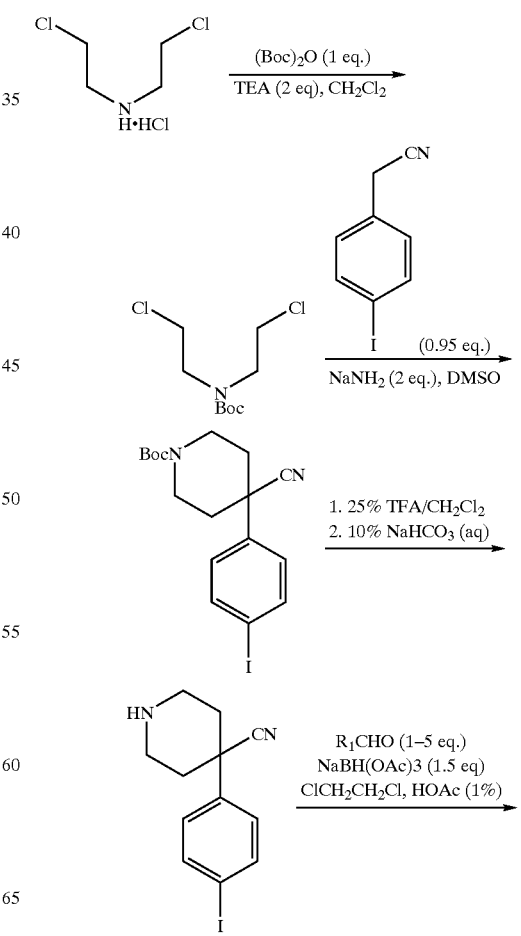

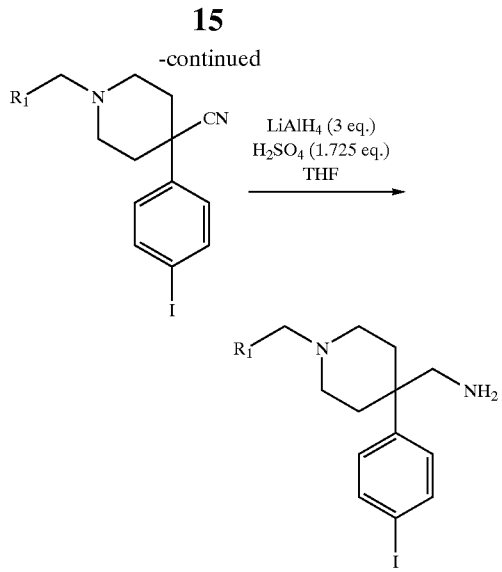

The intermediate 4-cyano-4-(4-iodo-phenyl)-piperidine-1-carboxylic acid tert-butyl ester was treated with TFA to remove the Boc-protecting group. Reductive amination of the piperidine with an aldehyde provides the 1-alkyl-4-(4-iodo-phenyl)-piperidine-4-carbonitrile intermediate, which can be reduced using LiAlH$_4$/H$_2$SO$_4$ in THF to give the desired primary scaffold.

Alternatively, the N-methyl scaffold, 4-(4-Iodo-phenyl)-1-methyl-piperidin-4-yl-methylamine, can be prepared according to Scheme 3.

Scheme 3

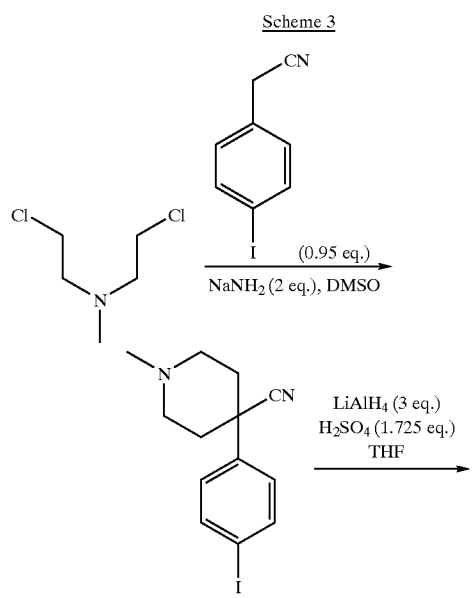

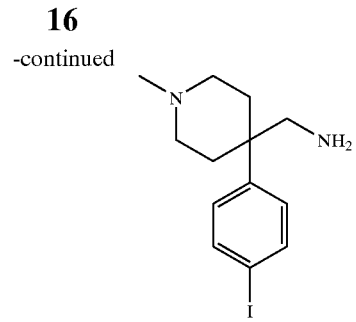

The synthesis starts with the cyclization of commercially available bis(2-chloroethyl)-methylamine with 4-iodophenylacetonitrile followed by LiAlH$_4$/H$_2$SO$_4$ reduction to provide the desired primary amine scaffold.

Scheme 4 illustrates the synthesis method for a carboxylic acid scaffold.

Scheme 4

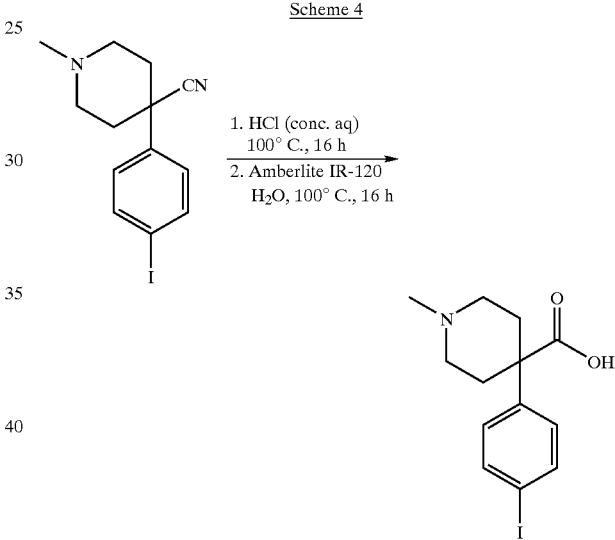

Thus, hydrolysis of 4-(4-iodo-phenyl)-1-methyl-piperidine-4-carbonitrile by heating in concentrated aqueous HCl followed by heating with acid resin Amberlite IR-120 affords the desired carboxylic acid scaffold 4-(4-iodo-phenyl)-1-methyl-piperidine-4-carboxylic acid.

Scheme 5 outlines a general method for preparing compounds of formula I of the invention using a novel solid phase synthesis method.

Scheme 5

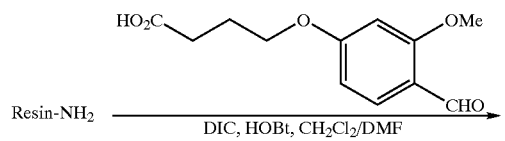

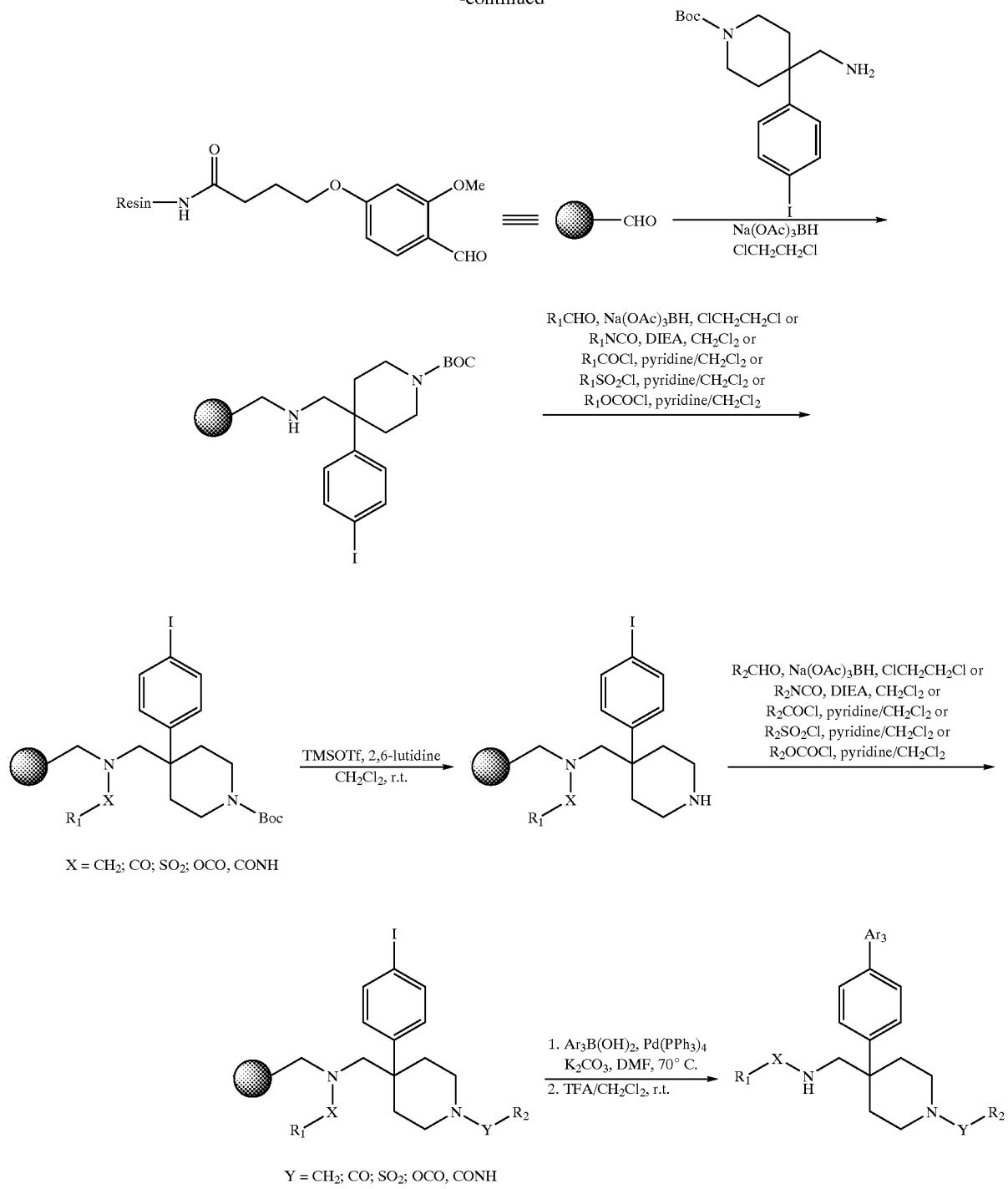

The synthesis begins with a suitable linker, as illustrated using an acid cleavable linker 4-(4-formyl-3-methoxyphenoxy)-butyric acid, to a suitable amino resin through amide bond formation. Reductive amination of the linker aldehyde with the primary amine scaffold 4-aminomethyl-4-(4-iodo-phenyl)-piperidine-1-carboxylic acid tert-butyl ester forms a resin-bound secondary amine. The secondary amine may be treated with a variety of agents such as an aryl or alkyl aldehyde (reductive amination), isocyanate, acid chloride, sulfonyl chloride or chloroformate to form the resin bound tertiary amine, urea, amide, sulfonamide, or carbamate intermediate, respectively. This intermediate may then be treated with TMSOTf/2,6-lutidine to remove the Boc-protecting group. The resulting piperidine amine may be treated with a variety of agents such as an aryl or alkyl aldehyde (reductive amination), isocyanate, acid chloride, sulfonyl chloride or chloroformate to form the resin bound tertiary amine, urea, amide, sulfonamide, or carbamate intermediate, respectively. Suzuki coupling of the iodophenyl compound with a variety of arylboronic acids followed by TFA mediated cleavage provides the biaryl piperidine compounds of formula I of the invention.

19

Scheme 6

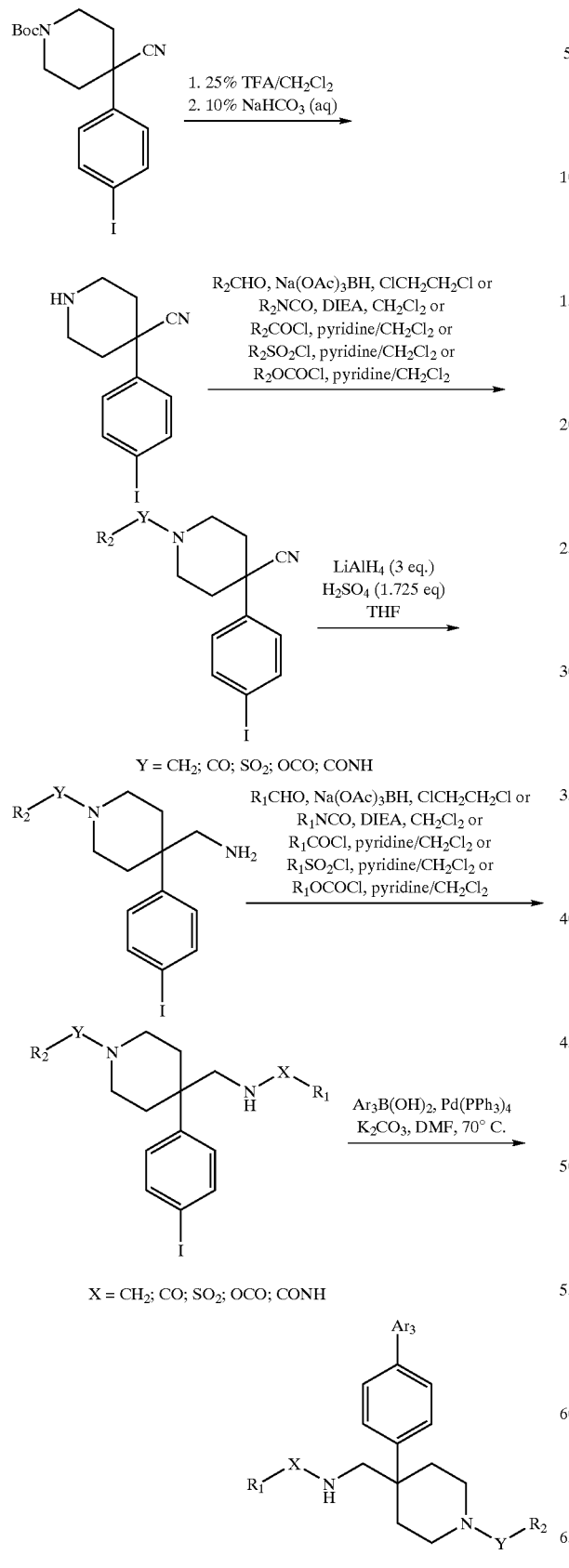

20

Alternatively, compounds of formula I of the invention may also be prepared using a solution phase method as outlined in Scheme 6. As shown in the scheme, the synthesis begins with Boc-removal from the scaffold 4-cyano-4-(4-iodo-phenyl)-piperidine-1-carboxylic acid tert-butyl ester. The aryl piperidine intermediate was then treated with a variety of agents such as an aryl or alkyl aldehyde (reductive amination), isocyanate, acid chloride, sulfonyl chloride or chloroformate to form the resin bound tertiary amine, urea, amide, sulfonamide, or carbamate intermediate, respectively. Reduction of the nitrile group using $LiAlH_4/H_2SO_4$ followed by treatment with a variety of agents such as an aryl or alkyl aldehyde (reductive amination), isocyanate, acid chloride, sulfonyl chloride or chloroformate to form the resin bound tertiary amine, urea, amide, sulfonamide, or carbamate intermediate, respectively. Suzuki coupling of the iodophenyl intermediate with a variety of arylboronic acids provide the biaryl piperidine compounds of formula I of the invention.

Scheme 7 outlines a method for preparing cyclic urea (imidazolidinone) compounds of the invention.

Scheme 7

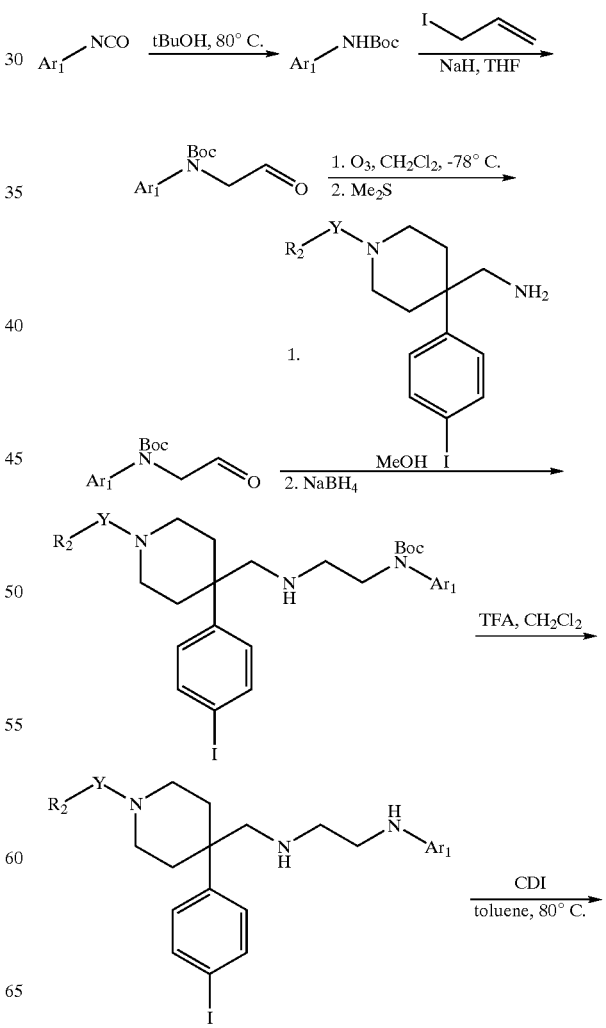

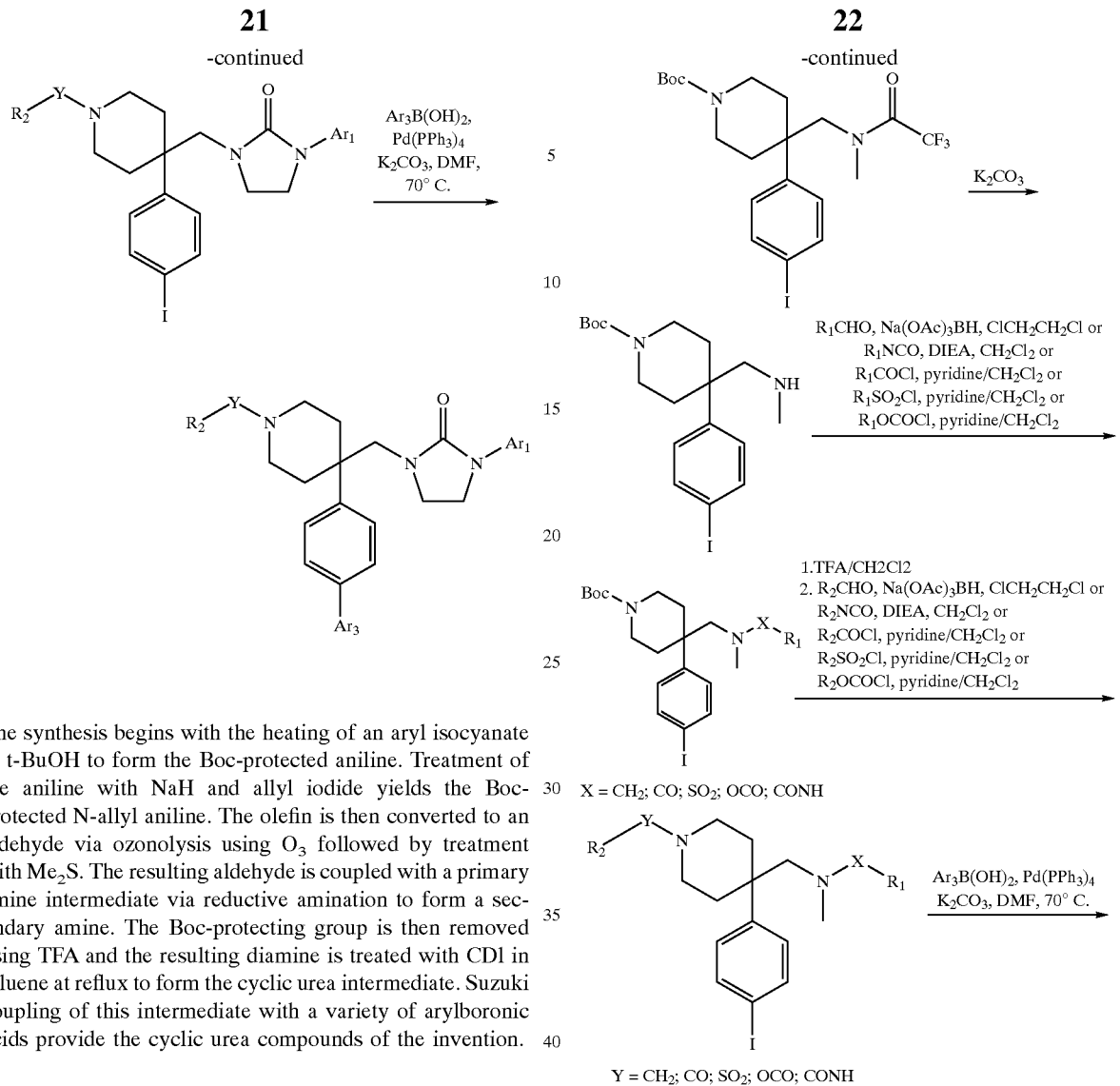

The synthesis begins with the heating of an aryl isocyanate in t-BuOH to form the Boc-protected aniline. Treatment of the aniline with NaH and allyl iodide yields the Boc-protected N-allyl aniline. The olefin is then converted to an aldehyde via ozonolysis using O₃ followed by treatment with Me₂S. The resulting aldehyde is coupled with a primary amine intermediate via reductive amination to form a secondary amine. The Boc-protecting group is then removed using TFA and the resulting diamine is treated with CDI in toluene at reflux to form the cyclic urea intermediate. Suzuki coupling of this intermediate with a variety of arylboronic acids provide the cyclic urea compounds of the invention.

Scheme 8 summarizes a method for preparing N-methyl substituted urea compounds of formula I of the invention.

Scheme 8

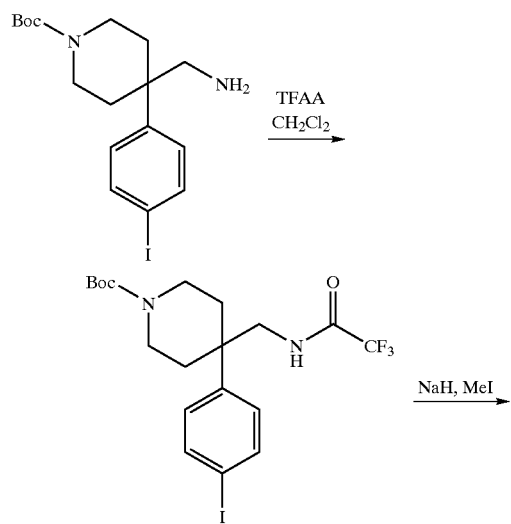

The synthesis begins with the treatment of the primary amine scaffold 4-aminomethyl-4-(4-iodo-phenyl)-piperidine-1-carboxylic acid tert-butyl ester with TFAA to form the trifluoroacetamide. Reaction of the trifluoroacetamide with MeI/NaH followed by deprotection of the trifluoroacetyl group gives the secondary N—Me amine.

The amine may be treated with a variety of agents such as an aryl or alkyl aldehyde (reductive amination), isocyanate, acid chloride, sulfonyl chloride or chloroformate to form the resin bound tertiary amine, urea, amide, sulfonamide, or carbamate intermediate, respectively. Removal of the Boc-protecting group using TFA followed by a second treatment with a variety of agents such as an aryl or alkyl aldehyde (reductive amination), isocyanate, acid chloride, sulfonyl chloride or chloroformate to form the resin bound tertiary amine, urea, amide, sulfonamide, or carbamate intermediate, respectively. Suzuki coupling of the iodophenyl compound with a variety of arylboronic acids gives the N-methyl compounds of formula I of the invention.

Scheme 9 outlines a general method for the synthesis of compounds of formula II of the invention.

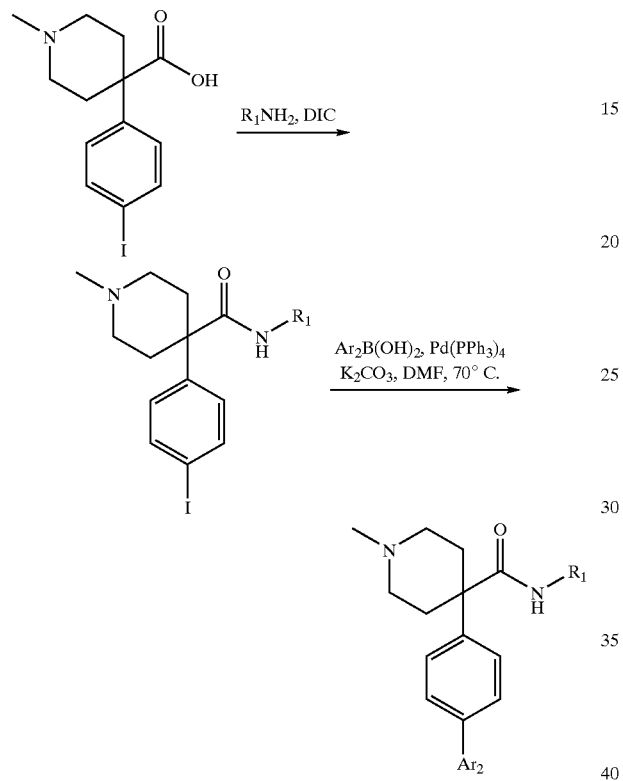

The synthesis starts with DIC mediated amide bond formation between a primary amine or aniline with the carboxylic acid scaffold 4-(4-iodo-phenyl)-1-methyl-piperidine-4-carboxylic acid. The intermediate is coupled with a variety of arylboronic acids under Suzuki conditions to provide the biaryl compounds of formula II of the invention.

Scheme 10 shows the method for preparing the spiroindoline compounds of formula III of the invention. The synthesis begins with the conversion of isonipecotic acid to 1-Cbz-piperidine-4-carboxaldehyde via a three step reaction: Cbz protection followed by methyl ester formation and then DIBAL-H reduction yields an aldehyde which is then treated with a bromo- or iodo-phenylhydrazine and TFA in DCM to form the tricyclic spiroindoline intermediate. Treatment of the intermediate with a variety of agents such as an aryl or alkyl aldehyde (reductive amination), isocyanate, acid chloride, sulfonyl chloride or chloroformate to form the resin bound tertiary amine, urea, amide, sulfonamide, or carbamate intermediate, respectively. Removal of the Cbz-protecting group by hydrogenation followed by treatment with a variety of agents such as an aryl or alkyl aldehyde (reductive amination), isocyanate, acid chloride, sulfonyl chloride or chloroformate to form the resin bound tertiary amine, urea, amide, sulfonamide, or carbamate intermediate, respectively. Suzuki coupling of the compound with a variety of arylboronic acids provides the biaryl spiroindoline compounds of formula III of the invention.

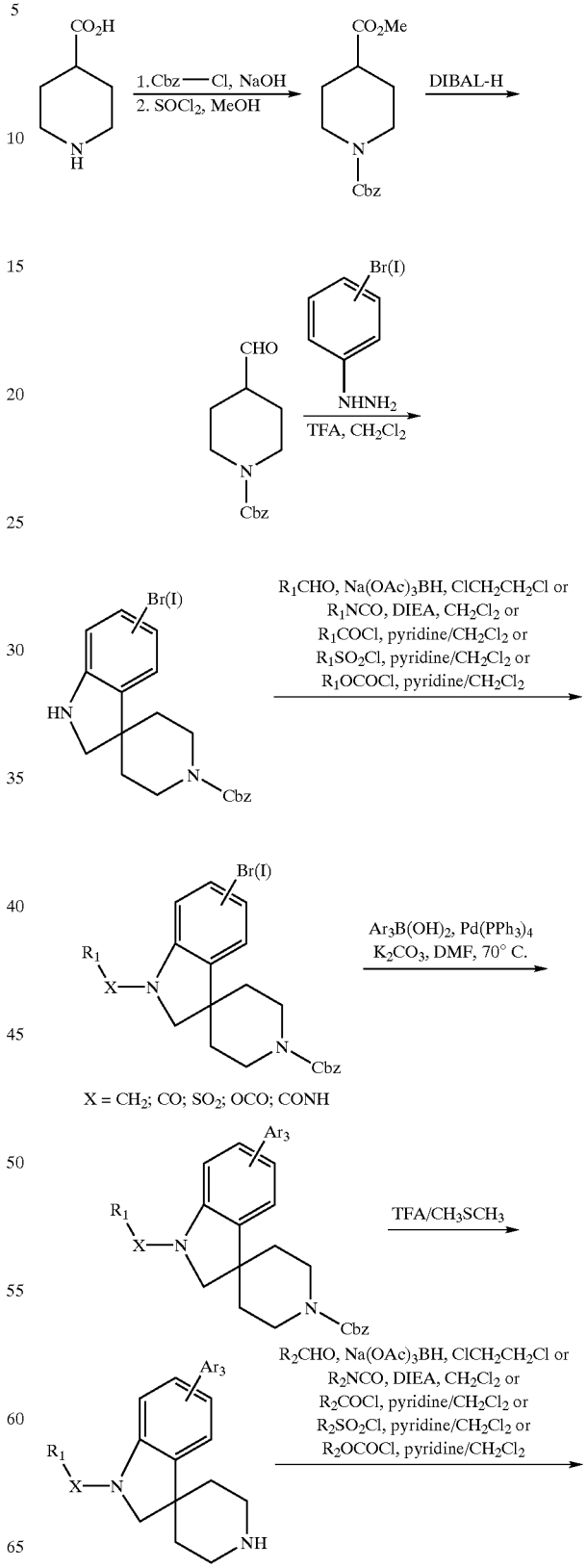

-continued

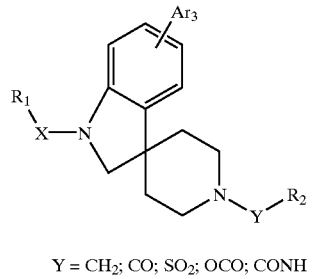

Y = CH₂; CO; SO₂; OCO; CONH

The following examples are provided for the purpose of further illustration only and are not intended to be limitations on the disclosed invention.

EXAMPLE 1

4-Aminomethyl-4-(4-iodo-phenyl)-piperidine-1-carboxylic acid tert-butyl ester

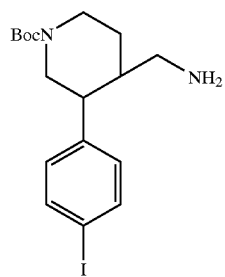

To a solution of bis-(2-chloro-ethyl)amine hydrochloride (50 g, 280 mmol) in $CH_2Cl_2$ (400 mL) was added $(Boc)_2O$ (61.14 g, 280 mmol). The mixture was cooled to 0° C. and TEA (78 mL, 256 mmol, 2 eq.) was added in 5 portions. The resulting thick slurry was diluted with $CH_2Cl_2$ (100 mL) then stirred and warmed to room temperature for 4 h. The mixture was filtered and the solids were washed with hexane. The filtrate was concentrated by rotary evaporation and the resulting slurry was purified by flash column chromatography by eluting with 30% $CH_2Cl_2$/hexanes to afford bis-(2-chloro-ethyl)-carbamic acid tert-butyl ester as a clear oil (28 g, 42%). $^1$H NMR (300 MHz, CDCl₃): δ3.72 (br. m, 8H), 1.58 (s, 9H).

To a solution of 4-iodophenylacetonitrile (6.88 g, 28.3 mmol, 1 eq.) and bis-(2-chloro-ethyl)-carbamic acid tert-butyl ester (7.2 g, 30 mmol, 1.05 eq.) in DMSO (100 mL) under argon (Ar) was added $NaNH_2$ (2.46 g, 60 mmol, 2 eq.) in portions over 15 min. The reaction was stirred at room temperature for 0.5 h, then poured onto ice (200 g), diluted with EtOAc (250 mL) and stirred for 1 h. The organic layer was separated and the aqueous layer was washed repeatedly with EtOAc until colorless. The combined organic extracts were dried over anhydrous $Na_2SO_4$, filtered and concentrated by rotary evaporation to afford an orange oil which was purified by flash column chromatography by eluting with 7–12% EtOAc/hexanes to yield 4-cyano-4-(4-iodo-phenyl)-piperidine-1-carboxylic acid tert-butyl ester as a pale orange oil/solid (8.28 g, 18.96 mmol, 67%). $^1$H NMR (300 MHz, CDCl₃): δ 7.82 (dd, 2H), 7.26 (dd, 2H), 4.38 (br. s, 2H), 4.28 (br. t, 2H), 2.15 (m, 2H), 2.0 (td, 2H), 1.59 (s, 9H). (Ref.: D. Gnecco et al, *Org. Prep. Proceed. Int.*, (1996) 28 (4), 478–480.

A solution of $LiAlH_4$ (8.5 mL of a 1.0M solution in THF, 8.5 mmol, 3.5 eq.) was cooled to 0° C. and concentrated $H_2SO_4$ (0.43 mL, 7.6 mmol, 3.2 eq.) was added in a drop-wise fashion. The resulting white slurry was stirred at room temperature for 0.5 h, then heated to 30° C. for 0.5 h. The reaction was cooled to room temperature and a solution of 4-cyano-4-(4-iodo-phenyl)-piperidine-1-carboxylic acid tert-butyl ester (1 g, 2.43 mmol, 1 eq.) in THF (3 mL) was added over 0.25 h. The mixture was heated to 55° C. and monitored by TLC. After 5 h the reaction was cooled to room temperature and quenched by careful addition of $H_2O$ (0.323 mL), 1N NaOH (0.646 mL) and $H_2O$ (0.97 mL). This mixture was diluted with $CH_2Cl_2$ (25 mL) and stirred vigorously for 1 h and then filtered through a pad of celite®. The salts were washed with $CH_2Cl_2$ (5×25 mL) and the combined washings were concentrated by rotary evaporation to give the crude product as a yellow solid (0.597 g) which was purified by flash column chromatography by eluting with 1% MeOH/1% TEA/$CH_2Cl_2$ to give the title compound 4-aminomethyl-4-(4-iodo-phenyl)-piperidine-1-carboxylic acid tert-butyl ester (0.26 g, 0.625 mmol, 26%) as a colorless oil. $^1$H NMR (CDCl₃): δ 7.81 (d, 2H), 7.17 (d, 2H), 3.82 (m, 2H), 3.145 (m, 2H), 2.86 (s, 2H), 2.24 (m, 2H), 1.80 (m, 2H), 1.65 (br. m., 2H), 1.56 (s, 9H).

EXAMPLE 2

[4-(4-Iodo-phenyl)-1-methyl-piperidin-4-yl]-methylamine

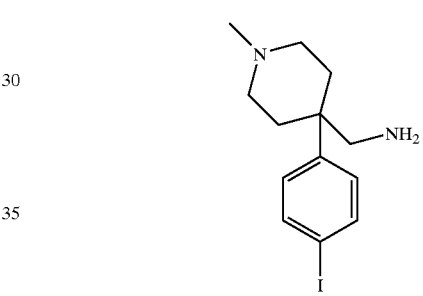

To a stirred solution of 4-cyano-4-(4-iodo-phenyl)-piperidine-1-carboxylic acid tert-butyl ester (1.95 g, 4.73 mmol) in $CH_2Cl_2$ (37.5 mL) at 0° C. was added TFA (12.5 mL). The mixture was stirred at room temperature for 3 h. TLC (4:1 hexanes/EtOAc) showed no starting material left. The solvent was removed by rotary evaporation and the resulting liquid was evaporated from toluene (2×20 mL), diluted with EtOAc (100 mL) and washed with 10% aqueous $NaHCO_3$ (2×50 mL) and saturated brine (50 mL). The organic layer was dried over anhydrous $Na_2SO_4$, filtered and concentrated by rotary evaporation, dried under high vacuum for 1 h to yield 4-(4-iodo-phenyl)-piperidine-4-carbonitrile as a reddish solid (1.46 g, ~4.7 mmol, ~100%). $^1$H NMR (300 MHz, CDCl₃): δ 7.82 (dd, 2H), 7.37 (dd, 2H), 3.25 (m, 4H), 2.15 (m, 4H).

To a solution of the crude 4-(4-iodo-phenyl)-piperidine-4-carbonitrile (~4.7 mmol) in $ClCH_2CH_2Cl$ (100 mL) was added formaldehyde (1.92 mL of a 37% solution in $H_2O$, 23.65 mmol, 5 eq.) and HOAc (1 mL, 1% v/v). The mixture was stirred for 0.5 h at room temperature and then $NaBH(OAc)_3$ (1.48 g, 7 mmol, 1.5 eq.) was added. The reaction mixture was stirred for 16 h and then quenched by the addition of saturated aqueous $NaHCO_3$ solution (50 mL). The resulting mixture was extracted with EtOAc (200 mL) and the organic layer was washed with saturated aqueous $NaHCO_3$ solution (50 mL) and saturated brine (100 mL). The organic layer was dried over anhydrous $Na_2SO_4$, filtered and concentrated by rotary evaporation to give the crude 4-(4-iodo-phenyl)-1-methyl-piperidine-4-carbonitrile (1.5 g, 97%) as a brown oil. ¹H NMR (300 MHz, CDCl₃): δ 7.84 (dd, 2H), 7.36 (dd, 2H), 3.08 (dt, 2H), 2.60 (m, 2H), 2.50 (s, 3H), 2.20 (m, 4H).

A solution of LiAlH₄ (1 M in THF, 13.8 mL, 13.8 mmol, 3 eq.) in THF (15 mL) was cooled to 0° C. under Ar. H₂SO₄ (95%, 0.44 mL, 7.95 mmol, 1.725 eq.) was added in a drop-wise fashion over 10 min. The mixture was stirred at room temperature for 2 h, then a solution of 4-(4-iodo-phenyl)-1-methyl-piperidine-4-carbonitrile (~1.5 g, 4.7 mmol, 1 eq.) in THF (15 mL) was added in a drop-wise fashion. The reaction was heated to reflux for 1 h, then cooled to room temperature and stirred for 16 h. The reaction was quenched by careful addition of H₂O (0.5 mL, 28 mmol), NaOH (15% aqueous solution, 1.08 mL, 46 mmol) and H₂O (1.62 mL, 100 mmol). The resulting slurry was stirred for a further 1 h and then filtered through a pad of celite545®. The filtered salts were washed with EtOAc (4×20 mL) and the combined organic filtrate was concentrated by rotary evaporation to afford the title compound [4-(4-iodo-phenyl)-1-methyl-piperidin-4-yl]-methylamine (1.05 g, 3.18 mmol, 70%) as a waxy yellow solid. This crude product is a 3:1 mixture of the desired product and a by-product corresponding to a loss of the 4-iodo substituent. ¹H NMR (300 MHz, CDCl₃): δ 7.79 (dd, 2H), 7.77 (dd, 2H), 3.76 (t, 2H), 2.85 (s, 2H), 2.70 (br. m, 2H), 2.3, (s+m, 9H), 1.8 (m, 8H).

EXAMPLE 3

C-[4-(4-Iodo-phenyl)-1-(3,3,3-trifluoro-propyl)-piperidin-4-yl]-methylamine

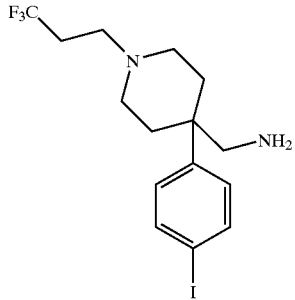

To a solution of the crude 4-(4-iodo-phenyl)-piperidine-4-carbonitrile (0.60 g, ~1.9 mmol) in CH₃CN (6 mL) was added (3,3,3-trifluoro)-propyl bromide (1.02 mL, 9.6 mmol, 5 eq.) and K₂CO₃ (1.33 g, 9.6 mmol, 5 eq.) and the resulting mixture was stirred and heated to 60° C. for 16 h. The reaction was cooled to room temperature, diluted with EtOAc (20 mL) and washed with H₂O (25 mL) and saturated brine (2×25 mL). The organic phase was dried over anhydrous Na₂SO₄, filtered and concentrated by rotary evaporation to give the crude 4-(4-iodo-phenyl)-1-(3,3,3-trifluoro-propyl)-piperidine-4-carbonitrile as a red solid (0.761 g, 1.86 mmol, 98%). ¹H NMR (300 MHz, CDCl₃): δ 7.83 (dd, 2H), 7.33 (dd, 2H), 3.09 (d, 2H), 2.82 (dd, 2H), 2.66 (td, 2H), 2.45 (m, 2H), 2.18 (m, 4H); MS (ESI): 409.1/410.2 (M+1).

To a solution of LiAlH₄ (1 M in THF, 6.5 mL, 6.5 mmol, 3.5 eq.) at 0° C. was added H₂SO₄ (0.31 mL, 5.58 mmol, 3 eq.) in a drop-wise fashion. The resulting white precipitate was stirred at 25° C. for 1 h. A solution of 4-(4-iodo-phenyl)-1-(3,3,3-trifluoro-propyl)-piperidine-4-carbonitrile (0.761 g, 1.86 mmol, 1 eq.) in THF (6 mL) was added and the mixture was heated at 40° C. for 3 h. The reaction was cooled to 0° C., quenched by addition of H₂O (0.25 mL), 1 N NaOH (0.5 mL) and H₂O (0.75 mL). The resulting slurry was filtered through a pad of celite, washed with EtOAc and then concentrated by rotary evaporation to give a yellow oil which was purified by flash column chromatography by eluting with 1.5% MeOH/1% Et₃N/CH₂Cl₂ to give the title compound C-[4-(4-Iodo-phenyl)-1-(3,3,3-trifluoro-propyl)-piperidin-4-yl]-methylamine as a pale foam (0.139 g, 0.337 mmol, 18%). ¹H NMR (300 MHz, CDCl₃): δ 7.80 (d, 2H), 7.18 (d, 2H), 3.78 (t, 1H), 2.86 (s, 2H), 2.74 (m, 2H), 2.62 (m, 2H), 2.30 (m, 4H+NH₂), 1.94 (ddd, 2H), 1.78 (m, 1H); MS(ESI): 413.0 (M+1).

EXAMPLE 4

C-[4-(4-Iodo-phenyl)-1-propyl-piperidin-4-yl]-methylamine

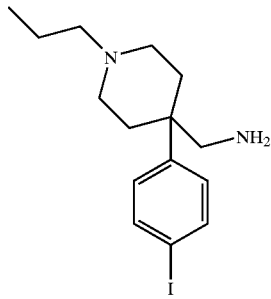

The title compound was prepared following a similar procedure as in Example 3.

¹HNMR (300 MHz, CDCl₃): δ 7.78 (d, 2H), 7.10 (d, 2H), 2.80 (s, 1H), 2.72 (br.m, 2H), 2.25 (m, 5H), 1.91 (m, 2H), 1.68 (m, 2H), 1.55 (m, 2H), 0.92 (t, 3H); MS (ESI): 359.1/360.2 (M+1).

EXAMPLE 5

C-[1-Cyclopropylmethyl-4-(4-iodo-phenyl)-piperidin-4-yl]-methylamine

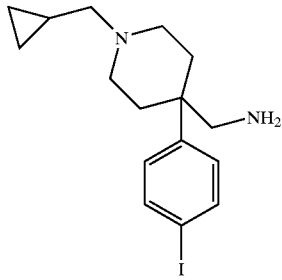

The title compound was prepared following a similar procedure as in Example 3. $^1$HNMR (300 MHz, CDCl$_3$): δ 7.76 (d, 2H), 7.12 (d, 2H), 2.80 (br. s., 3H), 2.24 (d, 5H), 1.90 (m, 2H), 1.48 (m, 2H), 0.88 (t, 1H), 0.54 (d, 2H), 0.10 (d, 2H); MS (ESI): 371.1/372.2 (M+1).

EXAMPLE 6

4-(4-Iodo-phenyl)-1-methyl-piperidine-4-carboxylic acid

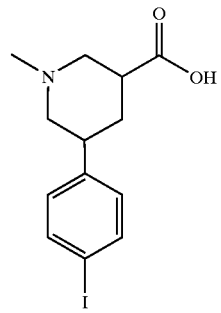

To a solution of 4-iodophenylacetonitrile (10 g, 41.1 mmol) in anhydrous DMSO (20 mL) was added NaNH$_2$ (4.8 g, 123.3 mmol, 3 eq.) in one portion. The temperature of the reaction was maintained at 20° C. using a water bath. The mixture was stirred at 20° C. for 20 min to give a deep red solution then a solution of bis-(2-chloro-ethyl)-methyl-amine.HCl salt (7.92 g, 41.1 mmol, 1 eq.) in anhydrous DMSO (20 mL) was added in a drop-wise fashion. The resulting mixture was stirred at room temperature for 16 h then partitioned between EtOAc (250 mL) and H$_2$O (250 mL). The organic layer was separated and washed with H$_2$O (3×100 mL) and saturated brine (100 mL) then dried over Na$_2$SO$_4$, filtered and concentrated by rotary evaporation. The crude product was purified by flash column chromatography by eluting with 10% MeOH/EtOAc to yield 4-(4-iodo-phenyl)-1-methyl-piperidine-4-carbonitrile as a brownish solid (7.6 g, 23.43 mmol, 57%). $^1$H NMR (300 MHz, CD$_3$OD): δ 7.89 (d, 2H), 7.43 (d, 2H), 3.13 (d, 2H), 2.58 (td, 2H), 2.50 (s, 3H), 2.24 (m, 4H).

A suspension of 4-(4-iodo-phenyl)-1-methyl-piperidine-4-carbonitrile (1.0 g, 3.07 mmol) in concentrated HCl (20 mL) was heated at 100° C. for 16 h. The resulting mixture was concentrated by rotary evaporation to give a white solid. The solid was suspended in H$_2$O (80 mL), Amberlite IR-120 (15 g) was added and the cloudy suspension was heated at reflux for 16 h. The resulting clear solution was filtered and the resin was washed with H$_2$O (2×30 mL). The resin was then shaken and washed with 5% pyridine/H$_2$O (4×50 mL). The filtrate from the pyridine wash was collected and concentrated by rotary evaporation to give 4-(4-iodo-phenyl)-1-methyl-piperidine-4-carboxylic acid pyridine salt as a white solid (0.96 g, 90%). $^1$H NMR (300 MHz, CD$_3$OD): δ 9.02 (d, 2H), 8.82 (t, 1H), 8.29 (t, 2H), 7.85 (d, 2H), 7.35 (d, 2H), 3.75 (d, 2H), 3.26 (t, 2H), 3.02 (s, 3H), 2.93 (d, 2H), 2.23 (t, 2H).

EXAMPLE 7

1-[4-(3'-Cyano-biphenyl-4-yl)-1-isobutyl-piperidin-4-ylmethyl]-3-(3,5-dichloro-phenyl)-urea

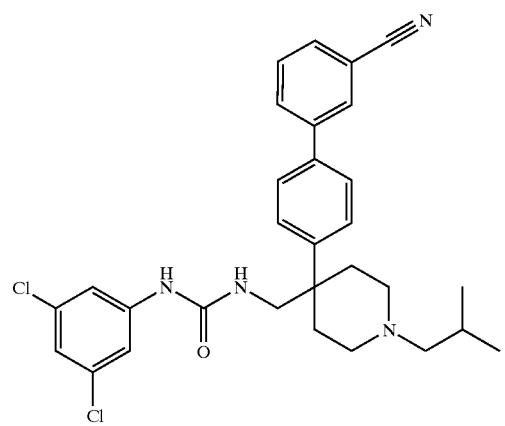

To a suspension of polystyrene-NH$_2$ resin (from Polymer Laboratories, Amherst, Mass.; 10 g, 1.83 mmol/g, 18.3 mmol) in DMF (20 mL) and CH$_2$Cl$_2$ (150 mL) was added HOBt (7.4 g, 55 mmol, 3 eq.), 4-(formyl-3-methoxy-phenoxy)-butyric acid (13.1 g, 55 mmol, 3 eq.) and DIC (17.2 mL, 110 mL, 6 eq.). The mixture was shaken gently for 16 h then filtered and washed with CH$_2$Cl$_2$ (3×), DMF (3×), DMF/MeOH (3×), MeOH/CH$_2$Cl$_2$ (3×) and CH$_2$Cl$_2$ (3×).

To a portion of the resin (1.7 g, 1.83 mmol/g, 3.11 mmol) was added a solution of 4-aminomethyl-4-(4-iodophenyl)-1-piperidine-1-carboxylic acid tert-butyl ester (3.18 g, 7.65 mmol, 2.5 eq.) in ClCH$_2$CH$_2$Cl (20 mL). The mixture was shaken gently for 1 h then Na(OAc)$_3$BH (3.32 g, 15.3 mmol, 5 eq.) was added and the reaction was shaken for 16 h. The resin was filtered and washed with MeOH (1×), DMF (3×), MeOH (3×) and CH$_2$Cl$_2$ (3×). An aliquot of the resin tested positive with chloranil and negative with 2,4-dinitrophenylhydrazine, indicating complete conversion from aldehyde to secondary amine.

The resin (1.7 g, 1.83 mmol/g, 3.11 mmol) was suspended in CH$_2$Cl$_2$ (20 mL) and DIEA (5.6 mL, 31.1 mmol, 10 eq.) was added, followed by 3,5-dichlorophenyl isocyanate (2.83 g, 15.3 mmol, 5 eq.). The mixture was shaken at room temperature for 16 h, the solution filtered and the resin washed with CH$_2$Cl$_2$ (3×), DMF (3×), MeOH (2×) and CH$_2$Cl$_2$ (3×).

To the CH$_2$Cl$_2$ soaked resin (1.7 g, 1.83 mmol/g, 3.11 mmol) was added TMSOTf (25 mL of a 1 M solution in CH$_2$Cl$_2$, 25 mmol) and 2,6-lutidine (25 mL of a 1.5M solution in CH$_2$Cl$_2$, 37.5 mmol). The resin was shaken gently for 30 min. The resin was filtered and a second cycle of the Boc-deprotection sequence was carried out. The resin was washed with CH$_2$Cl$_2$ (4×), MeOH (3×), DMF (3×), MeOH (3×) and CH$_2$Cl$_2$ (4×).

To a portion of the resin (0.5 g, 1.83 mmol/g, 0.9 mmol) was added a solution of isobutyraldehyde (0.38 g, 5.4 mmol, 6 eq.) in DMF (10 mL). The mixture was shaken gently for 2 h then Na(OAc)$_3$BH (1.8 g, 9 mmol, 10 eq.) was added and the reaction mixture was shaken for 16 h. The resin was filtered and washed with MeOH (1×), DMF (3×), MeOH (3×) and CH$_2$Cl$_2$ (3×).

A portion of the resin (0.125 g, 1.83 mmol/g, 0.22 mmol) was mixed with 3-cyanophenylboronic acid (0.165 g, 1.14 mmol, 5 eq), K$_2$CO$_3$ (0.186 g, 1.35 mmol, 6 eq) and Pd(PPh$_3$)$_4$ (0.026 g). DMF (3 mL, degassed with Ar) was added and the mixture was heated to 70° C. for 16 h. The solution was filtered and the resin was washed with DMF (4×), H₂O/DMF (4×), DMF/MeOH (3×), MeOH/CH₂Cl₂ (3×) and CH₂Cl₂ (4×).

The resin was treated with a solution of TFA (3 mL of a 25% v/v solution in CH₂Cl₂) and shaken for 2 h at room temperature. The resin was then filtered off and the filtrate was purified by Gilson 215 HPLC (10–90% acetonitrile/water) to yield the pure title compound 1-[4-(3'-cyano-biphenyl-4-yl)-1-isobutyl-piperidin-4-ylmethyl]-3-(3,5-dichloro-phenyl)-urea (0.0005 g, 0.4%). MS (ESI): 534.2/535.2 (M+1).

EXAMPLE 8

1-[4-(3'-Cyano-biphenyl-4-yl)-1-cyclopropylmethyl-piperidin-4-ylmethyl]-3-(3.5-dichloro-phenyl)-urea

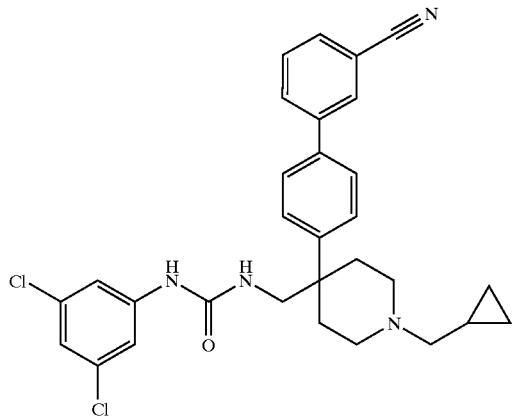

To a mixture of polystyrene-NH₂ resin (from Polymer Laboratories; 10 g, 1.83 mmol/g, 18.3 mmol) in DMF (20 mL) and CH₂Cl₂ 150 mL) was added HOBt (7.4 g, 55 mmol, 3 eq.), ⁴-(formyl-3-methoxy-phenoxy)-butyric acid (13.1 g, 55 mmol, 3 eq.) and DIC (17.2 mL, 110 mL, 6 eq.). The mixture was shaken gently for 16 h then filtered and washed with CH₂Cl₂ (3×), DMF (3×), DMF/MeOH (2×), MeOH/CH₂Cl₂ (2×) and CH₂Cl₂ (3×).

To a portion of the resin (1.2 g, 1.83 mmol/g, 2.2 mmol) was added a solution of C-[4-(4-iodo-phenyl)-1-cyclopropylmethyl-piperidin-4-yl]-methylamine (2.02 g, 5.45 mmol, 2.5 eq.) in ClCH₂CH₂Cl (20 mL). The mixture was shaken gently for 1 h then Na(OAc)₃BH (1.15 g, 5.45 mmol, 2.5 eq.) was added and the reaction mixture was shaken for 16 h. The resin was filtered and washed with MeOH (1×), DMF (3×), MeOH (3×) and CH₂Cl₂ (3×). An aliquot of the resin tested positive with chloranil and negative with 2,4-dinitrophenylhydrazine, indicating complete conversion from aldehyde to secondary amine.

A portion of the resin (~0.12 g, 0.22 mmol) was suspended in CH₂Cl₂ (3.0 mL) and DIEA (0.38 mL, 2.2 mmol, 10 eq.) was added, followed by 3,5-dichlorophenyl isocyanate (0.283 g, 1.5 mmol, to give a 0.5M solution). The mixture was shaken at room temperature for 16 h, the solution filtered and the resin washed with CH₂Cl₂ (3×), DMF (3×), MeOH (2×) and CH₂Cl₂ (3×).

The resin (0.12 g, 0.22 mmol) was mixed with 3-cyanophenylboronic acid (0.135 g, 0.9 mmol, 4 eq.), K₂CO₃ (0.150 g, 1.1 mmol, 5 eq.) and Pd(PPh₃)₄ (0.05 g, 0.044 mmol, 0.2 eq.). DMF (3 mL, degassed with Ar) was added and the mixture was heated to 70° C. for 16 h. The solution was filtered and the resin was washed with DMF (4×), H₂O/DMF (4×), DMF/MeOH (3×), MeOH/CH₂Cl₂ (3×) and CH₂Cl₂ (4×).

The resin was treated with a solution of TFA (3 mL of a 25% v/v solution in CH₂Cl₂) and shaken for 2 h at room temperature. The resin was filtered off and the filtrate was purified by Gilson 215 HPLC (10–90% acetonitrile/water) to yield 1-[4-(3'-cyano-biphenyl-4-yl)-1-cyclopropylmethyl-piperidin-4-ylmethyl]-3-(3,5-dichloro-phenyl)-urea (0.0145 g, 12.5%). ¹H NMR (300 MHz, CDCl₃): δ 8.60 (1H, br.s), 7.92 (2, m), 7.73 (4H, m), 7.54 (2H, m), 7.47 (1H, s), 7.03 (1H, s), 6.65 (1H, br.s), 3.71 (2H, d), 3.46 (2H, br.s), 3.16 (2H, br.s), 2.78 (4H, m), 2.60 (2H, d), 1.15 (1H, m), 0.87 (2H, d), 0.48 (2H, d). MS (ESI): 533.2/535.2 (M+1).

EXAMPLE 9

1-[4-(3'-Cyano-biphenyl-4-yl)-1-methyl-piperidin-4-ylmethyl]-3-(2,4-difluoro-phenyl)-urea

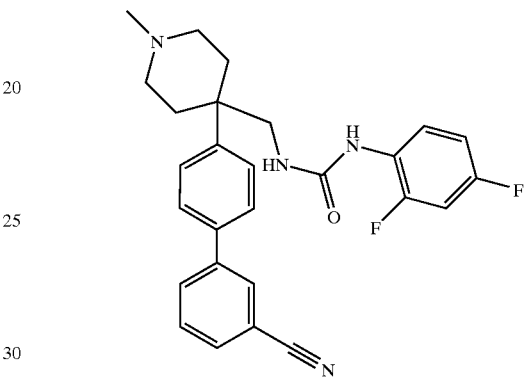

To a solution of [4-(4-iodo-phenyl)-1-methyl-piperidin-4-yl]-methylamine (0.20 g, 0.606 mmol) in CH₂Cl₂ (2 mL) under Ar was added 2,4-difluorophenylisocyanate (0.08 mL, 0.667 mmol, 1.1 eq.) and DIEA (0.106 mL, 0.606 mmol, 1 eq.). The mixture was stirred at room temperature for 16 h then diluted with EtOAc (25 mL) and washed with H₂O (20 mL) and saturated brine (20 mL). The organic layer was dried over anhydrous Na₂SO₄, filtered and concentrated to give a yellow oil which was purified by flash column chromatography by eluting with 3% MeOH/CH₂Cl₂ (1% TEA) to furnish 1-(2,4-difluoro-phenyl)-3-[4-(4-iodo-phenyl)-1-methyl-piperidin-4-yl-methyl]-urea as a white solid (0.211 g, 0.435 mmol, 72%). ¹H NMR (300 MHz, CDCl₃): δ 7.84 (br.d, NH), 7.68 (d, 2H), 7.36 (s, 1H), 7.11 (d, 2H), 6.87 (d, 2H), 5.32 (br.s., NH), 3.40 (s, 2H), 2.66 (m, 4H), 2.28 (s, 3H), 2.10 (m, 2H), 1.96 (m, 2H), 1.14 (t, 3H). MS (ESI): 486.1,487.0 (M+1).

To a flask containing 1-(2,4-difluoro-phenyl)-3-[4-(4-iodo-phenyl)-1-methyl-piperidin-4-ylmethyl]-urea (0.211 g, 0.435 mmol) was added Pd(PPh₃)₄ (0.05 g, 0.0435 mmol, 10 mol %), 3-cyanophenylboronic acid (0.096 g, 0.653 mmol, 1.5 eq.) and Na₂CO₃ (0.424 g, 4 mmol). The mixture was suspended in toluene (6 mL), EtOH (3 mL) and H₂O (2 mL) and heated to 80° C. for 8 h. The reaction mixture was cooled to room temperature and partitioned between EtOAc and saturated Na₂CO₃. The organic layer was washed with saturated Na₂CO₃ (3×10 mL), saturated brine (3×10 mL) then dried over anhydrous sodium sulfate, filtered and concentrated by rotary evaporation to give a brown solid which was purified by flash column chromatography by eluting with 2% MeOH/1% TEA/EtOAc to give the product (0.159 g) which was further purified by HPLC to give the title compound 1-[4-(3'-cyano-biphenyl-4-yl)-1-methyl-piperidin-4-ylmethyl]-3-(2,4-difluoro-phenyl)-urea as a pale solid (0.0306 g, 0.066 mmol, 15%). ¹H NMR (300 MHz, CDCl$_3$): δ 7.88 (m, 3H), 7.66 (m, 4H), 7.50 (d, 2H), 6.82 (d, 2H), 3.42 (m, 5H), 2.78 (m, 4H), 2.40 (m, 4H). MS (ESI): 461.2/462.2 (M+1).

EXAMPLE 10

N-[4-(3'-Cyano-biphenyl-4-yl)-1-cyclopropylmethyl-piperidin-4-ylmethyl]-2-(3,5-difluoro-phenyl)-acetamide

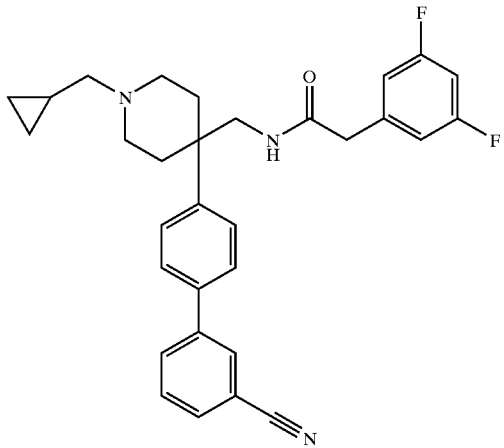

To a stirred solution of 3,5-difluorophenyl acetic acid (0,172 g, 1 mmol) in CH$_2$Cl$_2$ (1 mL) at room temperature under Ar was added (COCl)$_2$ (0.175 mL, 2 mmol, 2 eq.) followed by DMF (0.01 mL, catalyst). The resulting mixture was stirred at room temperature for 16 h. The mixture was concentrated by rotary evaporation and the resulting oil was evaporated from CH$_2$Cl$_2$ (2×5 mL) and toluene (1×5 mL) and dried under high vacuum for 1 h to give (3,5-difluoro-phenyl)-acetyl chloride as a pale yellow oil.

To a stirred solution of 4-aminomethyl-4-(4-iodo-phenyl)-piperidine-1-carboxylic acid tert-butyl ester (0.10 g, 0.24 mmol) in CH$_2$Cl$_2$ (0.5 mL) at room temperature under Ar was added a solution of 3,5-difluorophenylacetyl chloride (0.28 mL of a 1 M solution in CH$_2$Cl$_2$, 0.28 mmol) followed by pyridine (0.25 mL). The mixture was stirred at room temperature for 16 h then diluted with EtOAc (5 mL) and washed with saturated aqueous NaHCO$_3$ (5 mL) and saturated brine (5 mL) and dried over Na$_2$SO$_4$. Filtration and rotary evaporation gave the crude 4-{[2-(3,5-difluoro-phenyl)-acetylamino]-methyl}-4-(4-iodo-phenyl)-piperidine-1-carboxylic acid tert-butyl ester (0.09 g, ~65%).

To a stirred solution of 4-{[2-(3,5-difluoro-phenyl)-acetylamino]-methyl}-4-(4-iodo-phenyl)-piperidine-1-carboxylic acid tert-butyl ester (0.09 g, 0.16 mmol) in CH$_2$Cl$_2$ (1.5 mL) at 0° C. was added TFA (0.5 mL, to give a 25% v/v solution). The mixture was stirred at room temperature for 3 h at which time TLC (4:1 hexanes/EtOAc) showed no starting material left. The solvent was removed by rotary evaporation and the resulting liquid was evaporated from toluene (2×10 mL) then diluted with EtOAc (100 mL) and washed with 10% aqueous NaHCO$_3$ solution (2×50 mL) and saturated brine (50 mL). The organic layer was dried over anhydrous Na$_2$SO$_4$, filtered, concentrated by rotary evaporation, and dried under high vacuum for 1 h to yield 4-{[2-(3,5-difluoro-phenyl)-acetylamino]-methyl}-4-(4-iodo-phenyl)-piperidine as a reddish solid (0.038 g, ~0.08 mmol). MS (ESI): 471.1 (M+1).

To a stirred solution of 4-{[2-(3,5-difluoro-phenyl)-acetylamino]-methyl}-4-(4-iodo-phenyl)-piperidine (0.038 g, ~0.08 mmol) in ClCH$_2$CH$_2$Cl (0.5 mL) at room temperature under Ar was added cyclopropanecarboxaldehyde (0.008 mL, 0.096 mmol, 1.2 eq.) and HOAc (0.05 mL, 1% v/v). The mixture was stirred for 0.5 h then Na(OAc)$_3$BH (0.026 g, 0.12 mmol, 1.5 eq.) was added and the mixture stirred for 16 h then diluted with EtOAc (5 mL) and washed with saturated aqueous NaHCO$_3$ solution (5 mL) and saturated brine (5 mL). The organic layer was dried over anhydrous Na$_2$SO$_4$, filtered, concentrated by rotary evaporation, and dried under high vacuum to give N-[1-cyclopropylmethyl-4-(4-iodo-phenyl)-piperidin-4-ylmethyl]-2-(3,5-difluoro-phenyl)-acetamide (0.040 g, 0.76 mmol, 95%). MS (ESI): 525.2/526.2 (M+1).

To a flask containing 1 N-[1-cyclopropylmethyl-4-(4-iodo-phenyl)-piperidin-4-ylmethyl]-2-(3,5-difluoro-phenyl)-acetamide (0.040 g, 0.76 mmol) was added Pd(PPh$_3$)$_4$ (0.01 g, 0.008 mmol, 10 mol %), 3-cyanophenylboronic acid (0.020 g, 0.12 mmol, 1.5 eq.) and Na$_2$CO$_3$ (0.106 g, 1 mmol). The mixture was suspended in toluene (1.5 mL), EtOH (0.75 mL) and H$_2$O (0.5 mL) and heated to 80° C. for 18 h. The reaction mixture was cooled to room temperature and partitioned between EtOAc (5 mL) and saturated Na$_2$CO$_3$ (5 mL). The organic layer was washed with saturated Na$_2$CO$_3$ (3×5 mL), saturated brine (2×5 mL), dried over anhydrous sodium sulfate, filtered and concentrated to give a brown solid which was purified by HPLC to give the title compound N-[4-(3'-cyano-biphenyl-4-yl)-1-cyclopropylmethyl-piperidin-4-ylmethyl]-2-(3,5-difluoro-phenyl)-acetamide (0.036 g, 0.072 mmol, 10%). MS(ESI): 500.3/501.3 (M+1).

EXAMPLE 11

3-Chloro-N-[4-(3'-cyano-biphenyl-4-yl)-1-cyclopropylmethyl-piperidin-4-ylmethyl]-4-fluoro-benzenesulfonamide

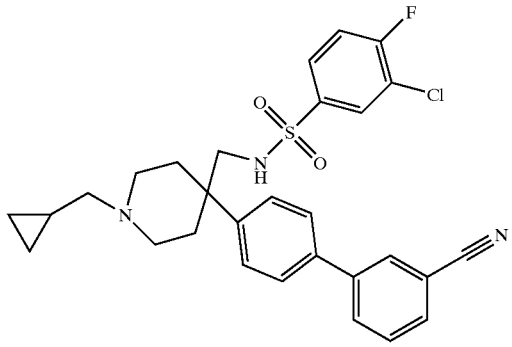

To a stirred solution of 4-aminomethyl-4-(4-iodo-phenyl)-piperidine-1-carboxylic acid tert-butyl ester (0.10 g, 0.24 mmol) in CH$_2$Cl$_2$ (1.0 mL) at room temperature under Ar was added a solution of 3-chloro-4-fluorophenylsulfonyl chloride (0.06 g, 0.26 mmol, 1.1 eq.) followed by pyridine (0.25 mL). The mixture was stirred at room temperature for 16 h, diluted with EtOAc (5 mL), washed with saturated aqueous NaHCO$_3$ (5 mL) and saturated brine (5 mL) and dried over Na$_2$SO$_4$. Filtration and rotary evaporation yielded the crude 4-[(3-chloro-4-fluoro-benzenesulfonylamino)-methyl]-4-(4-iodo-phenyl)-piperidine-1-carboxylic acid tert-butyl ester as a yellow oil (0.09 g, 0.14 mmol, ~62%). $^1$HNMR (300 MHz, CDCl$_3$): δ 8.66 (d, 1H), 7.81–7.73 (m, 3H), 7.34 (m, 1H), 7.15 (d, 1H), 7.08 (d, 1H), 3.79 (m, 2H), 3.13 (m, 3H), 2.19 (m, 3H), 1.77 (m, 2H), 1.56 (s, 9H). MS(ESI): 509 (M−Boc).

To a stirred solution of 4-[(3-chloro-4-fluoro-benzenesulfonylamino)-methyl]-4-(4-iodo-phenyl)-piperidine-1 carboxylic acid tert-butyl ester (0.09 g, 0.16 mmol) in CH$_2$Cl$_2$ (1.5 mL) at 0° C. was added TFA (0.5 mL, to give a 25% v/v solution). The mixture was stirred at room temperature for 3 h. TLC (4:1 hexanes/EtOAc) showed no starting material left. The solvent was removed by rotary evaporation and the resulting liquid was evaporated from toluene (2×10 mL), diluted with EtOAc (100 mL) and washed with 10% aqueous NaHCO$_3$ solution (2×50 mL) and saturated brine (50 mL). The organic layer was dried over anhydrous Na$_2$SO$_4$, filtered, concentrated by rotary evaporation, and dried under high vacuum for 1 h to give 3-chloro-4-fluoro-N-[4-(4-iodo-phenyl)-piperidin-4-ylmethyl]-benzenesulfonamide as a reddish solid (0.021 g, ~0.04 mmol). MS: 509/511 (M+1).

To a stirred solution of 3-chloro-4-fluoro-N-[4-(4-iodo-phenyl)-piperidin-4-ylmethyl]-benzenesulfonamide (0.0321 g, 0.04 mmol) in ClCH$_2$CH$_2$Cl (0.5 mL) at room temperature under Ar was added cyclopropanecarboxaldehyde (0.005 mL, 0.048 mmol, 1.2 eq) and HOAc (0.05 mL, 1%v/v). The mixture was stirred for 0.5 h. Na(OAc)$_3$BH (0.015 g, 0.06 mmol, 1.5 eq) was added and the mixture stirred for 16 h, diluted with EtOAc (20 mL) and washed with saturated aqueous NaHCO$_3$ solution (10 mL) and saturated brine (10 mL). The organic layer was dried over anhydrous Na$_2$SO$_4$, filtered, concentrated by rotary evaporation, then dried under high vacuum to give 3-chloro-N-[1-cyclopropylmethyl-4-(4-iodo-phenyl)-piperidin-4-ylmethyl]-4-fluorobenzenesulfonamide (0.047 g, 0.04 mmol, 95%). MS (ESI): 563.1/565.1 (M+1).

To a flask containing 3-chloro-N-[1-cyclopropylmethyl-4-(4-iodo-phenyl)-piperidin-4-ylmethyl]-4-fluorobenzenesulfonamide (0.047 g, 0.04 mmol) was added Pd(PPh$_3$)$_4$ (0.005 g, 0.004 mmol, 10 mol %), 3-cyanophenylboronic acid (0.01 g, 0.06 mmol, 1.5 eq.) and Na$_2$CO$_3$ (0.106 g, 1 mmol). The mixture was suspended in toluene (1.5 mL), EtOH (0.75 mL) and H$_2$O (0.5 mL) and heated to 80° C. for 18 h. The reaction mixture was cooled to room temperature and partitioned between ethyl acetate (5 mL) and saturated Na$_2$CO$_3$ (5 mL). The organic layer was washed with saturated Na$_2$CO$_3$ (3×5 mL), saturated brine (2×5 mL), dried over anhydrous sodium sulfate, filtered and concentrated to give a brown solid which was purified by HPLC to give 3-chloro-N-[4-(3'-cyano-biphenyl-4-yl)-1-cyclopropylmethyl-piperidin-4-ylmethyl]-4-fluoro-benzenesulfonamide (0.097 g, 45%). MS (ESI): 538.2/540.2.

EXAMPLE 12

[4-(3'-Cyano-biphenyl-4-yl)-1-cyclopropylmethyl-piperidin-4-ylmethyl]-carbamic acid isobutyl ester

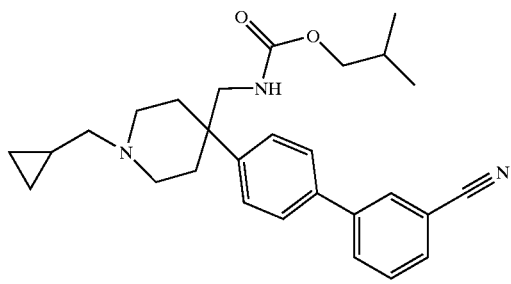

To a stirred solution of 4-aminomethyl-4-(4-iodo-phenyl)-piperidine-1-carboxylic acid tert-butyl ester (0.10 g, 0.24 mmol) in CH$_2$Cl$_2$ (1.0 mL) at room temperature under Ar was added isobutyl chloroformate (0.033 mL, 0.26 mmol, 1.1 eq.) followed by pyridine (0.25 mL). The mixture was stirred at room temperature for 16 h, diluted with EtOAc (5 mL), washed with saturated aqueous NaHCO$_3$ (5 mL) and saturated brine (5 mL) and dried over Na$_2$SO$_4$. Filtration and rotary evaporation gave the crude 4-(4-iodo-phenyl)-4-(isobutoxycarbonylamino-methyl)-piperidine-1-carboxylic acid tert-butyl ester as a yellow oil (0.075 g, 0.15 mmol, ~62%). $^1$H NMR (300 MHz, CDCl$_3$): δ 7.81 (d, 2H), 7.15 (d, 2H), 4.42 (br.t, 1H), 3.88 (d, 2H), 3.79 (m, 2H), 3.42 (br.m, 2H), 3.25 (br.t, 2H), 2.13 (br.m, 3H), 1.88 (m, 3H), 1.54 (s, 9H), 0.99 (d, 6H). MS: 417 (M−Boc).

To a stirred solution of 4-(4-iodo-phenyl)-4-(isobutoxycarbonylamino-methyl)-piperidine-1-carboxylic acid tert-butyl ester (0.075 g, 0.15 mmol) in CH$_2$Cl$_2$ (1.5 mL) at 0° C. was added TFA (0.5 mL). The mixture was stirred at room temperature for 3 h. TLC (4:1 hexanes/EtOAc) showed no starting material left. The solvent was removed by rotary evaporation and the resulting liquid was evaporated from toluene (2×10 mL), diluted with EtOAc (100 mL) and washed with 10% aqueous NaHCO$_3$ solution (2×50 mL) and saturated brine (50 mL). The organic layer was dried over anhydrous Na$_2$SO$_4$, filtered, concentrated by rotary evaporation and dried under high vacuum for 1 h to give [4-(4-iodo-phenyl)-piperidin-4-ylmethyl]-carbamic acid isobutyl ester as a reddish solid (0.058 g, ~0.14 mmol). MS (ESI): 417.1/418.1(M+1).

To a stirred solution of [4-(4-iodo-phenyl)-piperidin-4-ylmethyl]-carbamic acid isobutyl ester (0.058 g, 0.14 mmol) in ClCH$_2$CH$_2$Cl (0.75 mL) at room temperature under Ar was added cyclopropanecarboxaldehyde (0.012 mL, 0.156 mmol, 1.2 eq.) and HOAc (0.075 mL, 1% v/v). The mixture was stirred for 0.5 h then Na(OAc)$_3$BH (0.041 g, 0.2 mmol, 1.5 eq.) was added. The mixture was stirred for 16 h, diluted with EtOAc (10 mL) and washed with saturated aqueous NaHCO$_3$ solution (10 mL) and saturated brine (10 mL). The combined organic layers were dried over Na$_2$SO$_4$, filtered and concentrated by rotary evaporation to give [1-cyclopropylmethyl-4-(4-iodo-phenyl)-piperidin-4-ylmethyl]-carbamic acid isobutyl ester (0.061 g, 95%). MS (ESI): 471.2/472.2 (M+1).

To a flask containing [1-cyclopropylmethyl-4-(4-iodo-phenyl)-piperidin-4-ylmethyl]-carbamic acid isobutyl ester (0.061 g, 0.13 mmol) was added Pd(PPh$_3$)$_4$ (0.015 g, 0.013 mmol, 10 mol %), 3-cyanophenylboronic acid (0.03 g, 0.2 mmol, 1.5 eq.) and Na$_2$CO$_3$ (0.212 g, 2 mmol). The mixture was suspended in toluene (3 mL), EtOH (1.5 mL) and H$_2$O (1.0 mL) and heated to 80° C. for 18 h. The reaction mixture was cooled to room temperature and partitioned between EtOAc (10 mL) and saturated Na$_2$CO$_3$ (10 mL). The organic layer was washed with saturated Na$_2$CO$_3$ (3×10 mL) and saturated brine (2×10 mL), dried over anhydrous sodium sulfate, filtered and concentrated to give the crude product. This was purified by HPLC to give the title compound [4-(3'-cyano-biphenyl-4-yl)-1-cyclopropylmethyl-piperidin-4-ylmethyl]-carbamic acid isobutyl ester as a brown solid (0.014 g, 24%). MS (ESI): 446.3/447.3 (M+1).

EXAMPLE 13

4'-{1-[3-(3,4-Difluoro-phenyl)-2-oxo-imidazolidin-1-ylmethyl]4-methyl-cyclohexyl}-biphenyl-3-carbonitrile

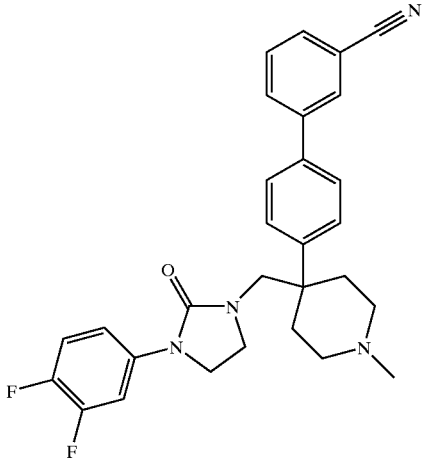

A solution of 3,4-difluorophenyl isocyanate (2 g, 10.55 mmol) in t-BuOH (50 mL) was heated at 80° C. for 16 h. The mixture was concentrated by rotary evaporation to give a white solid which was triturated with toluene and evaporated to dryness. Addition of toluene (20 mL) and concentration under vacuum gave (3,4-difluorophenyl)-carbamic acid-tert-butyl ester as a white solid (2.43 g, 100%).

$^1$H NMR (300 MHz, CDCl$_3$): δ7.20 (m, 3H), 1.52 (s, 9H).

To a solution of (3,4-difluorophenyl)-carbamic acid-tert-butyl ester (2.42 g, 10.55 mmol) in DMF (80 mL) at 0° C. under Ar was added NaH (60% dispersion in mineral oil, 0.805 g, 21 mmol, 2 eq.). The mixture was stirred at 0° C. for 30 min and then allyl iodide (6.42 mL, 53 mmol, 5 eq.) was added over 5 min. The mixture was warmed to room temperature and stirred for 2 h. The mixture was then diluted with EtOAc (100 mL) and washed with saturated aqueous NaHCO$_3$ (100 mL). The aqueous phase was washed with EtOAc (3×60 mL) and the combined organic extracts were washed with saturated aqueous NaCl (100 mL), dried over Na$_2$SO$_4$, filtered and concentrated to give a brown oil which was purified by flash column chromatography by eluting with 10% EtOAc/hexanes to give allyl-(3,4-difluorophenyl)-carbamic acid-tert-butyl ester as a clear oil (2.238 g, 75%).). $^1$H NMR (300 MHz, CDCl$_3$): δ 7.18 (m, 3H), 6.00 (m, 1H), 5.30 (m, 2H), 4.30 (m, 2H), 1.59 (s, 9H).

A stirred solution of allyl-(3,4-difluorophenyl)-carbamic acid-tert-butyl ester (2.23 g, 7.9 mmol) in CH$_2$Cl$_2$ (75 mL) was cooled to −78° C. O$_3$ was bubbled through for ~5 min (reaction monitored by TLC). O$_2$ was then bubbled through for 5 min. DMS (5 mL, 77 mmol, 10 eq.) was added and the mixture was warmed to room temperature and stirred for 6 h. Following a further addition of Me$_2$S (5 mL, 77 mmol, 10 eq.) the mixture was stirred at room temperature for 14 h. The mixture was concentrated by rotary evaporation and the resulting residue was purified by flash column chromatography by eluting with 20% EtOAc/hexanes to yield (3,4-difluorophenyl)-(2-oxo-ethyl)-carbamic acid-tert-butyl ester (1.23 g, 59%) as a pale oil. $^1$H NMR (300 MHz, CDCl$_3$): δ 9.78 (s, 1H), 7.18 (m, 3H), 4.40 (s, 2H), 1.56 (s, 9H).

To a stirred solution of (3,4-difluorophenyl)-(2-oxo-ethyl)-carbamic acid-tert-butyl ester (1.23 g, 4.3 mmol) in MeOH (35 mL) under Ar at room temperature was added a solution of C-[4-(4-iodo-phenyl)-1-methyl-piperidin-4-yl]-methylamine (1.49 g, 4.5 mmol, 1.05 eq.) in MeOH (10 mL). The mixture was stirred at room temperature for 5 h then NaBH$_4$ (0.255 g, 6.75 mmol, 1.5 eq) was added and the resulting mixture was stirred for a further 1 h and then was quenched by the addition of 1N aqueous NaOH (40 mL). The mixture was extracted twice with Et$_2$O (2×50 mL) and the combined organic extracts were washed with saturated brine (100 mL) and dried over Na$_2$SO$_4$. Filtration and concentration of the filtrate by rotary evaporation gave the crude product which was purified by flash column chromatography by eluting with 12% EtOAc/hexanes to give (3,4-difluoro-phenyl)-(2-{[4-(4-iodo-phenyl)-1-methyl-piperidin-4-ylmethyl]-amino}-ethyl)-carbamic acid tert-butyl ester (2.03 g, 76%) as a pale oil. MS (ESI): 585.9/587.0 (M+H).

To a stirred solution of (3,4-difluoro-phenyl)-(2-{[4-(4-iodo-phenyl)-1-methyl-piperidin-4-ylmethyl]-amino}-ethyl)-carbamic acid tert-butyl ester (2.03 g, 3.47 mmol) in CH$_2$Cl$_2$ (25 mL) at 0° C. was added TFA (6 mL, to give a 25% v/v solution). The mixture was stirred and warmed to room temperature for 4 h. The solvent was removed by rotary evaporation and the residue was dissolved in EtOAc (50 mL) and washed with 10% aqueous NaHCO$_3$ (2×50 mL). The organic extracts were dried over sodium sulfate, filtered and concentrated by rotary evaporation to give N-(3,4-difluoro-phenyl)—N'-[4-(4-iodo-phenyl)-1-methyl-piperidin-4-ylmethyl]-ethane-1,2-diamine (1.20 g, 96%) as a white solid.

To a stirred solution of N-(3,4-difluoro-phenyl)-N'-[4-(4-iodo-phenyl)-1-methyl-piperidin-4-ylmethyl]-ethane-1,2-diamine (0.36 g, 1.0 mmol) in THF (10 mL) at 0° C. was added TEA (0.91 mL, 6.5 mmol, 6.5 eq.) and triphosgene (0.195 g, 0.65 mmol, 0.65 eq.). The mixture was stirred at room temperature for 4 h, diluted with EtOAc (25 mL) and washed with saturated brine (2×25 mL). The organic extracts were dried over sodium sulfate, filtered and concentrated by rotary evaporation to give a yellow oil. The crude product was purified by flash column chromatography by eluting with 2% MeOH/CH$_2$Cl$_2$ to give 1-(3,4-difluoro-phenyl)-3-[4-(4-iodo-phenyl)-1-methyl-piperidin-4-ylmethyl]-imidazolidin-2-one (0.023 g, 0.045 mmol, 5%) as a pale foam. MS (ESI): 512.1/513.1 (M+H), impurity peak 690.9/692.0.

To a stirred solution of 1-(3,4-difluoro-phenyl)-3-[4-(4-iodo-phenyl)-1-methyl-piperidin-4-ylmethyl]-imidazolidin-2-one (0.023 g, ~0.045 mmol) in toluene (0.6 mL), EtOH (0.3 mL) and 2M aqueous Na$_2$CO$_3$ (0.2 mL) was added 3-cyanophenyl boronic acid (0.010 g, 0.0068 mmol, 1.5 eq.) and Pd(PPh$_3$)$_4$ (0.0052 g, 0.0045 mmol, 10 mol %). The mixture was stirred and heated to 80° C. for 16 h. The mixture was cooled to room temperature and diluted with EtOAc (10 mL) and washed with saturated aqueous Na$_2$CO$_3$ solution (3×10 mL). The aqueous layer was extracted with EtOAc (2×10 mL). The combined organic extracts were washed with saturated aqueous Na$_2$CO$_3$ solution (25 mL) and saturated brine (25 mL). The organic layer was separated, dried over sodium sulfate, filtered and concentrated to give a brown oil. Purification by HPLC gave 4'-{1-[3-(3,4-difluoro-phenyl)-2-oxo-imidazolidin-1-ylmethyl]-4-methyl-cyclohexyl}-biphenyl-3-carbonitrile. (0.007 g, 32%) as a white foam. MS (ESI): 487.2/488.3 (M+1).

EXAMPLE 14

1-[4-(3'-Cyano-biphenyl-4-yl)-1-cyclopropylmethyl-piperidin-4-ylmethyl]-3-(3,5-dichloro-phenyl)-1-methyl-urea

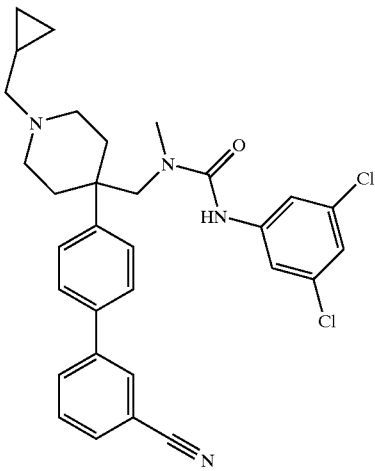

A solution of LiAH$_4$ (8.5 mL of a 1.0M solution in THF, 8.5 mmol, 3.5 eq.) was cooled to 0° C. and concentrated H$_2$SO$_4$ (0.43 mL, 7.6 mmol, 3.2 eq) was added in a drop-wise fashion. The resulting white slurry was stirred at room temperature for 0.5 h then heated to 30° C. for 0.5 h. The reaction was cooled to room temperature and a solution of 4-cyano-4-(4-iodo-phenyl)-piperidine-1-carboxylic acid tert-butyl ester (1 g, 2.43 mmol) in THF (3 mL) was added over 0.25 h. The mixture was heated to 55° C. and monitored by TLC. After 5 h the reaction was cooled to room temperature and quenched by careful addition of H$_2$O (0.323 mL), 1 N NaOH (0.646 mL) and H$_2$O (0.97 mL). This mixture was diluted with CH$_2$Cl$_2$ (25 mL) and stirred vigorously for 1 h and then filtered through a pad of celite®. The salts were washed with CH$_2$Cl$_2$ (5×25 mL) and the combined washings were concentrated by rotary evaporation to give the crude product as a yellow solid (0.597 g) which was purified by flash column chromatography by eluting with 1% MeOH/CH$_2$Cl$_2$ (+1% TEA) to give 4-aminomethyl-4-(4-iodo-phenyl)-piperidine-1-carboxylic acid tert-butyl ester (0.26 g, 26%). $^1$H NMR (CDCl$_3$): δ 7.81 (d, 2H), 7.17 (d, 2H), 3.82 (m, 2H), 3.145 (m, 2H), 2.86 (s, 2H), 2.24 (m, 2H), 1.80 (m, 2H), 1.65 (br.m, 2H), 1.56 (s, 9H).

A solution of 4-aminomethyl-4-(4-iodo-phenyl)-piperidine-1-carboxylic acid tert-butyl ester (0.26 g, 0.625 mmol) in THF (0.5 mL) was cooled to 0° C. Pyridine (0.055 mL, 0.69 mmol, 1.1 eq.) and trifluoroacetic anhydride (0.10 mL, 0.69 mmol, 1.1 eq.) were added and the reaction mixture was stirred at room temperature for 16 h. The solvent was removed by rotary evaporation and the resulting residue was dissolved in EtOAc (10 mL) and washed with saturated brine (3×10 mL). The combined organic extracts were dried over anhydrous Na$_2$SO$_4$, filtered and concentrated by rotary evaporation to give 4-(4-iodo-phenyl)-4-[(2,2,2-trifluoro-acetylamino)-methyl]-piperidine-1-carboxylic acid tert-butyl ester (0.298 g, 93%). $^1$H NMR (CDCl$_3$): δ 7.87 (d, 2H), 7.17 (d, 2H), 5.94 (m, 2H), 3.84 (m, 2H), 3.59 (m, 2H), 3.23 (m, 2H), 2.20 (m, 2H), 1.88 (m, 2H), 1.56 (s, 9H).

To a flask containing sodium hydride (0.07 g, 2.9 mmol, 5 eq.) under Ar at 0° C. was added a solution of 4-(4-iodo-phenyl)-4-[(2,2,2-trifluoro-acetylamino)-methyl]-piperidine-1-carboxylic acid tert-butyl ester (0.298 g, 0.58 mmol) in DMF (5 mL). The resulting mixture was warmed to room temperature and stirred for 2 h, heated to 35° C. for 0.5 h and CH$_3$I (0.36 mL, 5.8 mmol, 10 eq.) was added. The mixture heated at 35° C. for a further 2 h. The reaction was diluted with EtOAc (25 mL) and washed with saturated NaHCO$_3$ (25 mL) and saturated brine (25 mL). The combined organic extracts were dried over anhydrous Na$_2$SO$_4$, filtered and concentrated by rotary evaporation. The crude product was purified by flash column chromatography by eluting with 30% EtOAc/hexanes to give 4-(4-iodo-phenyl)-4-{[methyl-(2,2,2-trifluoro-acetyl)-amino]-methyl}-piperidine-1-carboxylic acid tert-butyl ester (0.022 g, 0.42 mmol, 72%). $^1$H NMR (CDCl$_3$): δ 7.83 (d, 2H), 7.20 (d, 2H), 3.93 (m, 2H), 3.78 (m, 1H), 3.53 (m, 1H), 3.07 (m, 2H), 2.60 (m, 3H), 2.24 (m, 2H), 1.93 (m, 2H), 1.54 (s, 9H).

4-(4-Iodo-phenyl)-4-{[methyl-(2,2,2-trifluoro-acetyl)-amino]-methyl}-piperidine-1-carboxylic acid tert-butyl ester (0.22 g, 0.42 mmol) was dissolved in MeOH (4.5 mL) and H$_2$O (0.6 mL) and K$_2$CO$_3$ (0.29 g, 2.1 mmol, 5 eq.) was added. The mixture was stirred and heated at 70° C. for 4 h, cooled to room temperature and then partitioned between H$_2$O (20 mL) and CH$_2$Cl$_2$ (20 mL). The aqueous layer was washed with CH$_2$Cl$_2$ (3×10 mL) and the combined organic washes were washed with saturated brine (10 mL) and dried over anhydrous Na$_2$SO$_4$, filtered and concentrated by rotary evaporation to give 4-(4-iodo-phenyl)-4-methylaminomethyl-piperidine-1-carboxylic acid tert-butyl ester (0.15 g, 83%). $^1$H NMR (CDCl$_3$): δ 7.78 (dd, 2H), 7.18 (dd, 2H), 3.74 (m, 2H), 3.22 (m, 2H), 2.73 (s, 2H), 2.38 (s, 3H), 2.23 (m, 2H), 1.88 (m, 2H), 1.54 (s, 9H).

4-(4-Iodo-phenyl)-4-methylaminomethyl-piperidine-1-carboxylic acid tert-butyl ester (0.15 g, 0.35 mmol) was dissolved in CH$_2$Cl$_2$ (2 mL) and 3,5-dichlorophenylisocyanate (0.066 g, 0.35 mmol, 1 eq.) was added. The reaction was stirred at room temperature for 6 h, diluted with CH$_2$Cl$_2$ (25 mL) and washed with saturated brine (25 mL). The aqueous layer was washed with CH$_2$Cl$_2$ (2×20 mL). The combined organic extracts were washed with saturated brine (20 mL), dried over anhydrous Na$_2$SO$_4$, filtered and concentrated by rotary evaporation to give 4-[3-(3,5-dichloro-phenyl)-1-methyl-ureidomethyl]-4-(4-iodo-phenyl)-piperidine-1-carboxylic acid tert-butyl ester (0.218 g, 100%). $^1$H NMR (CDCl$_3$): δ 7.84 (d, 2H), 7.24 (m, 3H), 7.09 (m, 2H), 6.23 (br.s, 1H), 3.96 (d, 2H), 3.54 (s, 2H), 2.99 (dd, 2H), 2.70 (s, 3H), 2.28 (d, 2H), 1.90m (dd, 3H), 1.54 (s, 9H).

To a solution of 4-[3-(3,5-dichloro-phenyl)-1-methyl-ureidomethyl]-4-(4-iodo-phenyl)-piperidine-1-carboxylic acid tert-butyl ester (0.218 g, 0.35 mmol) in CH$_2$Cl$_2$ (4.5 mL) at 0° C. was added TFA (1.5 mL, to give a 25% v/v solution). The reaction mixture was warmed to room temperature and stirred for 4 h. The solvent was removed by rotary evaporation and the residue was dissolved in EtOAc (25 mL) and washed with 10% aqueous NaHCO$_3$ (2×25 mL). The organic extracts were dried over anhydrous Na$_2$SO$_4$, filtered and concentrated by rotary evaporation to give 3-(3,5-dichloro-phenyl)-1-[4-(4-iodo-phenyl)-piperidin-4-ylmethyl]-1-methyl-urea (~0.19 g, 100%).

To a solution of 3-(3,5-dichloro-phenyl)-1-[4-(4-iodo-phenyl)-piperidin-4-ylmethyl]-1-methyl-urea (~0.10 g, 0.17 mmol) in ClCH$_2$CH$_2$Cl (1 mL) was added cyclopropanecarboxaldehyde (0.016 mL, 0.204 mmol, 1.2 eq.). The mixture was stirred at room temperature for 15 min and then HOAc (0.01 mL, 1% v/v) was added. The reaction was stirred for a further 1 h. Na(OAc)$_3$BH (0.054 g, 0.255 mmol, 1.5 eq.)

was added and the reaction was stirred at room temperature for 12 h. It was diluted with EtOAc (10 mL) and washed with saturated NaHCO$_3$ (10 mL) and saturated brine (10 mL). The combined organic extracts were dried over anhydrous Na$_2$SO$_4$, filtered and concentrated by rotary evaporation to give 1-[1-cyclopropylmethyl-4-(4-iodo-phenyl)-piperidin-4-ylmethyl]-3-(3,5-dichloro-phenyl)-1-methyl-urea (0.094 g, 95%). Crude $^1$H NMR (CDCl$_3$): δ 7.83 (d, 2H), 7.22 (m, 4H), 7.05 (s, 1H), 6.01 (br.s, 1H), 3.50 (s, 2H), 2.97 (d, 2H), 2.83 (s, 3H), 2.36 (m, 2H), 2.27 (m, 2H), 2.09 (m, 2H), 0.91 (br.m, 1H), 0.58 (d, 2H), 0.15 (d, 2H).

To a flask containing 1-[1-cyclopropylmethyl-4-(4-iodo-phenyl)-piperidin-4-ylmethyl]-3-(3,5-dichloro-phenyl)-1-methyl-urea (0.094 g, 0.164 mmol) was added Pd(PPh$_3$)$_4$ (0.02 g, 0.017 mmol, 10 mol %), 3-cyanophenylboronic acid (0.037 g, 0.25 mmol, 1.5 eq.) and Na$_2$CO$_3$ (0.212 g, 2 mmol). The mixture was suspended in toluene (3 mL), EtOH (1.5 mL) and H$_2$O (1 mL) and heated to 80° C. for 18 h. The reaction mixture was cooled to room temperature and partitioned between EtOAc (5 mL) and saturated Na$_2$CO$_3$ (5 mL). The organic layer was washed with saturated Na$_2$CO$_3$ (3×5 mL), saturated brine (3×5 mL), dried over anhydrous sodium sulfate, filtered and concentrated by rotary evaporation to give a brown solid which was purified by HPLC to give the title compound 1-[4-(3'-cyano-biphenyl-4-yl)-1-cyclopropylmethyl-piperidin-4-yl methyl]-3-(3,5-dichloro-phenyl)-1-methyl-urea (0.053 g, 60%). $^1$H NMR (300 MHz, CDCl$_3$): δ 7.95 (s, 1H), 7.92 (d, 1H), 7.79–7.66 (m, 4H), 7.57 (d, 2H), 7.41 (s, 2H), 7.33 (br.s, 1H), 7.06 (s, 1H), 3.76 (m, 2H), 3.63 (s, 1H), 3.60 (s, 2H), 3.08 (s, 3H), 2.87 (br.m, 2H), 2.69 (m, 5H), 1.14 (br.m, 1H), 0.84 (d, 2H), 0.44 (d, 2H)

EXAMPLE 15

4-(3'-Cyano-biphenyl-4-yl)-1-methyl-piperidine-4-carboxylic acid (3.5-dichloro-phenyl)-amide

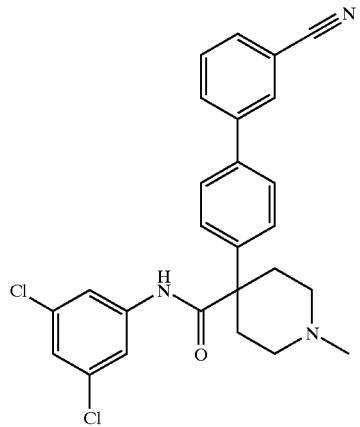

To a solution of 4-(4-iodo-phenyl)-1-methyl-piperidine-4-carboxylic acid pyridine salt (440 mg, 1.04 mmol, see Example 6) and 3,5-dichlorophenylaniline (0.20 g, 1.24 mmol, 1.2 eq.) in anhydrous DMF (5 mL) was added DIC (0.326 mL, 2.08 mmol, 2 eq.) followed by DMAP (0.006 g, 0.052 mmol, 5 mol %). The mixture was stirred at room temperature for 16 h and then it was partitioned between EtOAc (50 mL) and saturated aqueous NaHCO$_3$ (50 mL). The organic layer was separated, washed with H$_2$O (3×40 mL) and saturated brine (50 mL), dried over Na$_2$SO$_4$, filtered and concentrated by rotary evaporation. The crude material was purified by silica gel chromatography by eluting with 10% MeOH/EtOAc to give 175 mg (34%) of 4-(4-iodo-phenyl)-1-methyl-piperidine-4-carboxylic acid (3,5-dichloro-phenyl)-amide as a white solid. MS(ESI): 489.1/491.1.

To a flask containing 4-(4-iodo-phenyl)-1-methyl-piperidine-4-carboxylic acid (3,5-dichloro-phenyl)-amide (175 mg, 0.35 mmol) was added Pd(PPh$_3$)$_4$ (13 mg, 0.035 mmol, 10 mol %), 3-cyanophenylboronic acid (78 mg, 0.53 mmol, 1.5 eq.) and Na$_2$CO$_3$ (0.53 g, 5 mmol). The mixture was suspended in toluene (5 mL), EtOH (2.5 mL) and H$_2$O (2.5 mL) and heated at 90° C. for 18 h. The reaction mixture was cooled to room temperature and partitioned between EtOAc (10 mL) and saturated Na$_2$CO$_3$ (5 mL). The organic layer was washed with saturated Na$_2$CO$_3$ (3×5 mL), dried over anhydrous Na$_2$SO$_4$, filtered and concentrated by rotary evaporation. The crude product was purified by HPLC to give 4-(3'-cyano-biphenyl-4-yl)-1-methyl-piperidine-4-carboxylic acid (3,5-dichloro-phenyl)-amide as a white solid (0.066 g, 1.4 mmol, 14%). $^1$H NMR (300 MHz, CDCl$_3$): δ 7.95 (M, 1H), 7.91 (M, 1H), 7.62 to 7.76 (m, 6H), 7.51 (d, 2H), 7.19 (br, 1H), 7.15 (t, 1H), 2.71 (m, 6H), 2.42 (s, 3H), 2.30 (m, 2H). MS (ESI): 464.2/466.2 (M+1).

EXAMPLE 16

4-(3'-Cyano-biphenyl-4-yl)-1-methyl-piperidine-4-carboxylic acid 3,5-dichloro-benzylamide

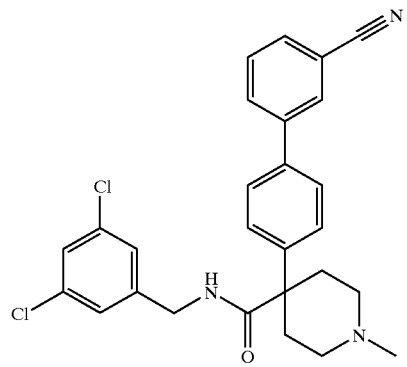

To a solution of 4-(4-iodo-phenyl)-1-methyl-piperidine-4-carboxylic acid pyridine salt (0.44 g, 1.04 mmol, see Example 6) and 3,5-dichlorobenzylamine (0.22 g, 1.24 mmol, 1.2 eq) in anhydrous DMF (5 mL) was added DIC (0.326 mL, 2.08 mmol, 2 eq) followed by DMAP (0.006 g, 0.052 mmol, 5%). The mixture was stirred at room temperature for 16 h and then it was partitioned between EtOAc (50 mL) and saturated aqueous NaHCO$_3$ (50 mL). The organic layer was separated, washed with H$_2$O (3×40 mL) and saturated brine (50 mL), dried over Na$_2$SO$_4$, filtered and concentrated by rotary evaporation. The crude material was purified by silica gel chromatography by eluting with 10% MeOH/EtOAc to give 60 mg (11%) of 4-(4-iodo-phenyl)-1-methyl-piperidine-4-carboxylic acid 3,5-dichloro-benzylamide as a white solid. MS(ESI): 503.1/505.1.

To a flask containing 4-(4-iodo-phenyl)-1-methyl-piperidine-4-carboxylic acid 3,5-dichloro-benzylamide (60 mg, 0.12 mmol) was added Pd(PPh$_3$)$_4$ (3.2 mg, 0.012 mmol, 10 mol %), 3-cyanophenylboronic acid (26.4 mg, 0.18 mmol, 1.5 eq.) and Na$_2$CO$_3$ (0.21 g, 2 mmol). The mixture was suspended in toluene (2 mL), EtOH (1 mL) and H$_2$O (1 mL) and heated at 90° C. for 18 h. The reaction mixture was cooled to room temperature and partitioned between EtOAc (10 mL) and saturated Na$_2$CO$_3$ (5 mL). The organic layer was washed with saturated Na$_2$CO$_3$ (3×5 mL), dried over anhydrous Na$_2$SO$_4$, filtered and concentrated by rotary evaporation. The crude product was purified by HPLC to give 4-(3'-cyano-biphenyl-4-yl)-1-methyl-piperidine-4-carboxylic acid 3,5-dichloro-benzylamide as a white solid (0.05 g, 0.0105 mmol, 10%). $^1$H NMR (300 MHz, CDCl$_3$): δ 7.88 (m, 2H), 7.71 (m, 3H), 7.52 (d, 2H), 7.31 (t, 1H), 7.00 (dd, 2H), 6.55 (t, 1H), 4.55 (br, 1H), 4.44 (d, 2H), 3.76 (m, 2H). 3.32 (m, 2H), 2.94 (s, 3H), 2.86 (m, 2H). 2.52 (t, 2H). MS (ESI): 478.1/480.1.

EXAMPLE 17

1-(3-Chloro-4-fluorophenyl)ureido-6-(3-cyanophenyl)-1'-methyl-spiro[indoline-3,4'-piperidine]

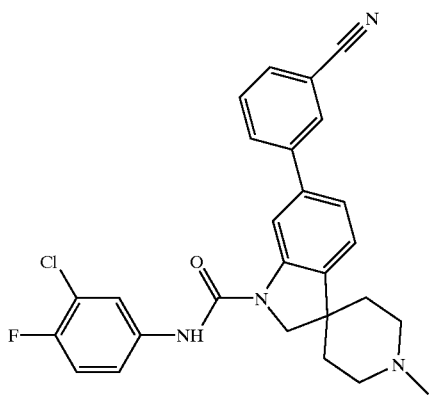

A solution of isonipecotic acid (12.9 g, 100 mmol) in 2N NaOH (55 mL) was cooled to 0° C. in an ice-bath. Benzylchloroformate (15.7 mL, 110 mmol, 1.1 eq.) and 2N NaOH (55 mL) were then added in about 10 portions, alternatively. The reaction mixture remained distinctly alkaline. The temperature of the reaction mixture was kept between 5 and 10° C. by controlling the rate of addition of reactants (about 45 min). The ice-bath was removed and the mixture was stirred at room temperature for 30 min. TLC showed the reaction was completed. The alkaline solution was extracted with Et$_2$O (4×50 mL). The aqueous layer was acidified using 6N HCl to pH ~5, extracted with EtOAc (3×100 mL). The combined EtOAc extracts were washed with saturated brine (100 mL), dried over Na$_2$SO$_4$, filtered and concentrated by rotary evaporation to give 1-benzyloxycarbonyl-piperidine-4-carboxylic acid as a white solid (17.3 g, 66 mmol, 66%). $^1$H NMR (300 MHz, CDCl$_3$): δ 7.35 (m, 5H), 5.14 (s, 2H), 4.12 (m, 2H), 2.97 (t, 2H), 2.53 (m, 1H), 1.95 (m, 2H), 1.68 (m, 2H).

SOCl$_2$ (9.62 mL, 132 mmol, 2 eq.) was carefully added to cold MeOH (130 mL) at −30° C. followed by the addition of 1-benzyloxycarbonyl-piperidine-4-carboxylic acid (17.3 g, 66 mmol) in one portion. The mixture was stirred at room temperature for 3 h then was bubbled with N$_2$ inside the hood and the resulting solution was concentrated by rotary evaporation. The residue was taken up into EtOAc (200 mL) and washed with saturated aqueous NaHCO$_3$ (200 mL) and saturated brine (100 mL) and the organic extracts were dried over Na$_2$SO$_4$, filtered and concentrated by rotary evaporation to give 1-benzyloxycarbonyl-piperidine-4-carboxylic acid methyl ester as a colorless oil (15 g, 54 mmol, 82%). $^1$H NMR (300 MHz, CDCl$_3$): δ 7.46 (m, 5H), 5.24 (s, 2H), 4.21 (m, 2H), 3.81 (s, 3H), 3.05 (t, 2H), 2.60 (m, 1H), 2.03 (m, 2H), 1.78 (m, 2H).

To a solution of 1-benzyloxycarbonyl-piperidine-4-carboxylic acid methyl ester (2.0 g, 7.2 mmol) in anhydrous toluene (20 mL) at −78° C. was added DIBAL-H (15.2 mL of a 1 M solution in hexane, 15.2 mmol, 2 eq.) in a drop-wise fashion. The mixture was stirred at −60° C. for 2 h then quenched by addition of 1 N HCl. The resulting mixture was extracted with EtOAc (3×50 mL) and the combined organic extracts were washed with saturated brine (50 mL) then dried over Na$_2$SO$_4$, filtered and concentrated by rotary evaporation. The crude residue was purified by flash column chromatography by eluting 9:1 toluene/EtOAc to give 1-benzyloxycarbonyl-piperidine-4-carboxaldehyde as a colorless gum (0.49 g, 2.09 mmol, 28%). $^1$H NMR (300 MHz, CDCl$_3$): δ9.75 (s, 1H), 7.46 (m, 5H), 5.24 (s, 2H), 4.15 (m, 2H), 3.12 (t, 2H), 2.54 (m, 1H), 2.02 (m, 2H), 1.68 (m, 2H).

A solution of TFA (10 mL of a 25% v/v solution in CH$_2$Cl$_2$) was degassed with a stream of Ar for 5 min. 3-Bromophenylhydrazine hydrochloride (0.492 g, 2.2 mmol, 1.1 eq.) was added and the mixture was heated to 40° C. A solution of 1-benzyloxycarbonyl-piperidine-4-carboxaldehyde (0.495 g, 2.0 mmol) in degassed CH$_2$Cl$_2$ (5 mL) was added drop-wise and the mixture was stirred at 40° C. for 18 h. The mixture was cooled to −10° C. and MeOH (5 mL) was added followed by NaBH$_4$ (0.115 g, 3 mmol) in small portions in order to keep the temperature below −2° C. The reaction mixture was stirred at −10° C. for 1 h and then quenched with 6% aqueous NH$_4$OH (4 mL). The organic layer was separated and the aqueous layer was extracted with CH$_2$Cl$_2$ (3×10 mL). The combined organic extracts were washed with saturated brine (20 mL) and dried over Na$_2$SO$_4$, filtered and concentrated by rotary evaporation. The crude material was purified by flash column chromatography by eluting 20–30% EtOAc/hexane. The high Rf compound was determined to be 6-bromo-1'-benzyloxycarbonyl-spiro[indoline-3,4'-piperidine] (0.11 g, 0.28 mmol, 14%). $^1$H NMR (300 MHz, CDCl$_3$): δ 7.50 (m, 5H), 6.96 (m, 2H), 6.86 (m, 1H), 5.28 (s, 2H), 4.26 (m, 2H), 3.60 (s, 2H), 3.09 (t, 2H), 1.84 (m, 4H). The low Rf compound was determined to be 4-bromo-1'-benzyloxycarbonyl-spiro[indoline-3,4'-piperidine] (0.15 g, 0.38 mmol, 19%). $^1$H NMR (300 MHz, CDCl$_3$): δ 7.50 (m, 5H), 6.97 (m, 2H), 6.65 (dd, 1H), 5.30 (s, 2H), 4.36 (m, 2H), 3.67 (s, 2H), 3.00 (m, 2H), 2.75 (m, 2H), 1.72 (m, 2H).

A mixture of 6-bromo-1'-benzyloxycarbonyl-spiro[indoline-3,4'-piperidine] (0.11 g, 0.27 mmol) and 3-chloro-4-fluorophenylisocyanate (0.034 mL, 0.27 mmol, 1 eq.) in CH$_2$Cl$_2$ (1.5 mL) was stirred at room temperature for 16 h. The mixture was concentrated by rotary evaporation to give the crude 1-(3-chloro-4-fluorophenyl)ureido-6-bromo-1'-benzyloxycarbonyl-spiro[indoline-3,4'-piperidine] as a yellowish solid (0.15 g, 0.051 mmol, 19%). $^1$H NMR (300 MHz, CDCl$_3$): δ 8.25 (dd, 1H), 7.75 (dd, 1H), 7.48 (m, 5H), 7.25 (m, 2H), 7.07 (d, 1H), 6.72 (s, 1H), 5.29 (s, 2H), 4.37 (m, 2H), 4.00 (s, 2H), 3.06 (m, 2H), 1.97 (m, 2H), 1.81 (m, 2H).

To a solution of crude 1-(3-chloro-4-fluorophenyl)ureido-6-bromo-1'-benzyloxycarbonyl-spiro[indoline-3,4'-piperidine] (~0.27 mmol) and Pd(PPh$_3$)$_4$ (0.011 g, 0.030 mmol, 10 mol %) in degassed toluene (5 mL) was added a solution of 3-cyanophenylboronic acid (0.067 g, 0.46 mmol, 1.7 eq.), aqueous Na$_2$CO$_3$ (2.5 mL of a 2N solution, 5 mmol), and EtOH (2.5 mL). The resulting mixture was heated at 90° C. for 16 h then partitioned between EtOAc (20 mL) and 10% aqueous NaHCO$_3$ (20 mL). The organic phase was separated and washed with 10% aqueous NaHCO$_3$ (3×10 mL) and saturated brine (10 mL), dried over Na$_2$SO$_4$, filtered and concentrated by rotary evaporation. The crude residue was purified by flash column chromatography by eluting 10–20% EtOAc/hexane to give 1-(3- chloro-4-fluorophenyl)ureido-6-(3-cyanophenyl)-1'-benzyloxycarbonyl-spiro[indoline-3,4'-piperidine] as a yellowish oil (0.057 g, 0.097 mmol, 36%). $^1$H NMR (300 MHz, CD$_3$OD): δ 7.23 to 8.31 (m, 15H), 5.27 (s, 2H), 4.32 (d, 2H), 4.21 (s, 2H), 3.17 (m, 2H), 1.98 (m, 2H), 1.82 (m, 2H).

A solution of TFA (1.5 mL) and methyl sulfide (0.5 mL) was carefully added to 1-(3-chloro-4-fluorophenyl)ureido-6-(3-cyanophenyl)-1'-benzyloxycarbonyl-spiro[indoline-3,4'-piperidine] (0.054 g, 0.09 mmol) and the resulting mixture was stirred at room temperature for 16 h. The mixture was concentrated by rotary evaporation and the resulting residue was dissolved in EtOAc (10 mL) and washed with 10% aqueous NaHCO$_3$ (3×5 mL), saturated brine (5 mL) then dried over Na$_2$SO$_4$, filtered and concentrated to give 1-(3-chloro-4-fluorophenyl)ureido-6-(3-cyanophenyl)-spiro[indoline-3,4'-piperidine] as a yellow oil (0.037 g, 0.081 mmol, 90%). $^1$H NMR (300 MHz, CD$_3$OD): δ 8.44 (m, 2H), 8.06 (m, 2H), 7.82 (m, 2H), 7.70 (m, 2H), 7.37 (m, 2H), 4.35 (s, 2H), 3.53 (m, 2), 3.04 (t, 2H), 2.28 (m, 2H), 1.99 (m, 2H).

To a solution of 1-(3-chloro-4-fluorophenyl)ureido-6-(3-cyanophenyl)-spiro[indoline-3,4'-piperidine] (0.037 g, 0.08 mmol) in ClCH$_2$CH$_2$Cl (0.5 mL) was added formaldehyde (0.03 mL of a 37% aqueous solution, 0.40 mmol, 5 eq.). The reaction was stirred at room temperature for 1 h then Na(OAc)$_3$BH (0.042 g, 0.20 mmol, 2.5 eq.) was added and the resulting mixture was stirred at room temperature for 16 h. The mixture was partitioned between EtOAc (10 mL) and 10% aqueous NaHCO$_3$ (5 mL) and the organic phase was washed with 10% aqueous NaHCO$_3$ (2×5 mL), saturated brine (5 mL), then dried over Na$_2$SO$_4$, filtered and concentrated by rotary evaporation. The crude product was purified by HPLC to give the title compound 1-(3-chloro-4-fluorophenyl)ureido-6-(3-cyanophenyl)-1' methyl-spiro[indoline-3,4'-piperidine] as a colorless gum (0.0128 g, 0.0304 mmol, 34%). $^1$H NMR (300 MHz, CD$_3$OD): δ 8.32 (s, 1H), 8.06 (m, 2H), 7.88 (dd, 1H), 7.82 (m, 1H), 7.73 (m, 1H), 7.57 (m, 1H), 7.46 (s, 2H), 7.32 (t, 1H), 4.33 (s, 2H), 3.78 (dd, 2H), 3.29 (m, 2H), 3.10 (s, 3H), 2.38 (m, 2H), 2.20 (dd, 2H). MS (ESI): 475.2 (M+1), 477.1 (M+3).

MCH Assay PCOP Protocol:

A reaction mixture of 10 μg hMCHR-CHO overexpressing membranes (from Receptor Biology, Inc., Beltville, Md., or internally produced) and 100 μg/well WGA-SPA beads (from Amersham Pharmacia Biotech, Inc., Piscataway, N.J.)/100 μL was prepared in MCHR assay buffer (25 mM HEPES, pH 7.4, 10 mM NaCl, 10 mM MgCl$_2$, 5 mM MnCl$_2$, 0.1%BSA). A 2.0 nM stock of ligand, [$^{125}$I]-MCH (from Perkin Elmer Life Sciences, Inc., Boston, Mass.) was prepared in the MCHR assay buffer. 40×stock solutions of test compounds were prepared in DMSO and then added to a 96-well assay plate (Corning #3604, Corning, N.Y.) as follows: 5 μL test compound, NSB compound or DMSO, 45 μL MCHR assay buffer, 100 μL of reaction mixture, 50 μL of ligand stock (Final [Ligand]=0.5 nM). The assay plates were shaken for 5 minutes on a plate shaker, then incubated for 2 hours before cpm/well were determined in a Microbeta Trilux counter (from Perkin Elmer Wallac, Inc., Gaithersburg, Md.). Percent inhibition of total binding-nonspecific binding (2.5 μM MCH) was determined for IC$_{50}$ values.

TABLE 1

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
| --- | --- | --- | --- | --- |
| 7 | | 534.1953 | 534.2/535.2 | B |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---------|-----------|-----------------|----------------|----------|
| 8 | | 532.1796 | 533.2/535.2 | A |
| 9 | | 460.2074 | 461.2/462.2 | A |
| 10 | | 499.2435 | 500.3/501.3 | C |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 11 | | 537.1653 | 538.2/539.2 | C |
| 12 | | 445.2729 | 446.3/447.3 | C |
| 13 | | 486.2231 | 487.2/488.2 | B |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 14 | | 546.1953 | 547.1/549.1 | A |
| 15 | | 463.1218 | 464.2/466.2 | C |
| 16 | | 477.1374 | 478.1/480.1 | C |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 17 | | 474.1622 | 475.2/477.1 | C |
| 18 | | 532.1102 | 532.11/533.3 | B |
| 19 | | 468.1483 | 469.1/471.0 | A |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 20 | | 522.1953 | 523.1/525.2 | A |
| 21 | | 454.1327 | 454.8 | B |
| 22 | | 405.1374 | 406.1/408.0 | C |
| 23 | | 391.1218 | 392.0/394.0 | C |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---------|-----------|-----------------|----------------|----------|
| 24 | | 425.0828 | 426.0/428.1 | C |
| 25 | | 445.1687 | 446.1/448.1 | C |
| 26 | | 459.1844 | 460.2/462.1 | C |
| 27 | | 433.1687 | 434.1/436.2 | C |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
| --- | --- | --- | --- | --- |
| 28 | | 460.2074 | 450.2/451.3 | A |
| 29 | | 484.1432 | 484.1/485.1 | B |
| 30 | | 436.2074 | 437.3/438.3 | B |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 31 | | 585.1368 | 585.1/586.0 | B |
| 32 | | 449.2215 | 450.2/451.3 | A |
| 33 | | 555.1691 | 555.1/556.1 | B |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---|---|---|---|---|
| 34 | 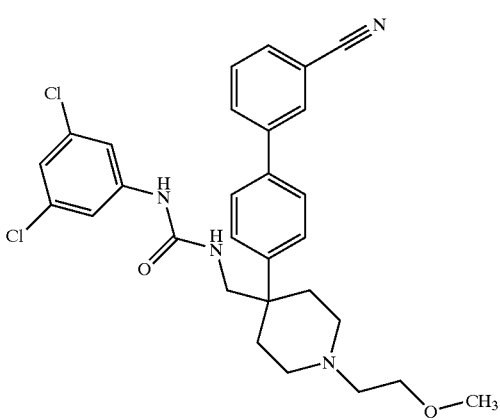 | 536.1745 | 536.1/537.2 | A |
| 35 | 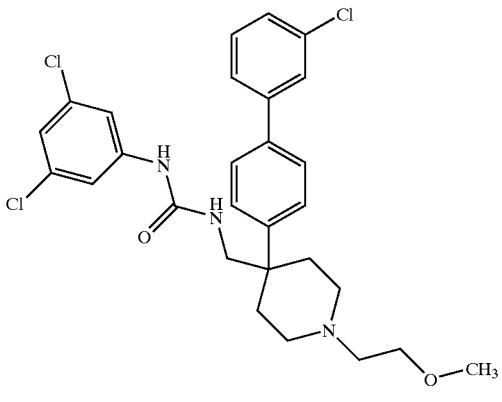 | 545.1403 | 545.1/546.1 | A |
| 36 | 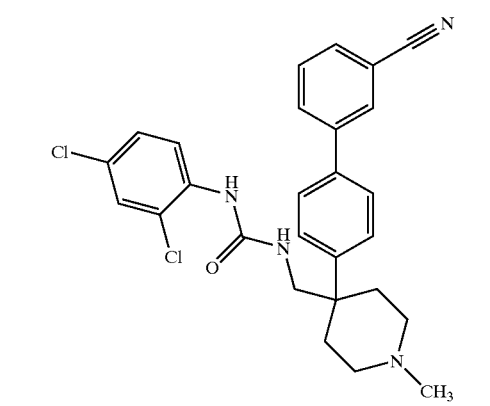 | 492.1483 | 493.1/495.1 | B |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---|---|---|---|---|
| 37 | 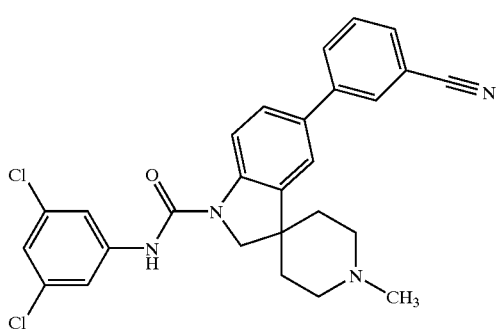 | 490.1327 | 491.2/493.1 | B |
| 38 | 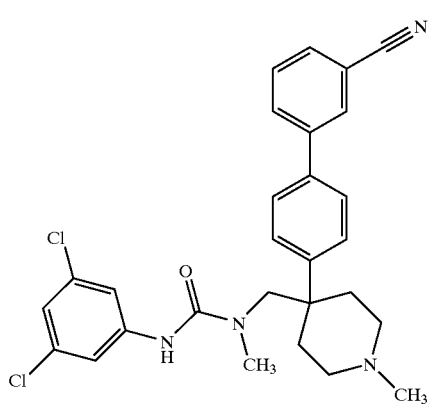 | 506.1640 | 507.0/509.1 | A |
| 39 | 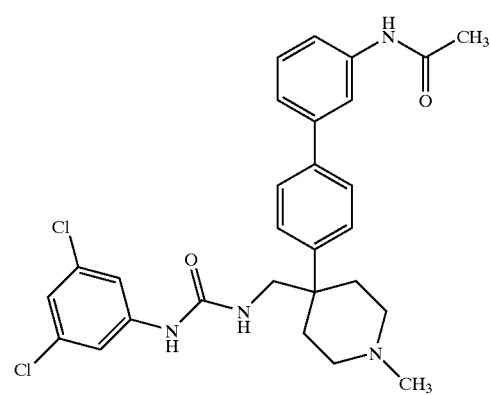 | 524.1745 | 524.1/525.2 | A |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---------|-----------|-----------------|----------------|----------|
| 40 | | 507.1480 | 507.1/508.2 | C |
| 41 | | 482.1640 | 482.1/483.1 | B |
| 42 | | 495.1480 | 495.1/496.2 | A |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 43 | | 511.1429 | 511.1/512.2 | A |
| 44 | | 498.1589 | 498.1/499.2 | B |
| 45 | | 518.1640 | 519.2/521.2 | C |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---------|-----------|-----------------|----------------|----------|
| 46 | 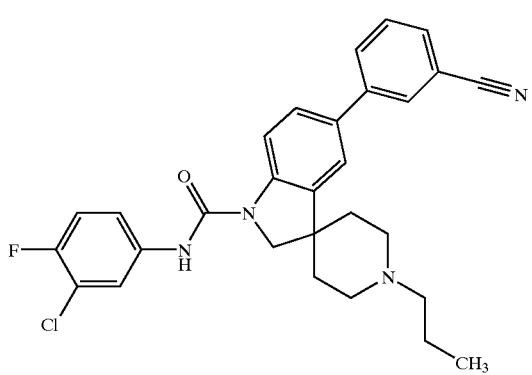 | 502.1935 | 503.2/505.2 | C |
| 47 | 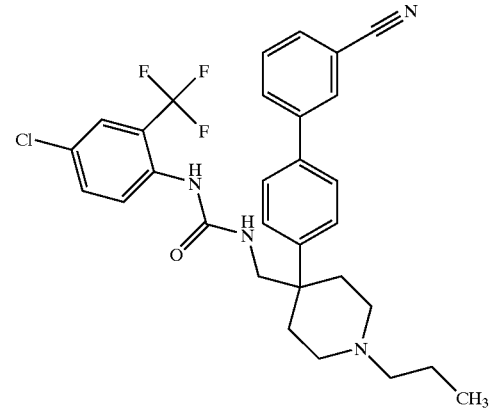 | 554.2060 | 555.2/557.2 | B |
| 48 | 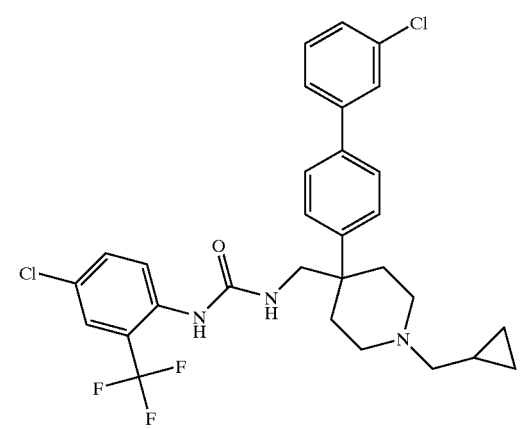 | 575.1718 | 576.2/578.2 | C |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---------|-----------|-----------------|----------------|----------|
| 49 | | 525.1750 | 526.2/528.2 | A |
| 50 | | 566.2060 | 567.2/569.2 | A |
| 51 | | 535.1405 | 536.2/538.1 | A |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 52 | | 563.1718 | 564.2/566.2 | C |
| 53 | | 477.1374 | 478.2/480.2 | B |
| 54 | | 424.2263 | 425.2/426.2 | A |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 55 | | 469.1732 | 470.2/472.2 | A |
| 56 | | 526.1747 | 527.2/529.2 | A |
| 57 | | 535.1405 | 536.2/538.2 | B |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 58 | | 563.1718 | 564.2/566.2 | C |
| 59 | | 535.1405 | 536.1/538.2 | C |
| 60 | | 566.2060 | 567.2/569.2 | C |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---------|-----------|-----------------|----------------|----------|
| 61 | 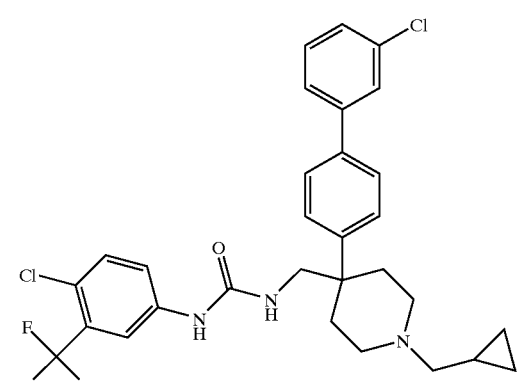 | 575.1718 | 576.2/578.2 | B |
| 62 | 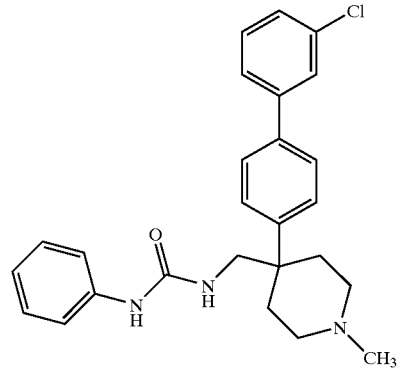 | 433.1921 | 434.2 | A |
| 63 | 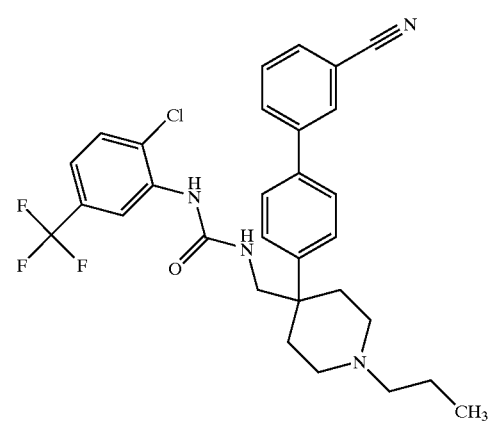 | 554.2060 | 555.2/557.2 | B |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 64 | | 563.1718 | 564.2/566.2 | B |
| 65 | | 504.2092 | 505.2/507.2 | A |
| 66 | | 520.1796 | 521.2/523.2 | A |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---------|-----------|-----------------|----------------|----------|
| 67 | | 526.1747 | 527.2/529.2 | C |
| 68 | | 566.2060 | 567.2/569.2 | B |
| 69 | | 526.1747 | 527.2/529.2 | B |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 70 | | 541.1454 | 544.1/546.1 | A |
| 71 | | 554.2060 | 555.2/557.2 | A |
| 72 | | 486.1032 | 487.2/491.1 | C |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 73 | | 575.1718 | 576.2/578.2 | C |
| 74 | | 529.1454 | 530.2/534.1 | A |
| 75 | | 474.1622 | 475.2/477.1 | C |
| 76 | | 501.1141 | 501.1/502.2 | A |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---------|-----------|-----------------|----------------|----------|
| 77 | 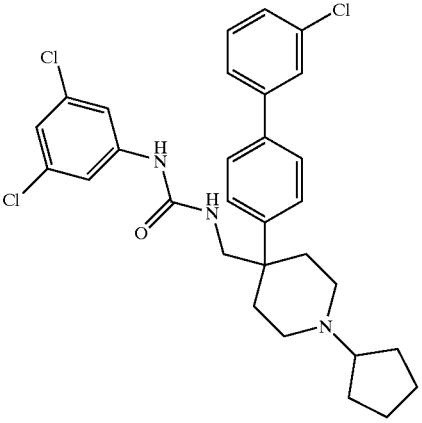 | 555.1611 | 555.1/556.2 | A |
| 78 | 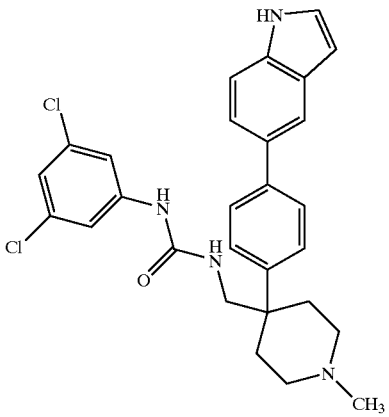 | 506.1640 | 506.1/507.2 | C |
| 79 | 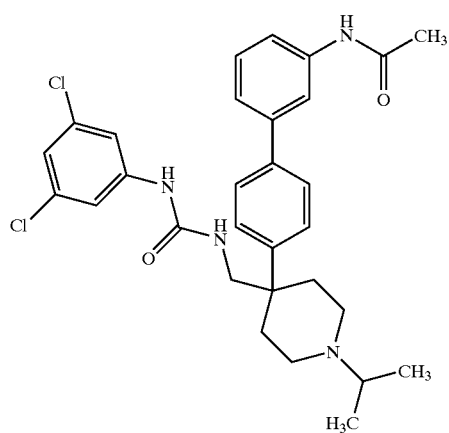 | 552.2058 | 552.2/553.1 | A |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 80 | | 537.1950 | 537.1/538.2 | B |
| 81 | | 565.1899 | 565.1/566.2 | A |
| 82 | | 539.1742 | 539.1/540.2 | A |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 83 | | 529.1454 | 529.1/530.2 | A |
| 84 | | 520.1796 | 520.1/521.2 | A |
| 85 | | 546.1953 | 546.2/547.3 | A |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---|---|---|---|---|
| 86 | 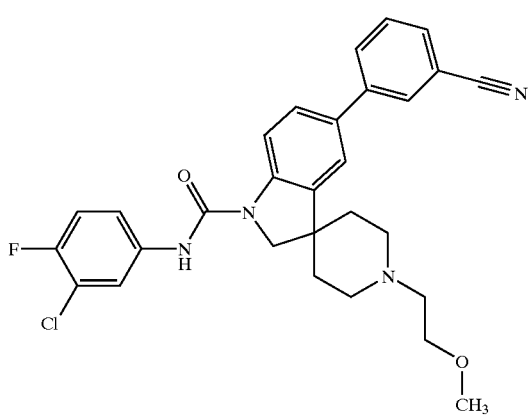 | 518.1884 | 519.2/521.2 | C |
| 87 | 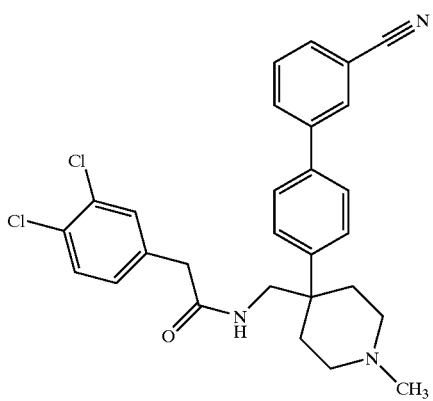 | 491.1531 | 492.2/494.2 | B |
| 88 | 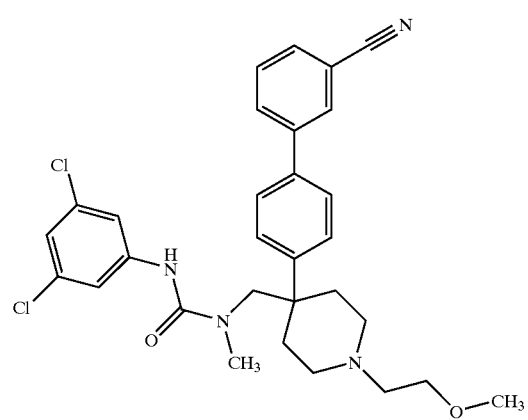 | 550.1902 | 551.1/553.1 | A |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---------|-----------|-----------------|----------------|----------|
| 89 | 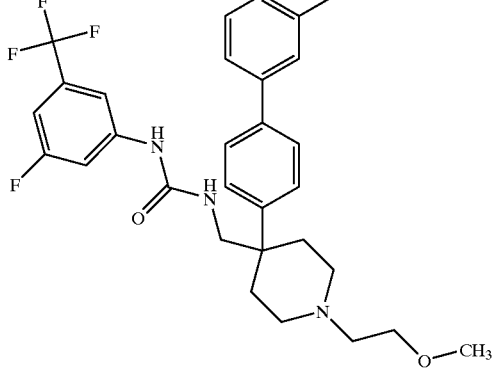 | 554.2304 | 554.2/555.2 | A |
| 90 | 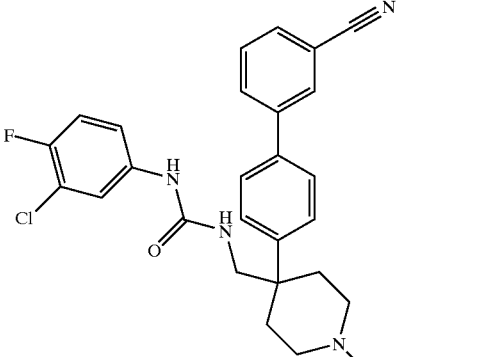 | 520.2041 | 520.2/521.1 | A |
| 91 | 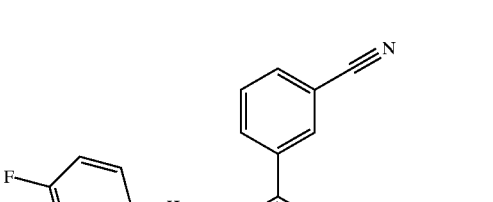 | 504.2337 | 504.2/505.2 | A |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---|---|---|---|---|
| 92 | 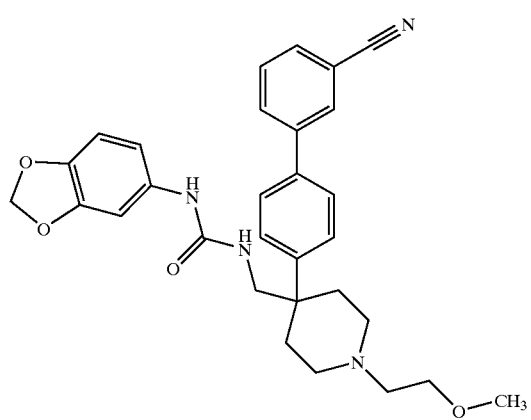 | 512.2423 | 512.2/513.2 | A |
| 93 | 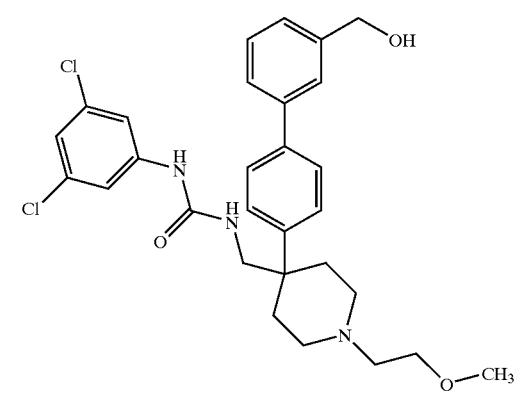 | 541.1899 | 541.1/542.1 | A |
| 94 | 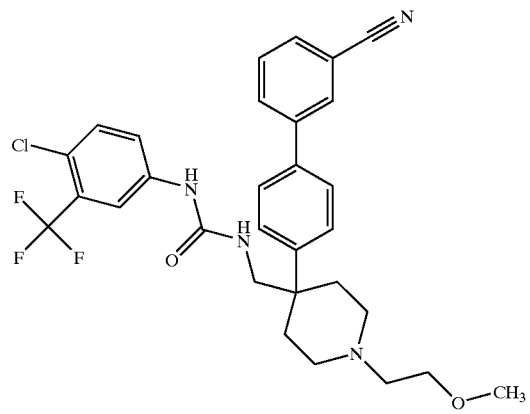 | 570.2009 | 570.2/571.2 | A |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 95 | | 532.2241 | 532.2/533.1 | B |
| 96 | | 500.2387 | 501.3 | A |
| 97 | | 514.2544 | 581.2/583.2 | B |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---|---|---|---|---|
| 98 | 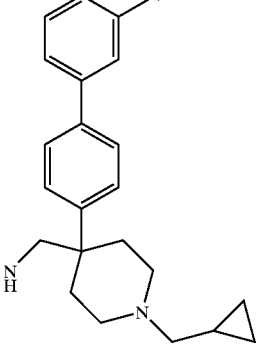 | 508.2474 | 509.2 | B |
| 99 | 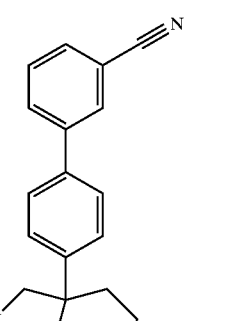 | 530.2248 | 531.2/533.1 | B |
| 100 | 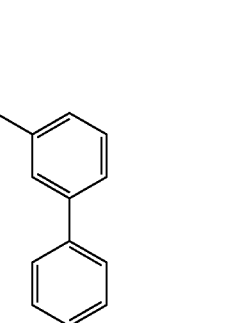 | 550.2355 | 551.3 | A |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---------|-----------|-----------------|----------------|----------|
| 101 | 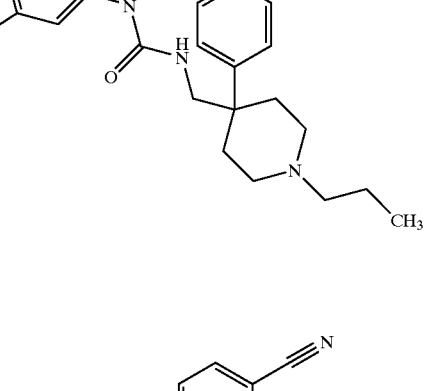 | 496.2474 | 497.2 | B |
| 102 | 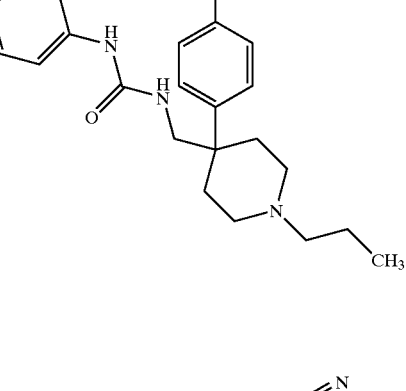 | 488.2387 | 489.2 | A |
| 103 | 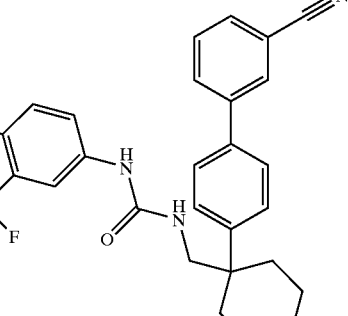 | 538.2355 | 539.2 | A |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---------|-----------|-----------------|----------------|----------|
| 104 | | 580.2216 | 515.2/516.3 | B |
| 105 | | 504.2337 | 504.2/505.2 | A |
| 106 | | 566.2215 | 566.2/567.2 | C |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---------|-----------|-----------------|----------------|----------|
| 107 | 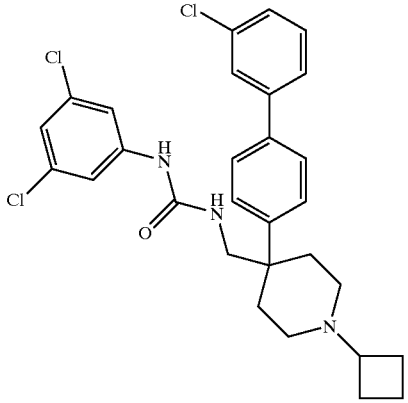 | 541.1454 | 541.1/542.2 | C |
| 108 | 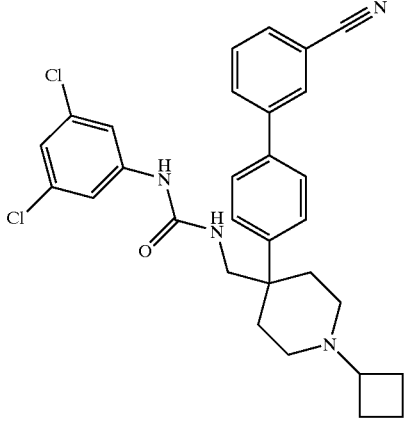 | 532.1796 | 532.1/533.2 | B |
| 109 | 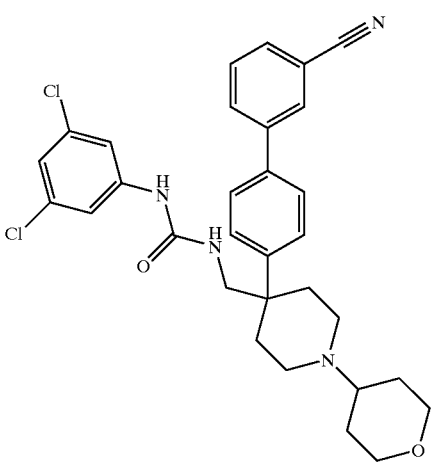 | 562.1902 | 562.1/563.1 | A |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---|---|---|---|---|
| 110 | 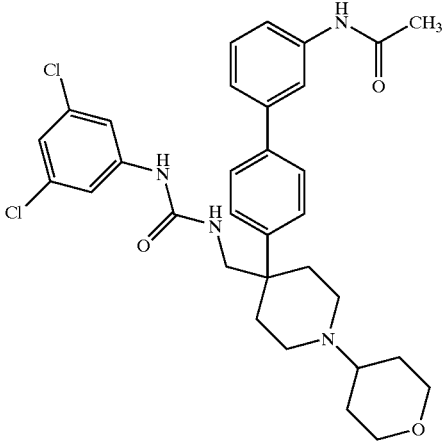 | 594.2164 | 594.2/595.1 | B |
| 111 | 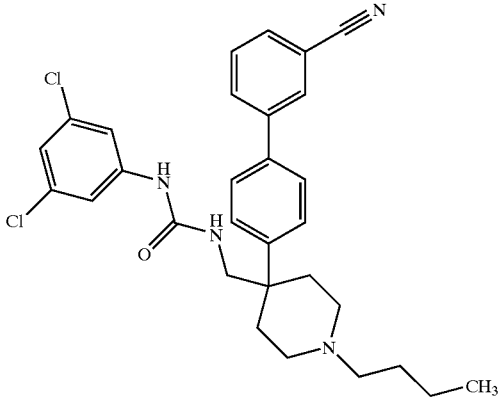 | 534.1953 | 534.2/535.2 | B |
| 112 | 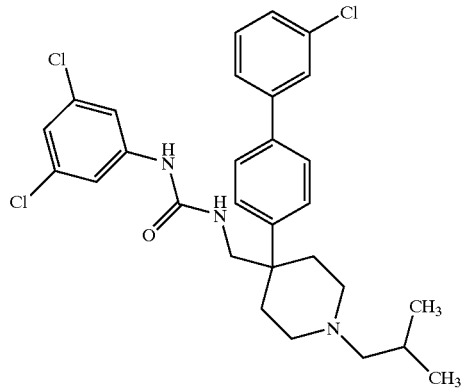 | 543.1611 | 543.1/544.1 | B |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 113 | | 543.1611 | 543.1/544.1 | B |
| 114 | | 571.1560 | 571.1/572.1 | C |
| 115 | | 513.1044 | 514.2/516.2 | C |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 116 | | 492.1483 | 493.2/495.2 | A |
| 117 | | 558.1809 | 559.2/561.2 | A |
| 118 | | 574.1514 | 575.2/577.1 | A |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 119 | | 506.1640 | 506.1/507.2 | A |
| 120 | | 569.1767 | 569.1/570.2 | A |
| 121 | | 515.1298 | 515.1/516.1 | B |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---|---|---|---|---|
| 122 | 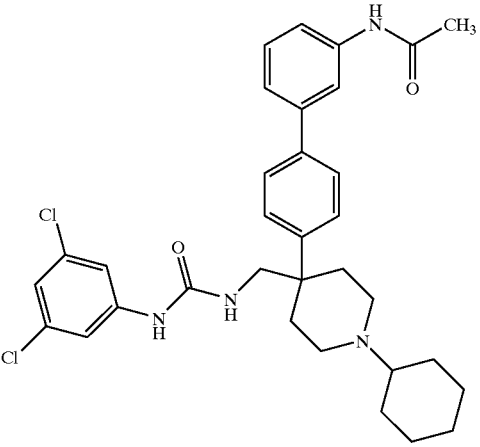 | 592.2371 | 592.2/593.2 | A |
| 123 | 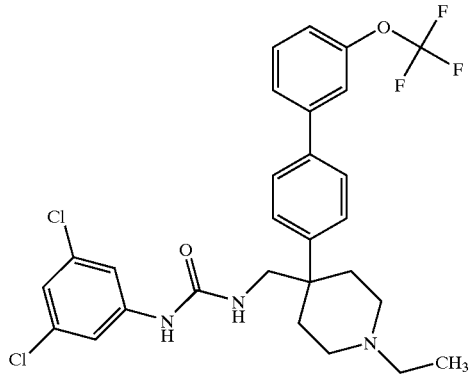 | 565.1510 | 565.1/566.1 | B |
| 124 | 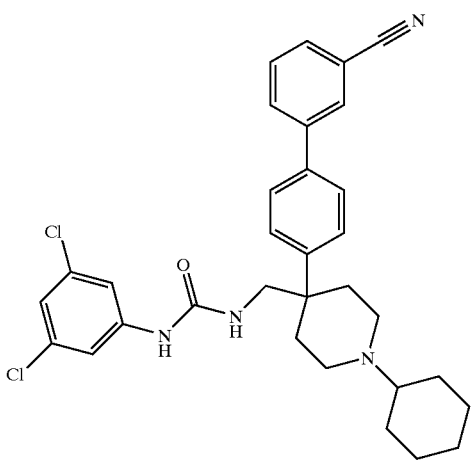 | 560.2109 | 560.2/561.2 | A |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---------|-----------|-----------------|----------------|----------|
| 125 | 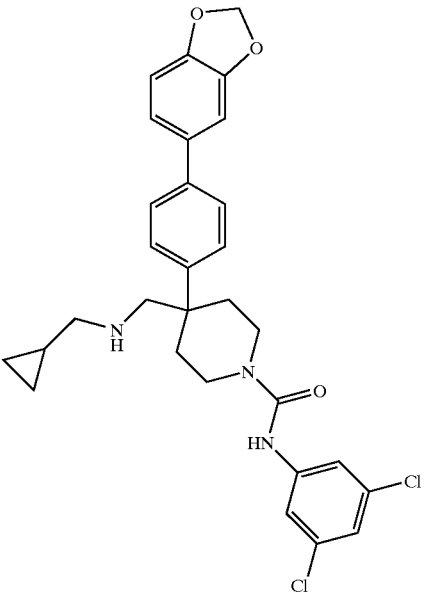 | 551.1742 | 551.1/552.1 | C |
| 126 | 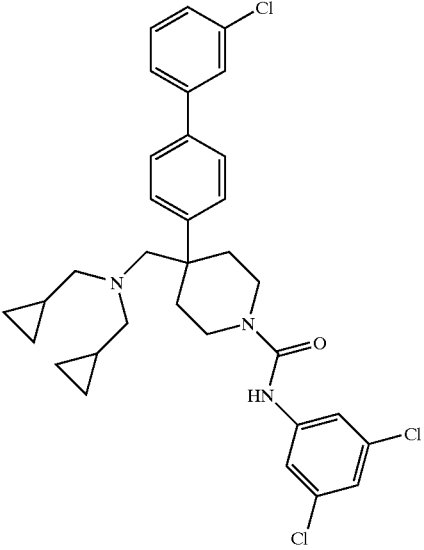 | 595.1924 | 595.1/596.2 | C |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---|---|---|---|---|
| 127 | 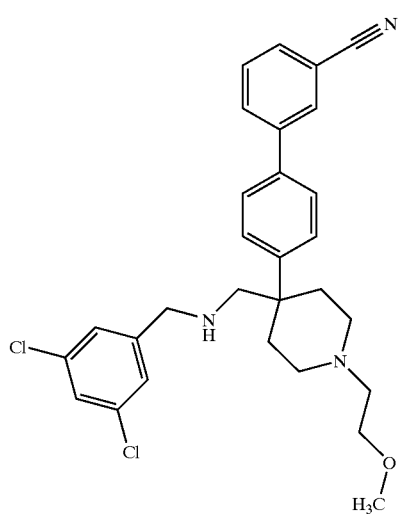 | 507.1844 | 507.1/508.1 | C |
| 128 | 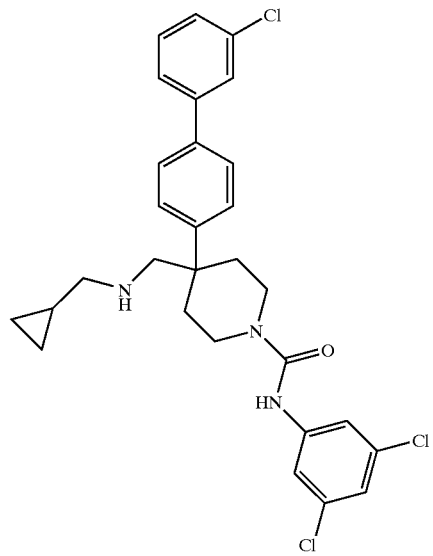 | 541.1454 | 541.1/542.1 | C |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---|---|---|---|---|
| 129 | 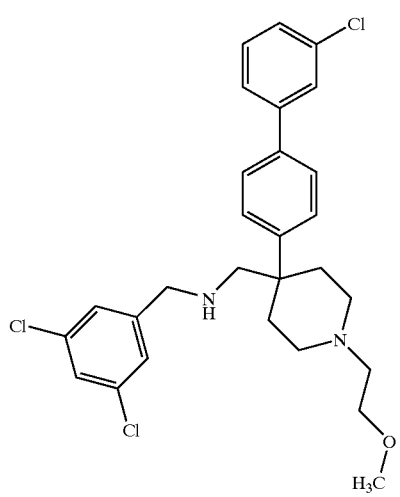 | 516.1502 | 516.1/517.1 | C |
| 130 | 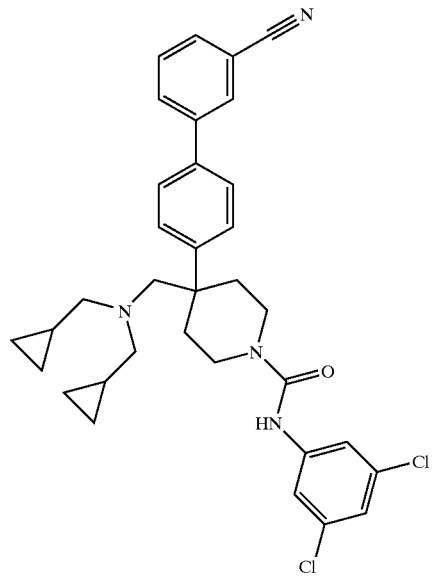 | 586.2266 | 586.2/587.2 | C |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---------|-----------|-----------------|----------------|----------|
| 131 | 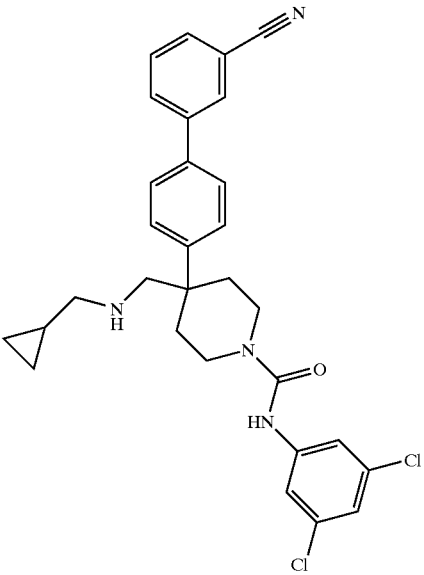 | 532.1796 | 532.18/533.1 | B |
| 132 | 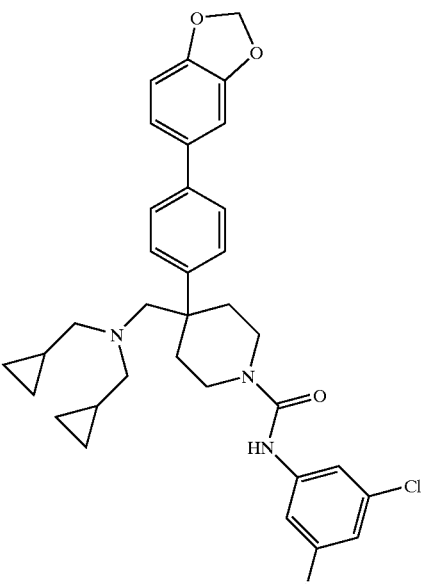 | 605.2212 | 605.2/606.1 | C |

TABLE 1-continued
MCH Active Compounds: A (Ki = 0.2–10 nM), B (Ki = 11–100 nM), C (Ki = 101–5500 nM).
| Example | Chemistry | Exact MS, calc. | MS (ESI) found | Activity |
|---------|-----------|-----------------|----------------|----------|
| 133 | 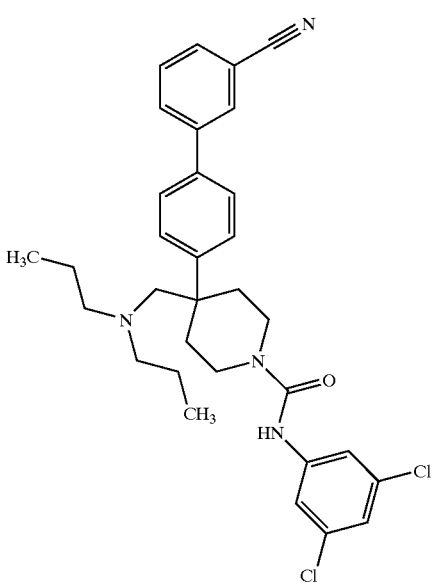 | 562.2266 | 562.2/563.2 | C |
| 134 | 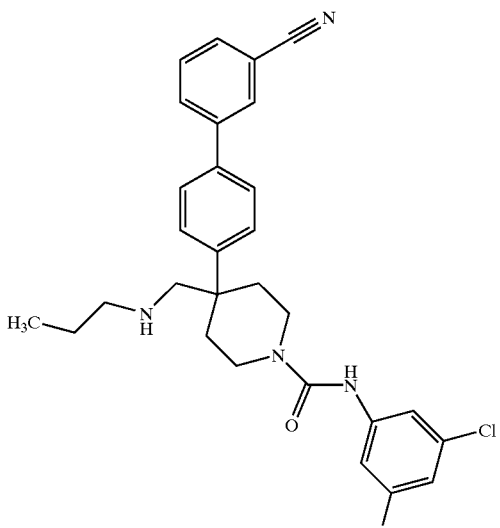 | 520.1796 | 520.1/521.1 | B |

TABLE 1-continued

MCH Active Compounds: A (Ki = 0.2–10 nM), B (Ki = 11–100 nM), C (Ki = 101–5500 nM).

| Example | Chemistry | Exact MS, calc. | MS (ESI) found | Activity |
|---|---|---|---|---|
| 135 | 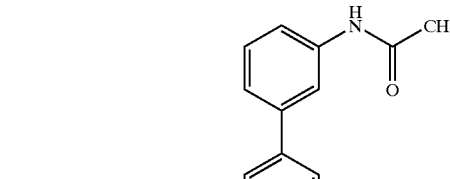 | 539.2106 | 539.2/540.1 | C |

What is claimed is:

1. A compound, including enantiomers, stereoisomers, rotamers, tautomers, and racemates of said compound, and pharmaceutically acceptable salts or solvates of said compound, said compound having the general structure shown in Formula I:

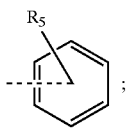

I wherein:

$Ar^1$:

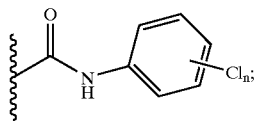

Z is a moiety selected from the group consisting of $R_4CO$—; $R_4SO_2$—; $R_4N(R^{2'})CO$—; $R^{4'}$—; and $R^{4'}$—O—C(O)—;

$R_2$ is H; alkyl; or alkyl (substituted with cycloalkyl);

$R^{2'}$ is H or alkyl;

$R_3$ is a moiety selected from the group consisting of H; alkyl; cycloalkyl; alkyl substituted with cycloalkyl; alkyl substituted with alkoxy; alkyl substituted with $CF_3$; arylalkyl; alkylaryl; tetrahydrofuranyl; tetrahydropyranyl; $R_8SO_2$—; and $$\text{image of } -C(O)-NH-phenyl-Cl_n$$

n is a number 1 to 5;

$R_4$ is phenyl substituted with $R_7$ or phenylalkyl substituted on the phenyl with $R_7$;

$R^{4'}$ is a moiety selected from the group consisting of H; alkyl; cycloalkyl; alkyl substituted with cycloalkyl; alkyl substituted with alkoxy; alkyl substituted with $CF_3$; arylalkyl; alkylaryl; tetrahydrofuranyl; and tetrahydropyranyl;

$R_5$ numbers 1–4 which may be the same or different and are independently selected from phenyl substituted with $R_7$;

$R_7$ numbers 1–3 which may be the same or different and are independently selected from the group consisting of H; halogen; alkyl; OH; alkoxy; $NH_2$, NH-alkyl; $N(alkyl)_2$; CN; $CF_3$; $NO_2$; $CF_3O$; —NH—C(O)-alkyl; —CH(O); —methylenedioxy; —$CH_2OH$; benzofuran-2-yl; —O(alkyl); —C(O)alkyl; and indolyl; and $R_8$ is selected from the group consisting of alkyl; arylalkyl; alkylaryl; aryl; —NH(alkyl); and —$N(alkyl)_2$.

2. The compound of claim 1, wherein said $R_5$ on $Ar^1$ is at the 4-position of said phenyl or pyridyl with respect to the attachment of $Ar^1$ to the benzylic position shown in Formula I.

3. The compound of claim 2, wherein said $R_7$ on $R_5$ is at the 3-position of said phenyl.

4. The compound of claim 1, wherein $R_7$ is selected from the group consisting of halogen, CN, $CF_3$, $NO_2$ and methylenedioxy.

5. The compound of claim 4, wherein $R_7$ is CN or Cl.

6. The compound of claim 1, wherein Z is $R_4N(R^{2'})CO$—.

7. The compound of claim 1, wherein $R_2$ is H.

8. The compound of claim 1, wherein $R^{2'}$ is H.

9. The compound of claim 1, wherein $R_3$ is selected from the group consisting of alkyl, cycloalkyl, tetrahydrofuranyl and tetrahydropyranyl.

10. The compound of claim 1, wherein $R_4$ is a phenyl substituted with $R_7$, with $R_7$ being defined in claim 1.

11. The compound of claim 1 with the structure:

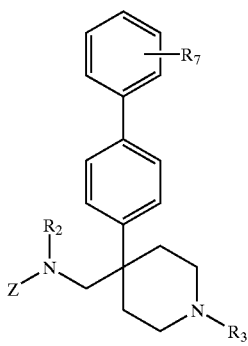

wherein Z, $R_2$, $R_3$ and $R_7$ are as defined in claim 1.

12. A compound, including enantiomers, stereoisomers, rotamers, tautomers, and racemates of said compound, and pharmaceutically acceptable salts, said compound having the general structure shown in Formula II:

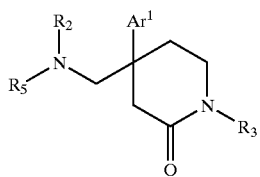

wherein:

$Ar^1$ is

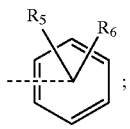

$R_2$ is H; alkyl; or alkyl substituted with cycloalkyl;

$R_3$ is a moiety selected from the group consisting of H; alkyl; cycloalkyl; alkyl substituted with cycloalkyl; alkyl substituted with alkoxy; alkyl substituted with $CF_3$; arylalkyl; alkylaryl; tetrahydrofuranyl; tetrahydropyranyl; $R_8SO_2$—; and

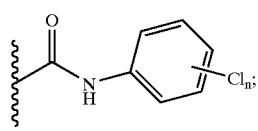

n is a number from 1 to 5;

$R_4$ is phenyl substituted with $R_7$ or phenylalkyl substituted on the phenyl with $R_7$;

$R_5$ numbers 1–4 which may be the same or different and are independently selected from the group consisting of $R_7$; phenyl substituted with $R_7$; pyridyl substituted with $R_7$; thiophenyl substituted with $R_7$; pyrimidinyl substituted with $R_7$; pyridazinyl substituted with $R_7$; and pyrazinyl substituted with $R_7$ as well as the N-oxides of the above-noted pyridyl, pyrimidinyl, pyridazinyl and pyrazinyl;

$R_6$ numbers 1–4 numbers 1–4 which may be the same or different and are independently selected from the group consisting of H; halogen; alkyl; OH; alkoxy; $NH_2$; NH-alkyl; $N(alkyl)_2$; CN; $CF_3$; $NO_2$; and $CF_3O$;

$R_7$ numbers 1–3 which may be the same or different and are independently selected from the group consisting of H; halogen; alkyl; OH; alkoxy; $NH_2$, NH-alkyl; $N(alkyl)_2$; CN; $CF_3$; $NO_2$; $CF_3O$; —NH—C(O)-alkyl; —CH(O); -methylenedioxy; —$CH_2OH$; benzofuran-2-yl; —O(alkyl); —C(O)alkyl; and indolyl; and $R_8$ is selected from the group consisting of alkyl; arylalkyl; alkylaryl; aryl; —NH(alkyl); and —$N(alkyl)_2$.

13. The compound of claim 12, wherein $Ar^1$ is phenyl substituted with $R_5$ in the 4-position.

14. The compound of claim 13, wherein $R_5$ is a phenyl substituted with $R_7$.

15. The compound of claim 14, wherein said $R_7$ is at the 3-position of said phenyl.

16. The compound of claim 12, wherein $R_7$ is CN or Cl.

17. The compound of claim 12, wherein $R_2$ is H.

18. The compound of claim 12, wherein $R_3$ is selected from the group consisting of alkyl, cycloalkyl, tetrahydrofuranyl and tetrahydropyranyl.

19. The compound of claim 12, wherein $R_4$ is a phenyl substituted with $R_7$, with $R_7$ being defined in claim 12.

20. A pharmaceutical composition comprising as an active ingredient therapeutically effective amounts of at least one compound of claim 1 or claim 12.

21. The pharmaceutical composition of claim 20 wherein the therapeutically effective amount is for use in treating obesity.

22. The pharmaceutical composition of claim 21 additionally comprising a pharmaceutically acceptable carrier.

23. A method of treating obesity, said method comprising administering to a patient in need of such treatment a pharmaceutical composition which composition comprises therapeutically effective amounts of at least one compound of claim 1 or of claim 12.

24. The method of claim 23, wherein said administration is oral.

25. The method of claim 23, wherein said administration is via subcutaneous administration.

26. A compound exhibiting MCH modulatory activity, including enantiomers, stereoisomers, rotamers, tautomers, and racemates of said compound, and pharmaceutically acceptable salts or solvates of said compound, said compound being selected from the group of compounds with structures listed below:

137
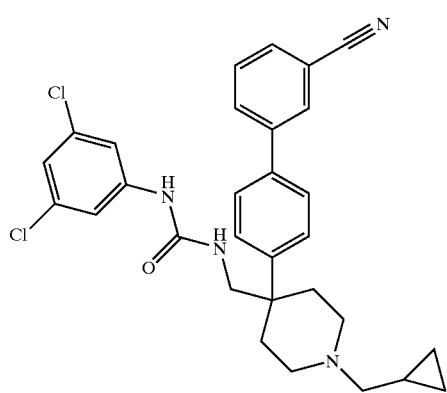
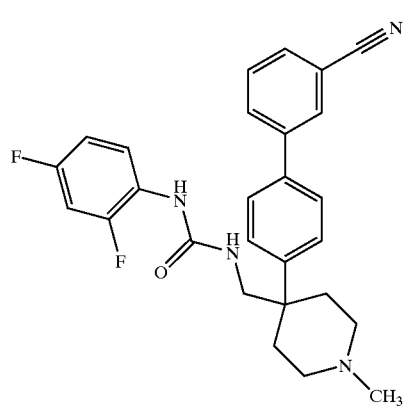
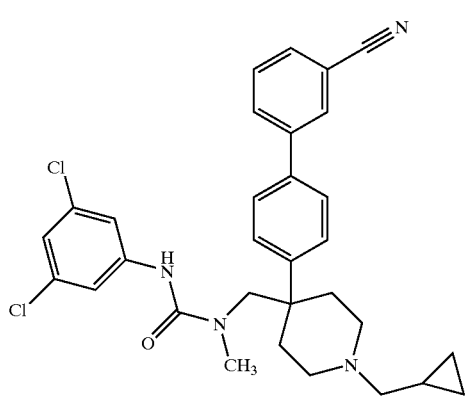
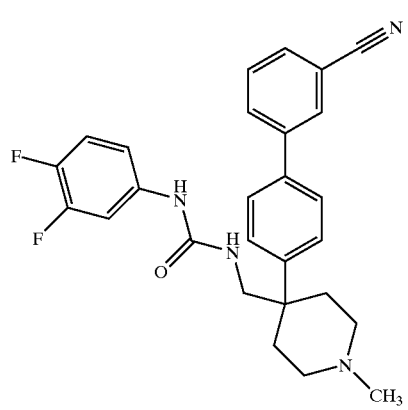
138
-continued
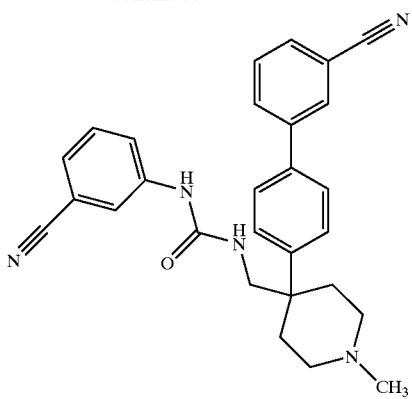
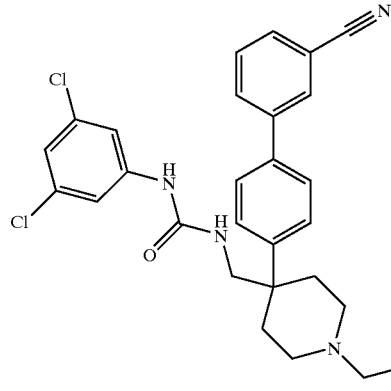
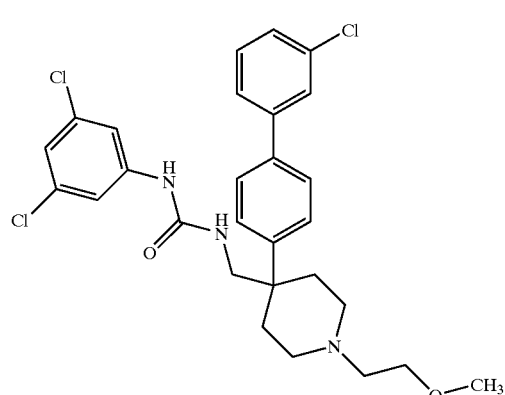
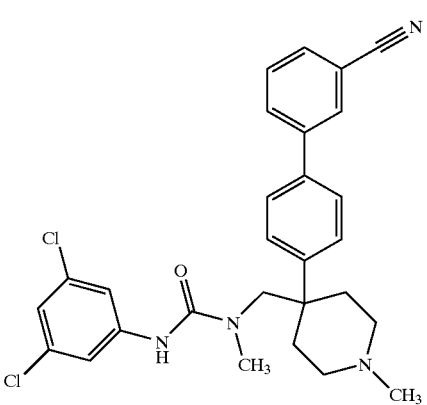

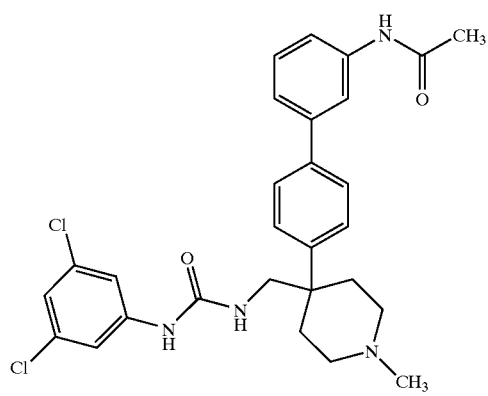
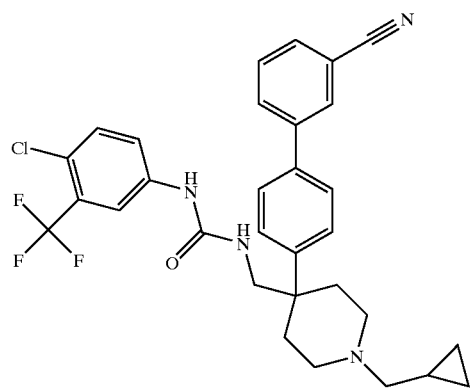
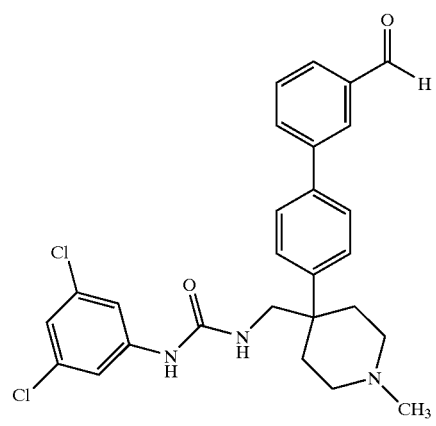
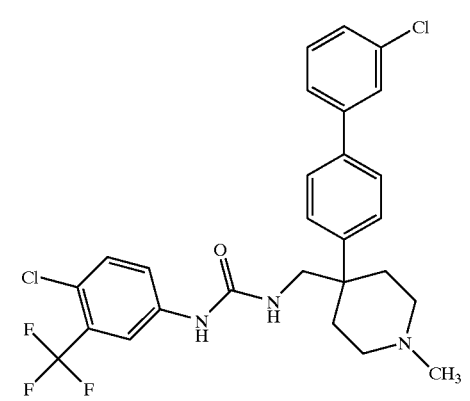
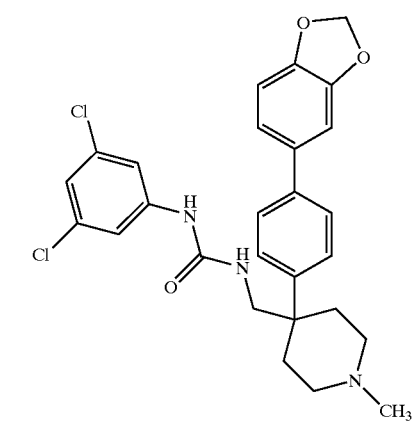
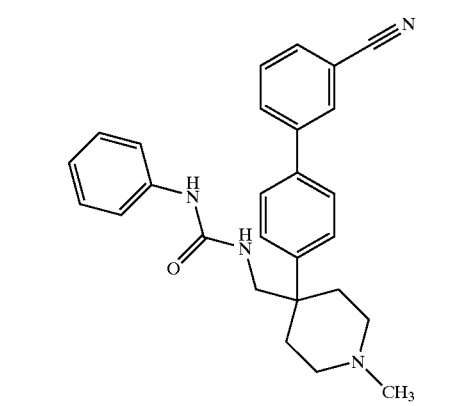
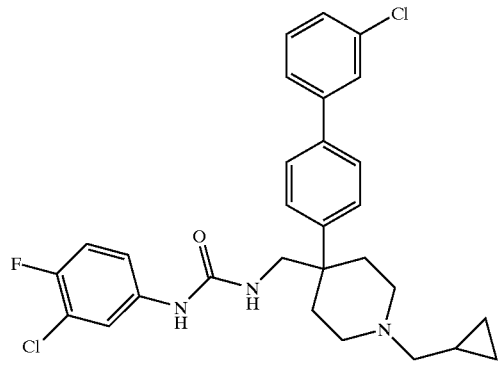
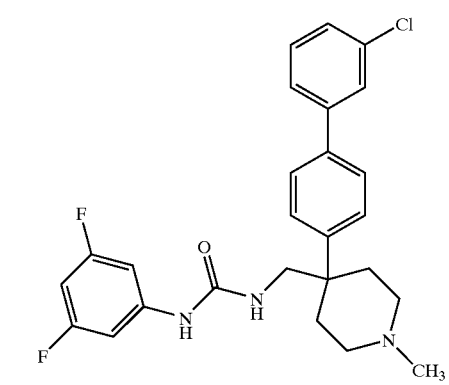

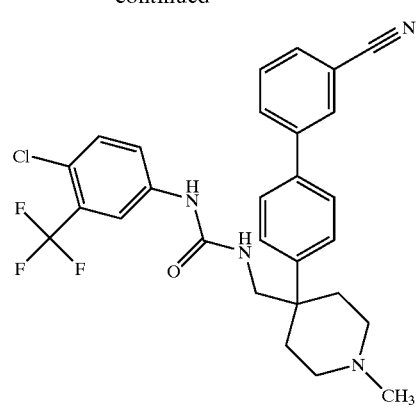
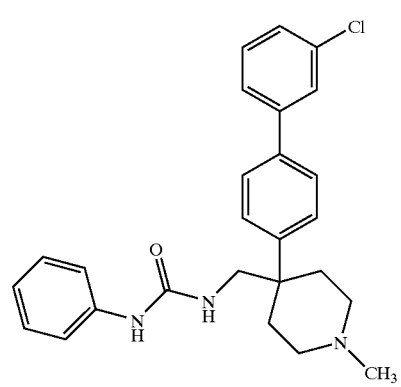
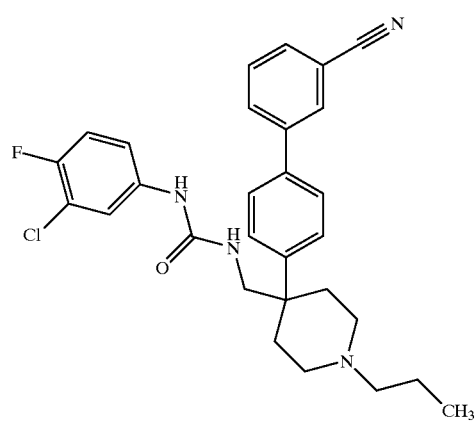
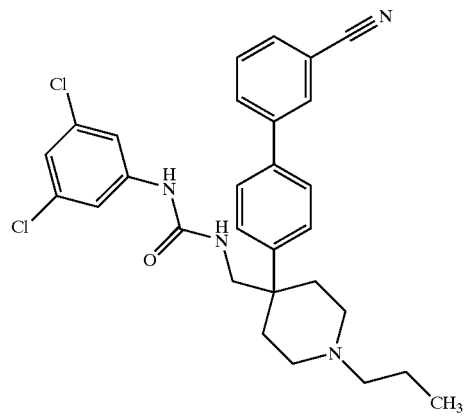
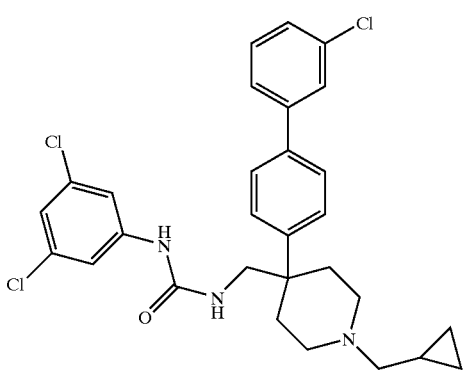
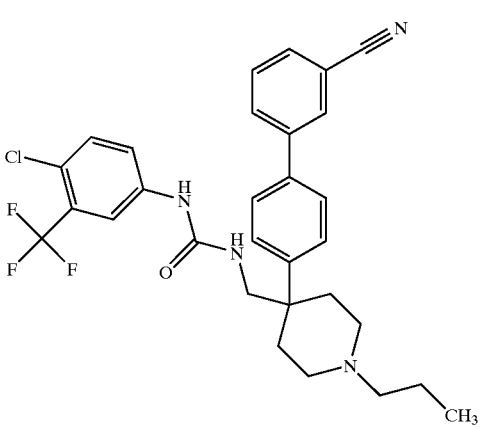
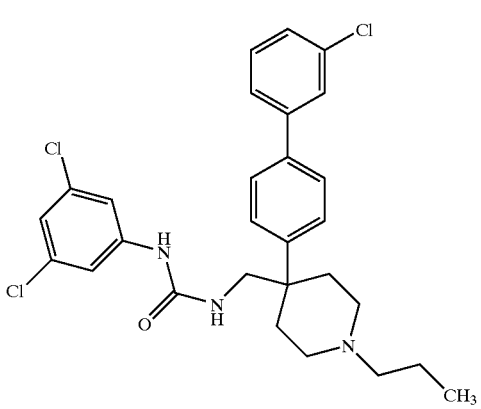
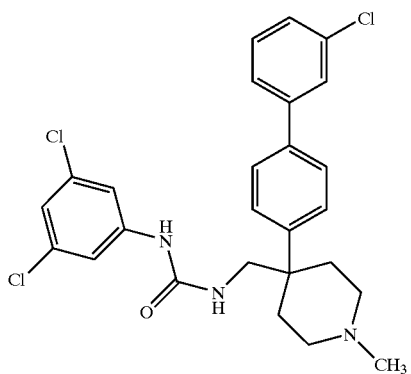

-continued
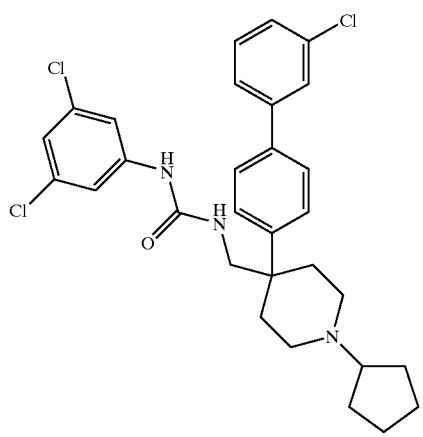
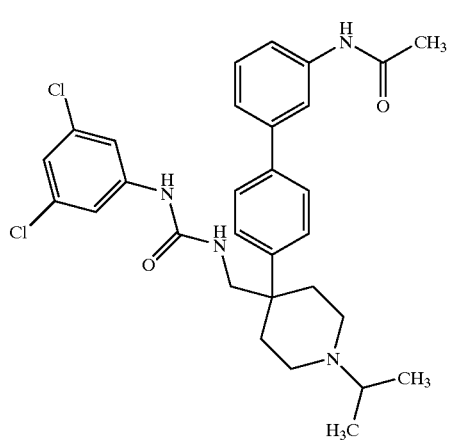
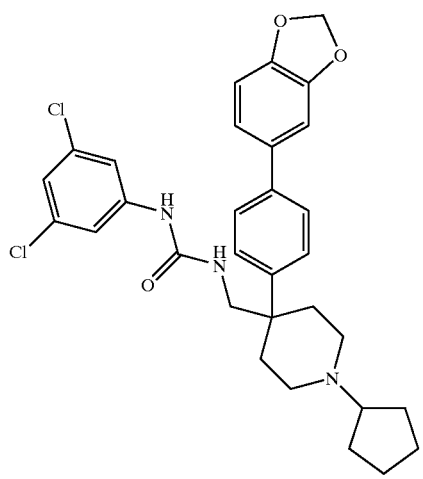
-continued
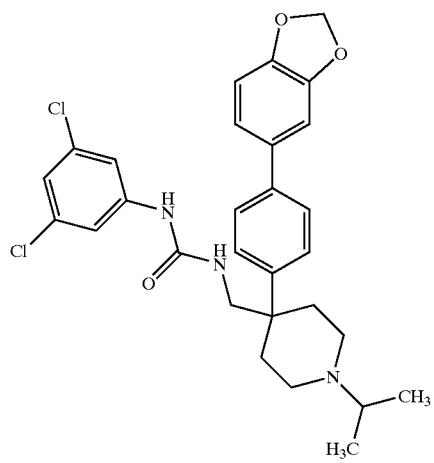
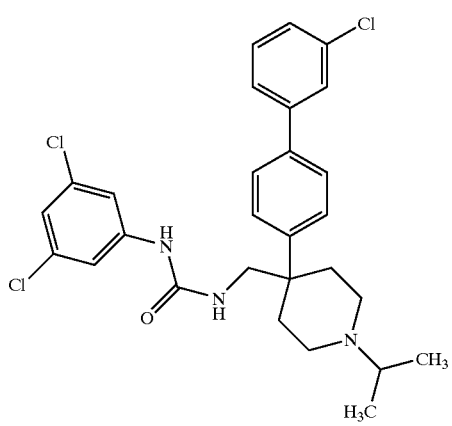
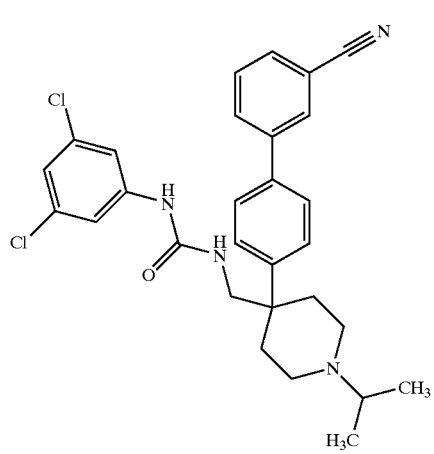

145
-continued
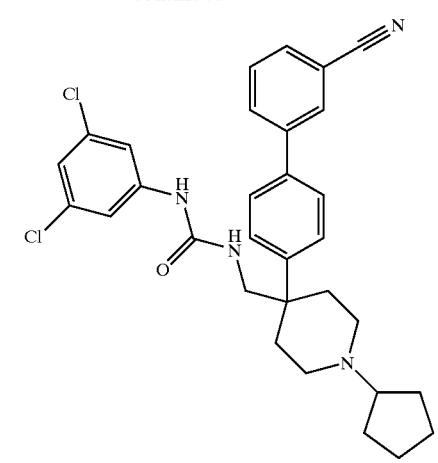
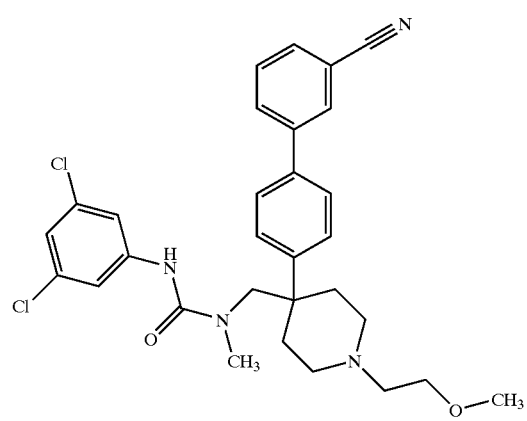
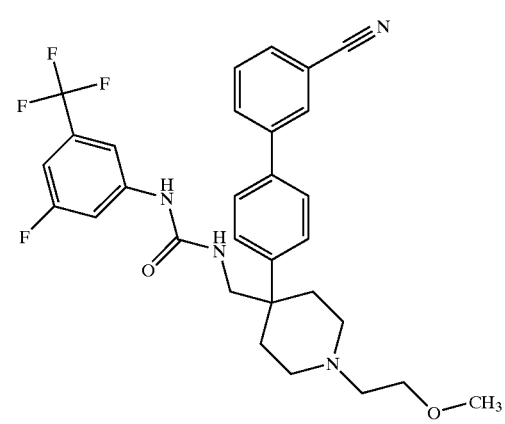
146
-continued
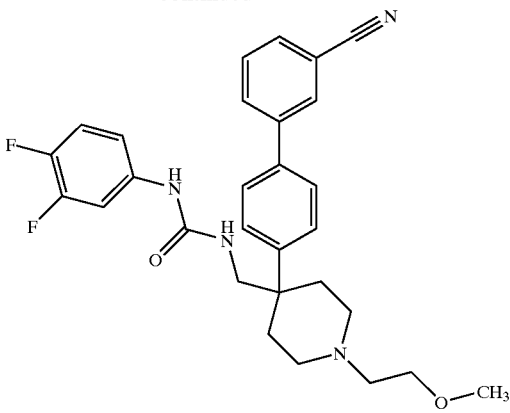
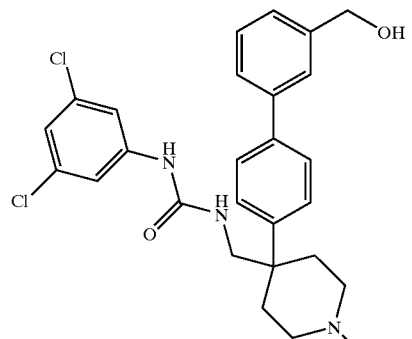
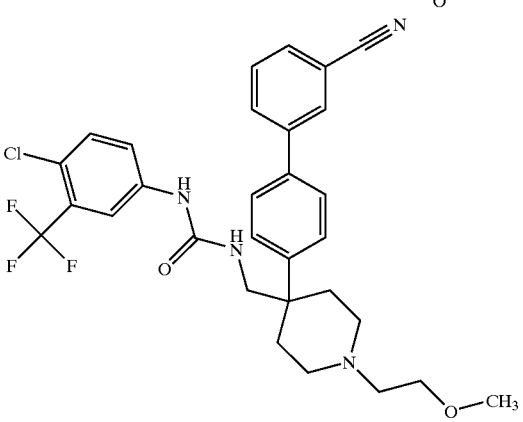

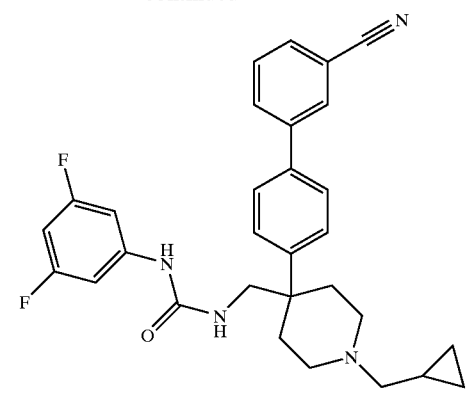
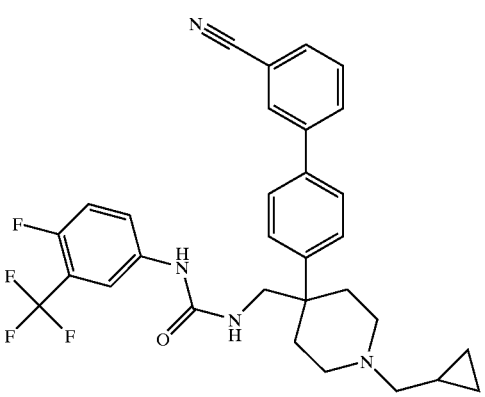
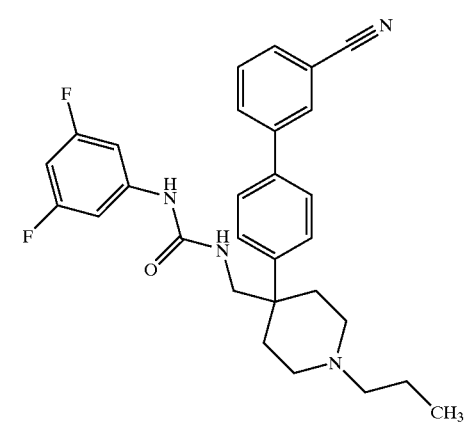
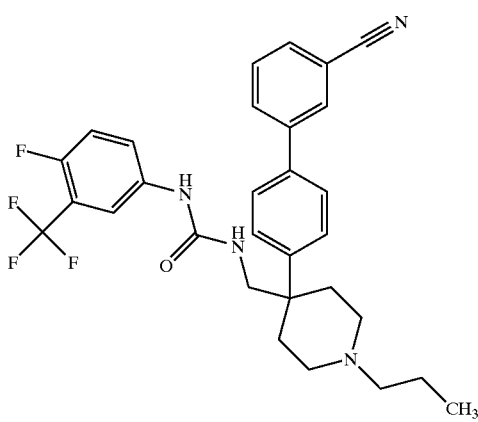
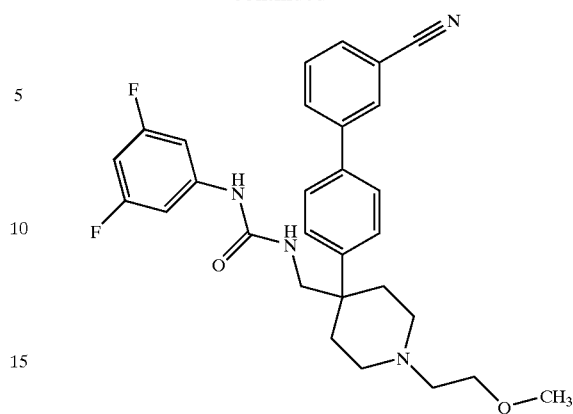
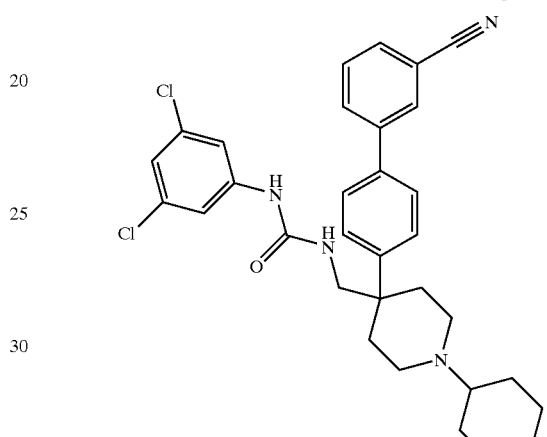
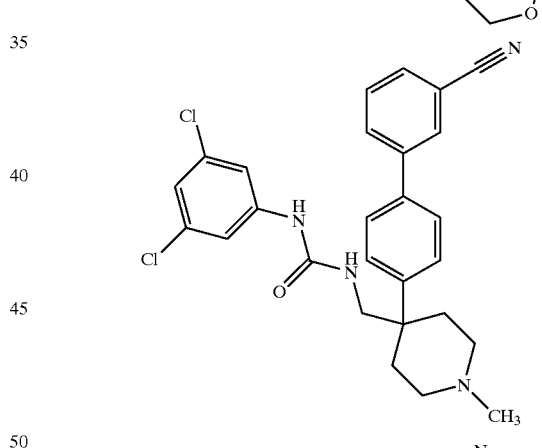
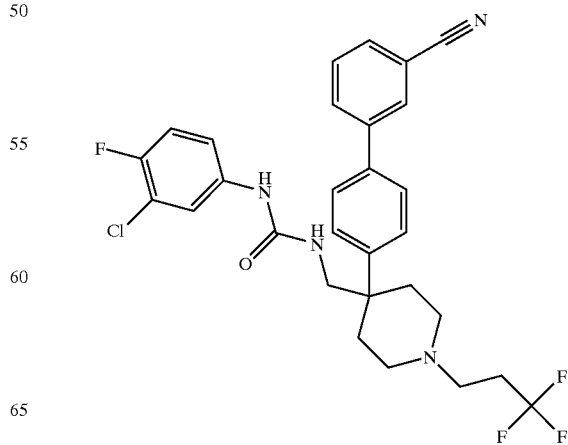

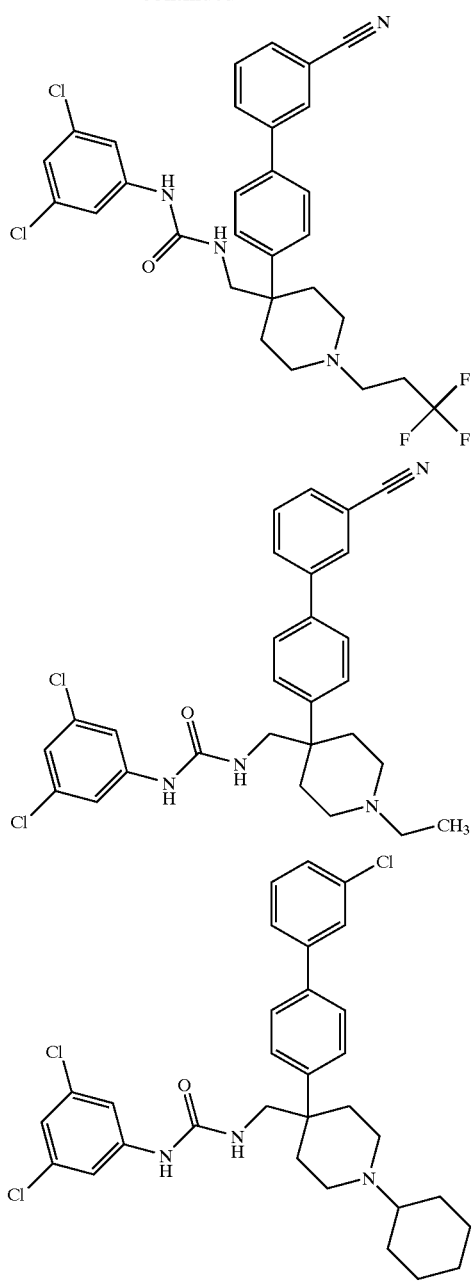
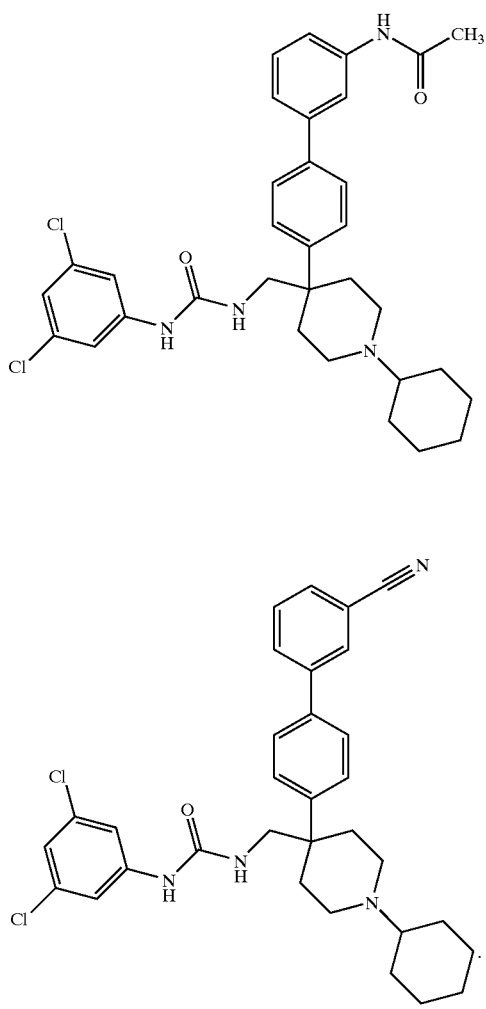
27. A pharmaceutical composition for treating obesity, said composition comprising therapeutically effective obesity-treating amounts of at least one compound of claim 26 and a pharmaceutically acceptable carrier.
* * * * *

UNITED STATES PATENT AND TRADEMARK OFFICE
CERTIFICATE OF CORRECTION

PATENT NO.    : 6,887,889 B2
DATED         : May 3, 2005
INVENTOR(S)   : Hobbs, Douglas W.

It is certified that error appears in the above-identified patent and that said Letters Patent is hereby corrected as shown below:

Column 133,
Line 48, please correct "Ar1:" to -- Ar1 is: --.

Column 134,
Line 57, please delete "or pyridyl".

Column 135,
Line 29, please correct "salts, said compound having" to -- salts, or solvates of said compound, said compound having --.

Signed and Sealed this

Thirtieth Day of August, 2005

JON W. DUDAS
*Director of the United States Patent and Trademark Office*